(12) United States Patent
McFarland

(10) Patent No.: US 10,766,915 B2
(45) Date of Patent: Sep. 8, 2020

(54) METAL-BASED COORDINATION COMPLEXES AS PHOTODYNAMIC COMPOUNDS AND THEIR USE

(71) Applicant: Sherri Ann McFarland, Mount Uniacke (CA)

(72) Inventor: Sherri Ann McFarland, Mount Uniacke (CA)

(*) Notice: Subject to any disclaimer, the term of this patent is extended or adjusted under 35 U.S.C. 154(b) by 0 days.

(21) Appl. No.: 14/777,169

(22) PCT Filed: Mar. 17, 2014

(86) PCT No.: PCT/US2014/030194
§ 371 (c)(1),
(2) Date: Sep. 15, 2015

(87) PCT Pub. No.: WO2014/145428
PCT Pub. Date: Sep. 18, 2014

(65) Prior Publication Data
US 2016/0039854 A1 Feb. 11, 2016

Related U.S. Application Data

(60) Provisional application No. 61/801,674, filed on Mar. 15, 2013.

(51) Int. Cl.
C07F 15/00 (2006.01)
A61K 41/00 (2020.01)
A61K 31/473 (2006.01)

(52) U.S. Cl.
CPC ........ C07F 15/0053 (2013.01); A61K 31/473 (2013.01); A61K 41/0057 (2013.01); C07F 15/0026 (2013.01)

(58) Field of Classification Search
CPC .................. C07F 15/0026; C07F 15/0053
See application file for complete search history.

(56) References Cited

U.S. PATENT DOCUMENTS

| 4,730,902 | A | | 3/1988 | Suzuki et al. |
| 5,350,644 | A | * | 9/1994 | Graetzel ............. H01G 9/2031 429/111 |
| 9,345,769 | B2 | | 5/2016 | McFarland |

FOREIGN PATENT DOCUMENTS

| CA | 2005039 A1 | 6/1991 |
| CA | 2090772 A1 | 8/1993 |
| CA | 2133284 A1 | 3/1996 |
| CA | 2225214 A1 | 1/1997 |
| CA | 2221912 A1 | 5/1999 |
| CA | 2315668 A1 | 7/1999 |
| CA | 2336582 A1 | 1/2000 |
| CA | 2353554 A1 | 6/2000 |
| CA | 2123124 C | 1/2003 |
| CA | 2458476 A1 | 3/2003 |
| CA | 2418410 A1 | 8/2003 |
| CA | 2199399 C | 2/2004 |
| CA | 2498231 A1 | 2/2004 |
| CA | 2506296 A1 | 6/2004 |
| CA | 2174209 C | 1/2005 |
| CA | 2535584 A1 | 2/2005 |
| CA | 2578280 A1 | 2/2006 |
| CA | 2237056 C | 10/2006 |
| CA | 2652590 A1 | 11/2007 |
| CA | 2691047 A1 | 12/2008 |
| CA | 2800122 A1 | 10/2011 |
| CA | 2797921 A1 | 12/2011 |
| CA | 2970026 A1 | 6/2016 |
| CA | 3038977 A1 | 4/2017 |
| EP | 1798222 A1 | 6/2007 |
| PL | 197232 B1 | 3/2008 |
| RU | 2089555 C1 | 9/1997 |
| WO | 9639144 A1 | 12/1996 |
| WO | 02098417 A1 | 12/2002 |

OTHER PUBLICATIONS

Klassen "Synthesis and spectroscopic characterization of ruthenium and osmium complexes with sterically hindering ligands. 2. Tris complexes with 2-(2'-pyridyl)quinoline and 2,2'-biquinoline" Inorganic Chemistry (1976), 15(12), 3166-8.*
Uhlig et al. CAS Accession No. 1976:25285.*
Belser et al. "Synthese, spektroskopische Eigenschaften and elektrochemisches Verhalten von Ruthenium(II)-Komplexen mit zweizähnigen Stickstoffliganden" Helvetica Chimica Acta, 1980, vol. 63, pp. 1675-1702.*
Thummel et al. "A ruthenium tris(diimine) complex with three different ligands" Inorganic Chemistry, 1987, vol. 26, pp. 3072-3074.*
Klassen, CAS Accession No. 1983:80840.*
Harris et al. CAS Accession No. 1972:500564.*
von Zelewsky et al. "126. Ruthenium(II) Complexes with Three Different Diimine Ligands" Helvetica Chinnica Acta, 1988, vol. 71, p. 1108-1115.*
Klinnant et al. CAS Accession No. 1995:36681.*
Anderson et al. "Designed Synthesis of Mononuclear Tris(heteroleptic) Ruthenium Complexes Containing Bidentat Polypyridyl Ligands" Inorganic Chemistry, 1995, vol. 34, pp. 6145-6157.*
Juris et al., "Ru(II) polypyridine complexes: photophysics, photochemistry, eletrochemistry, and chemiluminescence," Coordination Chemistry Reviews, vol. 84, pp. 85-277 (1988).
Myrick et al., "Evidence for static localization in the lowest optically excited states of ruthenium(II) diimine complexes: a solvent- and time-dependent photoselection study at 77 K", J. Am. Chem. Soc., vol. 110, No. 5, pp. 1325-1336 (1988).

(Continued)

Primary Examiner — Joseph R Kosack
(74) Attorney, Agent, or Firm — Caesar Rivise, PC

(57) ABSTRACT

Compositions of the invention include metal-based coordination complexes, which are preferably tunable photodynamic compounds. The compositions and complexes are useful as therapeutic agents and as in vivo diagnostic agents for treating or preventing diseases including those that involve hyperproliferating cells in their etiology, such as cancer. Compositions and complexes of the invention are further capable of destroying microbial cells, such as bacteria, fungi, and protozoa, and destroying viruses. The compositions and complexes are also capable of modulating cell function in other ways.

4 Claims, 11 Drawing Sheets

(56) References Cited

OTHER PUBLICATIONS

Sandroni et al., "First application of the HETPHEN concept to new heteroleptic bis(diimine) copper(I) complexes as sensitizers in dye sensitized solar cells", Dalton Transactions, vol. 42, No. 30., pp. 10818-10827 (2013).
Wachter et al., "Light-activated ruthenium complexes photobind DNA and are cytotoxic in the photodynamic therapy window," Chem. Commun., vol. 48, No. 77, pp. 9649-9651 (2012).
International Search Report for PCT/US2015/030194 dated Dec. 2, 2014.
Alessio et al. (2004). Ruthenium antimetastatic agents. Current topics in medicinal chemistry, 4(15), 1525-1535.
Bergamo et al. (2010). In viva tumour and metastasis reduction and in vitro effects on invasion assays of the ruthenium RM175 and osmium AFAP51 organometallics in the mammary cancer model. Journal of inorganic biochemistry, 104(1), 79-86.
Cullander, C. (1998). Light microscopy of living tissue: the state and future of the art. In Journal of Investigative Dermatology Symposium Proceedings (vol. 3, No. 2, pp. 166-171). Elsevier.
Hartinger et al. (2006). From bench to bedside—preclinical and early clinical development of the anticancer agent indazolium trans-[tetrachlorobis(1H-indazole)ruthenate(III)](KP1019 or FFC14A). Journal of inorganic biochemistry, 100(5), 891-904.
Kinoshita et al. (2012). Enhancement of near-IR photoelectric conversion in dye-sensitized solar cells using an osmium sensitizer with strong spin-forbidden transition. The journal of physical chemistry letters, 3(3), 394-398.
Kostrhunova et al. (2008). DNA interactions of monofunctional organometallic osmium (II) antitumor complexes in cell-free media. Journal of medicinal chemistry, 51(12), 3635-3643.

Ni et al. (2011). Osmium (VI) complexes as a new class of potential anti-cancer agents. Chemical Communications, 47 (7), 2140-2142.
Starkey et al. (2008). New two-photon activated photodynamic therapy sensitizers induce xenograft tumor regressions after near-IR laser treatment through the body of the host mouse. Clinical Cancer Research, 14(20), 6564-6573.
Batista et al., "Synthesis and characterization of novel (oligo)thienyl-imidazo-phenanthrolines as versatile π-conjugated systems for several optical applications", Tetrahedron 64, pp. 9230-9238 (2008).
Cai et al., "Degenerate four-wave mixing determination of third-order optical nonlinearities of three mixed ligand nickel (II) complexes", Journal of Molecular Structure, vol. 1006, pp. 282-287 (2011).
Database Registry Chemical Abstracts Service, Columbus, Ohio, Accession No. RN 1233733-23-7, Entered STN: Jul. 23, 2010.
Database Registry Chemical Abstracts Service, Columbus, Ohio, Accession No. RN 1268159-46-1, Entered STN: Mar. 11, 2011.
Gringauz, "Introduction to Medicinal Chemistry", pp. 32-35 (1997).
Li et al., "pH effects on optical and DNA binding properties of a thiophene-containing ruthenium(II) complex", Inorganica Chimica Acta, vol. 370, pp. 132-140 (2011).
Pedras et al, "Synthesis, characterization, photophysical studies and interaction with DNA of a new family of Ru(II) furyl- and thienyl-imidazo-phenanthroline polypyridyl complexes", Inorganica Chimica Acta, vol. 381, pp. 95-103 (2012).
Srinivasan et al., "Metal-metal communication in diruthenium complexes of the bridging ligand bis(imidazo[4,5-f][1,10]phenanthroline)", Inorganica Chimica Acta, vol. 366, pp. 116-121 (2011).
Office Action dated May 7, 2020 in CA App. No. 2,907,356.

\* cited by examiner $$\frac{\epsilon_a - \epsilon_f}{\epsilon_b - \epsilon_f} = \frac{b - (b^2 - 2K_b^2 C_t [\text{DNA}]_t/s)^{1/2}}{2K_b C_t}$$

METAL-BASED COORDINATION COMPLEXES AS PHOTODYNAMIC COMPOUNDS AND THEIR USE

BACKGROUND OF THE INVENTION

1. Field of Invention

This invention relates to metal-based coordination complexes that are useful as therapeutic and diagnostic agents. The invention further relates to photodynamic compounds that can be activated with ultraviolet to infrared (UV-IR) light, particularly near infrared light, that are useful as therapeutic and diagnostic agents. In particular, the invention provides tunable metal-based photodynamic compounds that are coordination complexes derived from organic ligands. The photodynamic compounds can be activated by light to destroy unwanted cells, for example hyperproliferative cells and microbial cells. The photodynamic compounds can also be activated by light to destroy viruses.

2. Description of Related Art

Photodynamic therapy (PDT) is currently an active area of research for the treatment of diseases associated with hyperproliferating cells such as cancer and non-malignant lesions. The development of new photodynamic compounds (PDCs) for photodynamic therapy (PDT) has been increasingly focused on metallosupramolecular complexes derived from metals such as ruthenium and rhodium. The ongoing investigation of new photosensitizers for PDT stems from the limitations associated with traditional organic-based porphyrins such as Photofrin®, which must be activated with relatively short wavelengths of light and do not function in hypoxic environments. Significant advances have been made toward overcoming these limitations with the introduction of mixed-metal complexes that possess low-lying $^3$MMCT (metal-to-metal charge transfer) excited states. To date, however, there has been limited reporting of metal based photodynamic compounds that are capable of providing photodynamic therapy for the treatment of diseases associated with hyperproliferating cells such as cancer and non-malignant lesions.

There is a long felt need for new photodynamic compounds (PDCs) that are useful as photosensitizers for PDT that are both disease-modifying and effective in treating patients with diseases caused by hyperproliferating cells, for example, cancer. There is also a long felt need for new PDCs that are useful as in vivo diagnostic agents. The present invention addresses the need to develop novel PDCs that are useful as photosensitizers for PDT that are both disease-modifying and effective in treating patients with diseases caused by hyperproliferating cells, for example, cancer. The present invention also addresses the long felt need for new PDCs that are useful as in vivo diagnostic agents.

All references cited herein are incorporated herein by reference in their entireties.

BRIEF SUMMARY OF THE INVENTION

The present invention is directed toward novel compounds of formula (I),

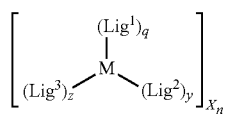

including hydrates, solvates, pharmaceutically acceptable salts, prodrugs and complexes thereof, wherein:

M at each occurrence is independently selected from the group consisting of osmium, manganese, molybdenum, rhenium, ruthenium, iron, cobalt, rhodium, iridium, nickel, platinum, palladium, vanadium, chromium, tungsten, technetium, and copper;

X is selected from the group consisting of Cl$^-$, PF$_6^-$, Br$^-$, BF$_4^-$, ClO$_4^-$, CF$_3$SO$_3^-$, and SO$_4^{-2}$;

n=0, 1, 2, 3, 4, or 5;

q is independently at each occurrence 0, 1, or 2;

y is independently at each occurrence 0, 1, or 2;

z is independently at each occurrence 1, 2, or 3;

Lig$^1$ is a bidentate ligand that at each occurrence is each independently selected from the group consisting of

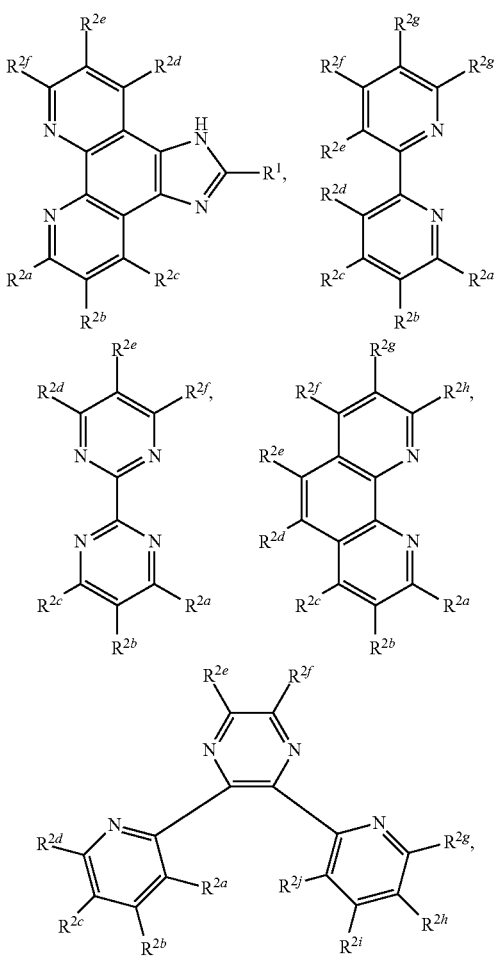

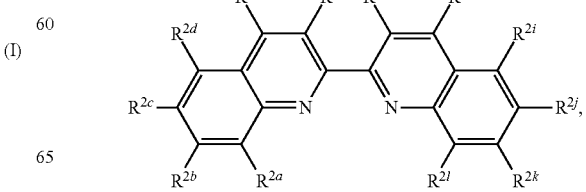

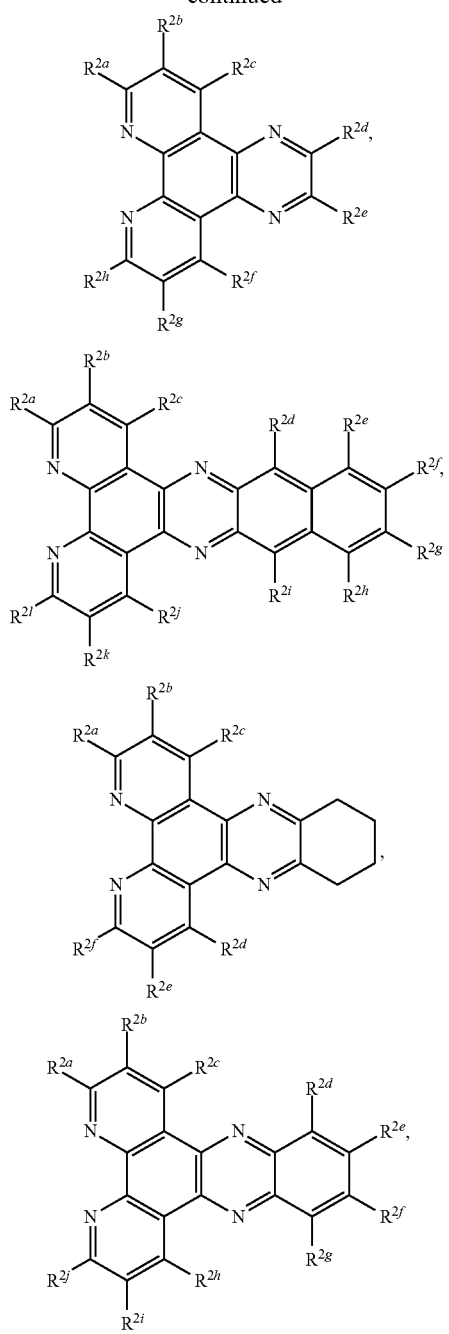
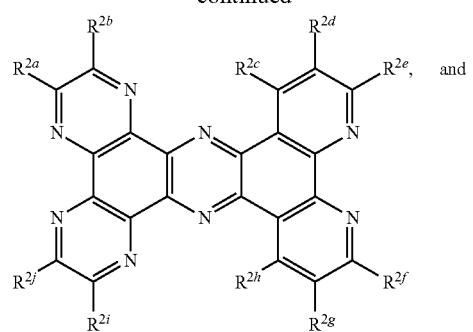
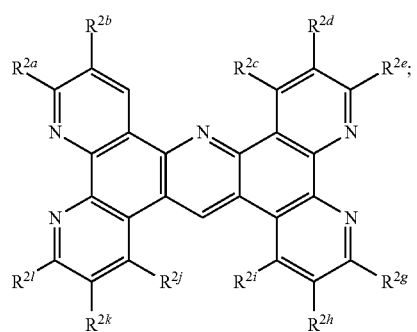
Lig² is a bidentate ligand that at each occurrence is each independently selected from the group consisting of
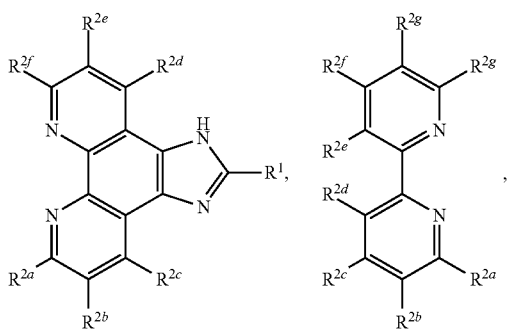
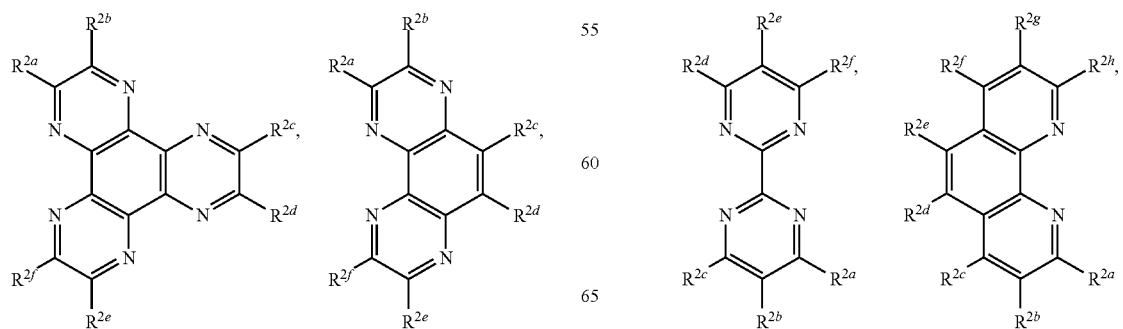

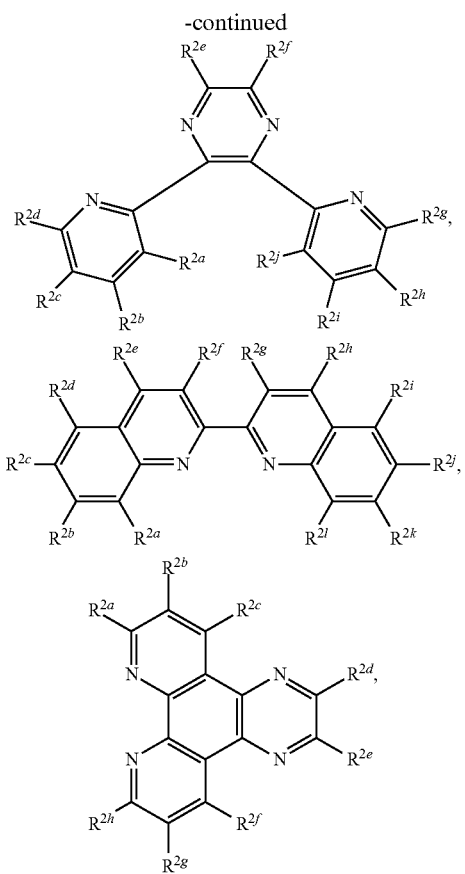
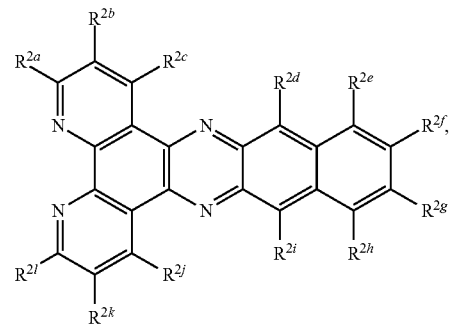
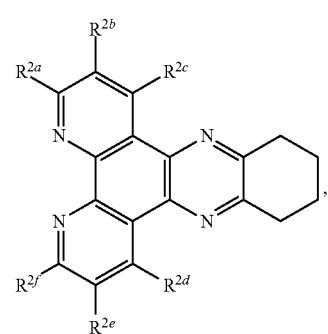
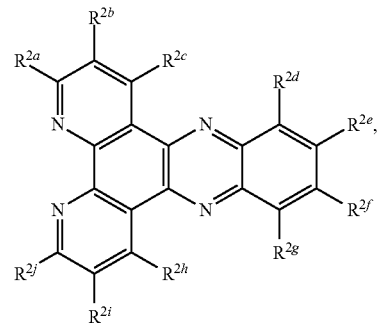
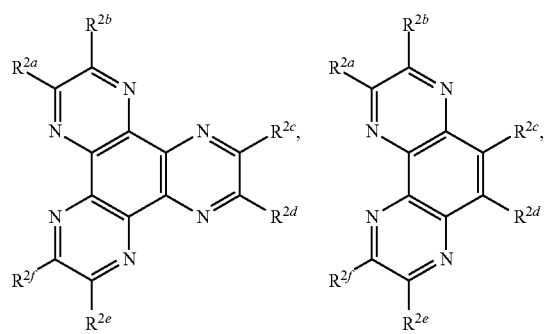
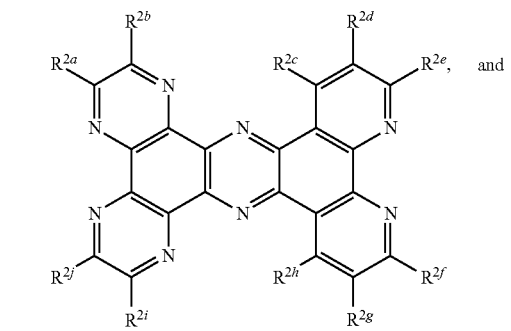
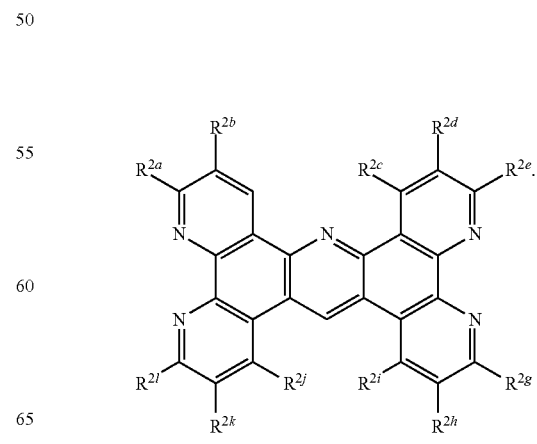
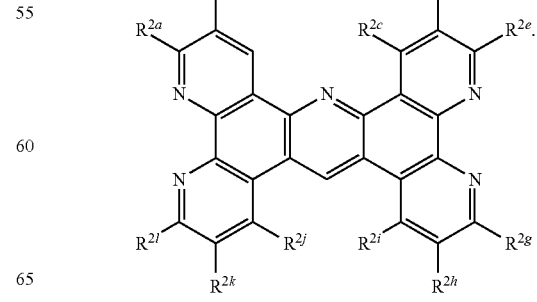

Lig³ is a bidentate ligand that at each occurrence is each independently selected from the group consisting of
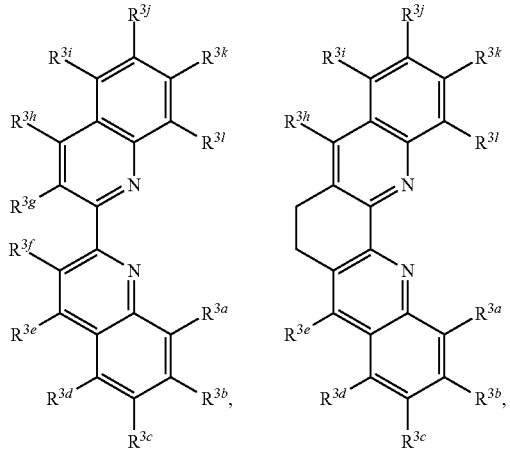
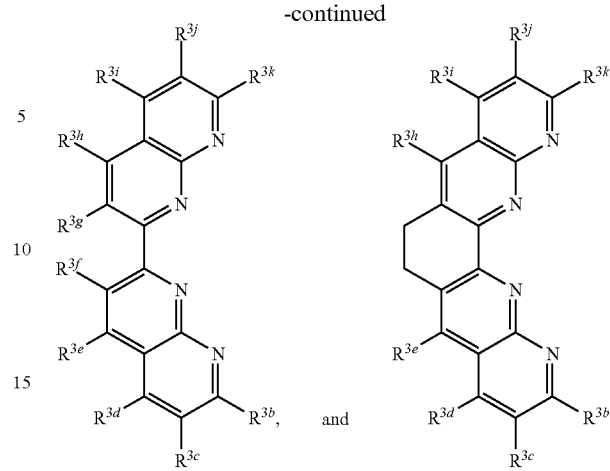
R¹ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,
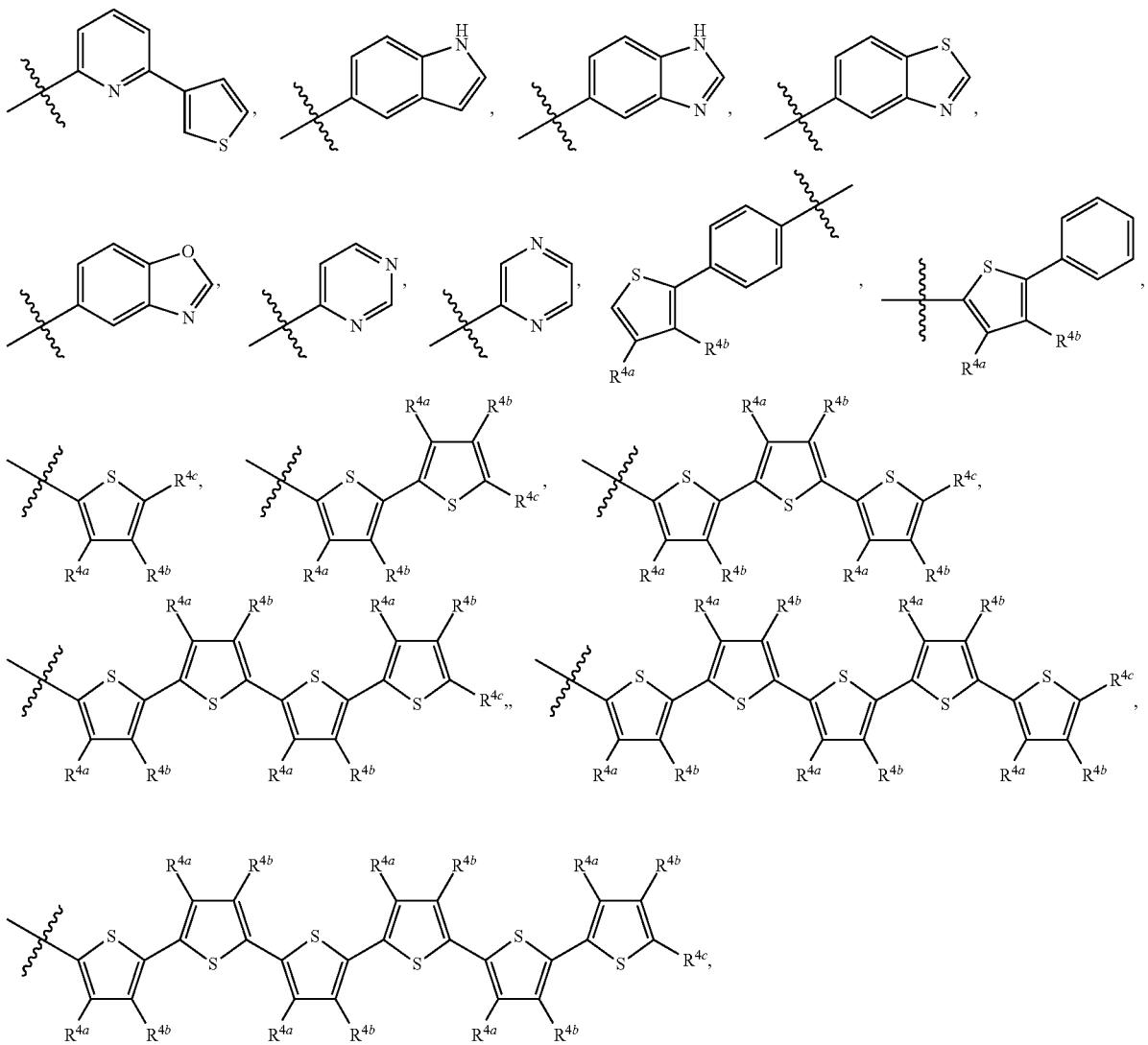

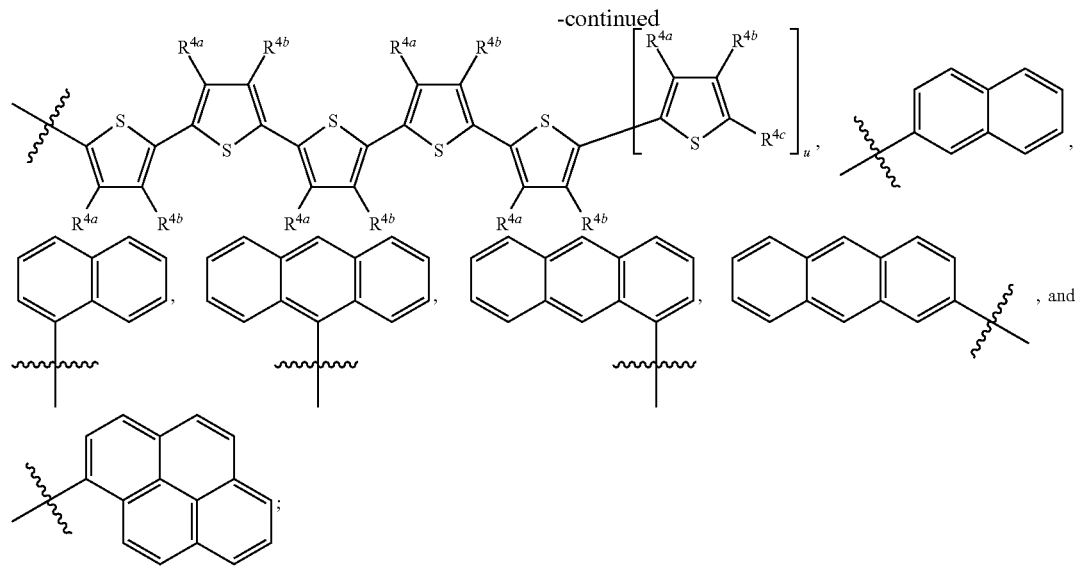

u is an integer;

$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, $SO_3H$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6{}_2$, $NR^7{}_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl;

$R^8$ at each occurrence are each independently selected from the group consisting of hydrogen and optionally substituted alkyl;

Compounds of the structure

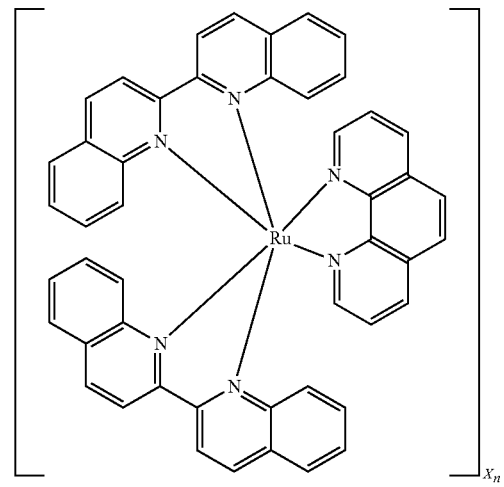

are excluded from the novel compounds of formula (I).

The compounds of the present invention includes compounds having formula (II),

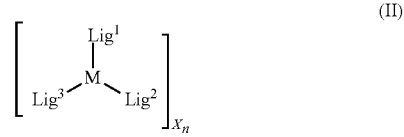

(II)

including hydrates, solvates, pharmaceutically acceptable salts, prodrugs and complexes thereof.

The compounds of the present invention includes compounds having formula (III):

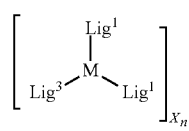
(III)

including hydrates, solvates, pharmaceutically acceptable salts, prodrugs and complexes thereof.

The compounds of the present invention includes compounds having formula (IV):

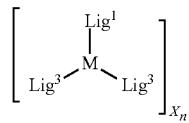
(IV)

including hydrates, solvates, pharmaceutically acceptable salts, prodrugs and complexes thereof.

The present invention is also directed toward novel compounds of formula (V):

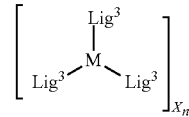
(V)

including hydrates, solvates, pharmaceutically acceptable salts, prodrugs and complexes thereof.

The present invention is also directed toward novel compounds of formula (VI):

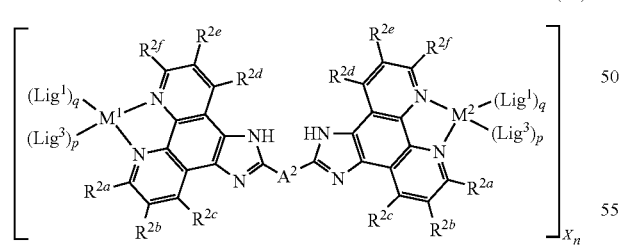
(VI)

including hydrates, solvates, pharmaceutically acceptable salts, prodrugs and complexes thereof wherein:

$M^1$ and $M^2$ at each occurrence is independently selected from the group consisting of osmium, manganese, molybdenum, rhenium, ruthenium, iron, cobalt, rhodium, iridium, nickel, platinum, palladium, vanadium, chromium, tungsten, technetium, and copper;

p is in each occurrence independently 0, 1, or 2, and one occurrence of p must be non-zero.

$A^2$ is selected from the group consisting of

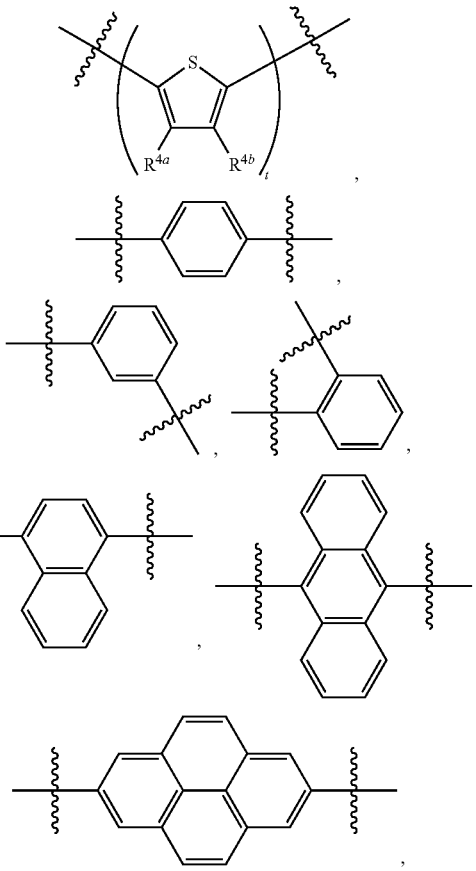

t is an integer.

The present invention is also directed toward novel compounds of formula (VII):

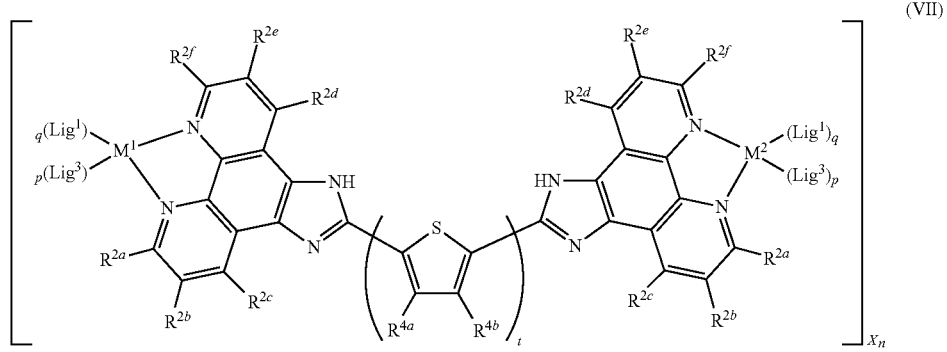
(VII)

including hydrates, solvates, pharmaceutically acceptable salts, prodrugs and complexes thereof.

The present invention is also directed toward novel compounds of formula (VIIa):

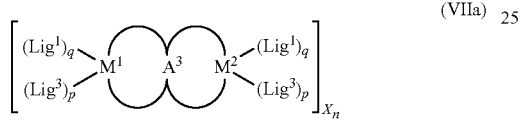
(VIIa)

including hydrates, solvates, pharmaceutically acceptable salts, prodrugs and complexes thereof wherein:

$A^3$ is selected from a group consisting of

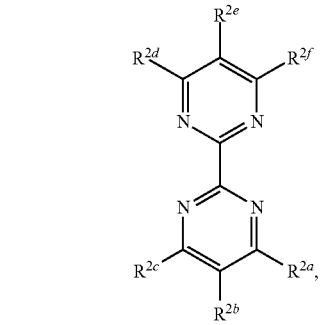

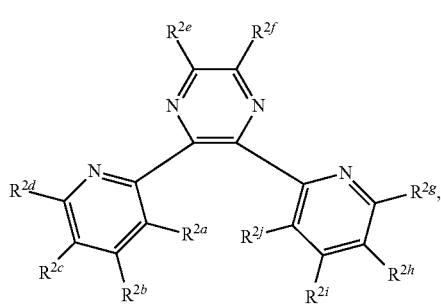

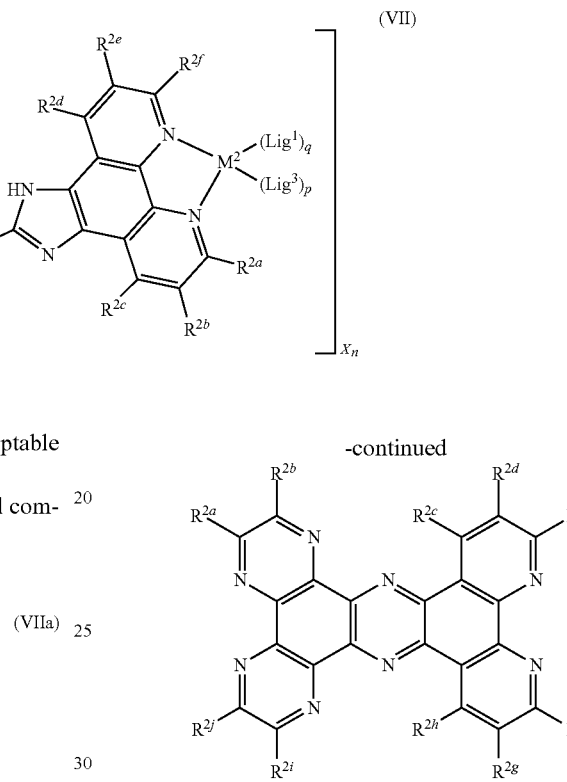

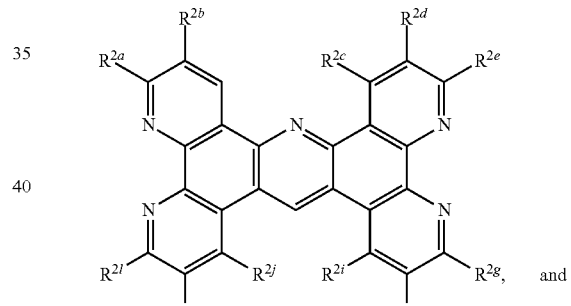

Wherein $A^3$ is a bridging ligand bound to $M^1$ as a bidentate ligand and $A^3$ is bound to $M^2$ as a bidentate ligand.

The present invention is also directed toward novel compounds of formula (VIIb):

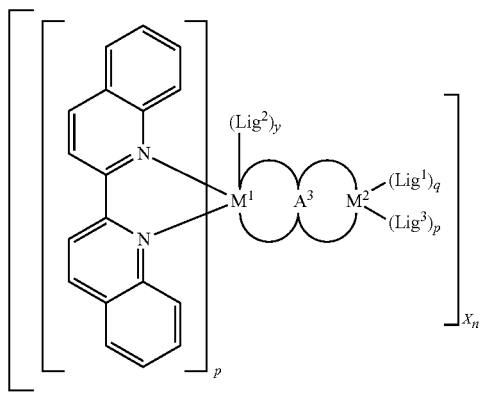
(VIIb)

including hydrates, solvates, pharmaceutically acceptable salts, prodrugs and complexes thereof.

The present invention is also directed toward novel compounds of formula (VIIc):

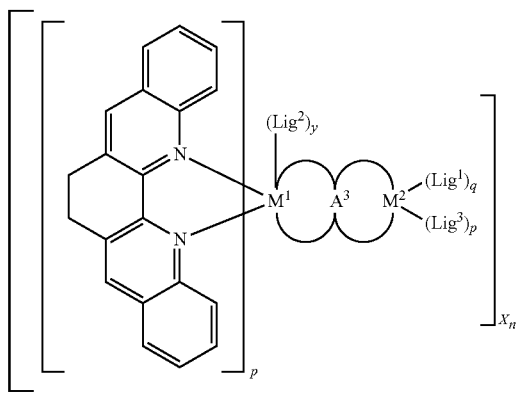
(VIIc)

including hydrates, solvates, pharmaceutically acceptable salts, prodrugs and complexes thereof.

The present invention is also directed toward novel compounds of formula (VIId):

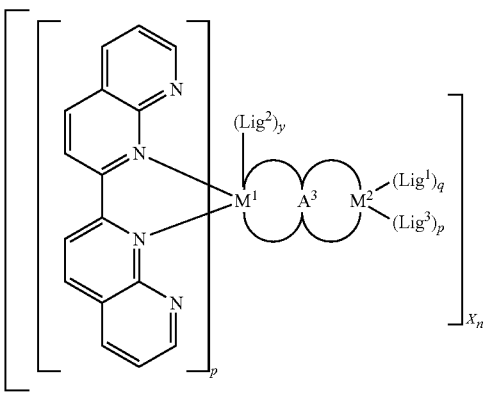
(VIId)

including hydrates, solvates, pharmaceutically acceptable salts, prodrugs and complexes thereof.

The present invention is also directed toward novel compounds of formula (VIIe):

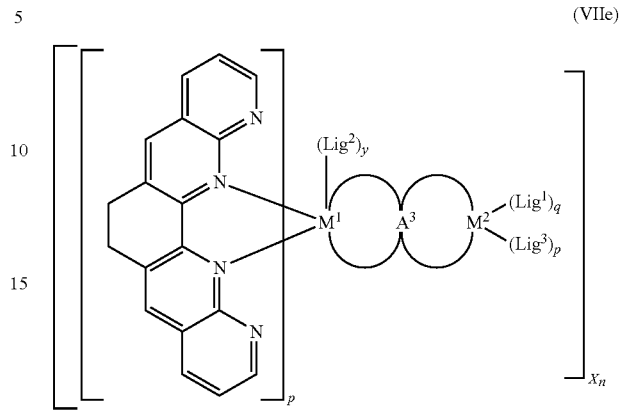
(VIIe)

including hydrates, solvates, pharmaceutically acceptable salts, prodrugs and complexes thereof.

The present invention is also directed toward novel compounds of formula (VIIf):

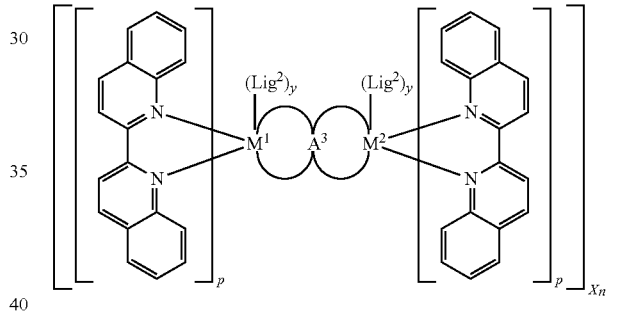
(VIIf)

including hydrates, solvates, pharmaceutically acceptable salts, prodrugs and complexes thereof.

The present invention further relates to compositions comprising:
an effective amount of one or more compounds according to the present invention and an excipient.

The present invention also relates to a method using the compounds of the invention as a DNA binding agent.

The present invention also relates to a method using the compounds according to the present invention and an excipient as a DNA binding agent.

The present invention also relates to a method using the compounds of the invention as a nucleic acid binding agent.

The present invention also relates to a method using the compounds according to the present invention and an excipient as a nucleic acid binding agent.

The present invention also relates to a method using the compounds of the invention as a protein binding agent.

The present invention also relates to a method using the compounds according to the present invention and an excipient as a protein binding agent.

The present invention also relates to a method using the compounds of the invention as a DNA photocleavage agent.

The present invention also relates to a method using the compounds according to the present invention and an excipient as a DNA photocleavage agent.

The present invention also relates to a method using the compounds of the invention as a DNA condensation agent.

The present invention also relates to a method using the compounds according to the present invention and an excipient as DNA condensation agent.

The present invention also relates to a method using the compounds of the invention as an agent that produces the DNA light-switch effect.

The present invention also relates to a method using the compounds according to the present invention and an excipient as an agent that produces the DNA light-switch effect.

The present invention also relates to a method using the compounds of the invention and an excipient as a photosensitizer that can function in Type I photoprocesses.

The present invention also relates to a method using the compounds of the invention as a photosensitizer that can function in Type I photoprocesses.

The present invention also relates to a method using the compounds of the invention and an excipient as a photosensitizer that can function in Type II photoprocesses.

The present invention also relates to a method using the compounds of the invention as a photosensitizer that can function in Type II photoprocesses.

The present invention also relates to a method using the compounds of the invention as a photosensitizer that can function in both Type I and Type II photoprocesses.

The present invention also relates to a method using the compounds according to the present invention and an excipient as a photosensitizer that can function in both Type I and Type II photoprocesses.

The present invention also relates to a method using the compounds of the invention to destroy unwanted cells, including hyperproliferating cells and microbial cells.

The present invention also relates to a method of using the compounds of the invention to destroy viruses.

The present invention also relates to a method of using the compounds of the invention to destroy unwanted cells, including hyperproliferating cells and microbial cells, using light as an activator.

The present invention also relates to a method of using the compounds of the invention to destroy viruses using light as an activator.

The present invention also relates to a method using the compounds according to the present invention and an excipient to destroy unwanted cells, including hyperproliferating cells and microbial cells.

The present invention also relates to a method using the compounds according to the present invention and an excipient to destroy viruses.

The present invention also relates to a method using the compounds of the invention to destroy cells, including bacteria fungi, and protozoa.

The present invention also related to a method of using the compounds of the invention to destroy cells, including bacteria fungi and protozoa, using light as an activator.

The present invention also relates to a method using the compounds according to the present invention and an excipient to destroy cells, including bacteria fungi, and protozoa.

The present invention also relates to a method using the compounds of the invention to induce apoptosis in cells, including hyperproliferating cells.

The present invention also relates to a method using the compounds according to the present invention and an excipient to induce apoptosis in cells, including hyperproliferating cells.

The present invention also relates to a method using the compounds of the invention to impart DNA crosslinking in cells, including hyperproliferating cells.

The present invention also relates to a method using the compounds according to the present invention and an excipient to impart DNA crosslinking in cells, including hyperproliferating cells.

The present invention also relates to a method for treating or preventing diseases that involve hyperproliferating cells etiology, including, for example, cancer, said method comprising administering to a subject an effective amount of a compound or composition according to the present invention.

The present invention yet further relates to a method for treating or preventing diseases that have hyperproliferating cells in their etiology, including, for example, cancer, wherein said method comprises administering to a subject a composition comprising an effective amount of one or more compounds according to the present invention and an excipient.

The present invention also relates to a method for treating or preventing diseases that involve hyperproliferating cells in their etiology, including, for example, cancer, said method comprising administering to a subject an effective amount of a compound or composition according to the present invention and an intracellular reducing agent such as glutathione.

The present invention also relates to a method for treating or preventing diseases that involve hyperproliferating cells in their etiology, including, for example, cancer, said method comprising administering to a subject an effective amount of a compound or composition according to the present invention and an excipient and an intracellular reducing agent such as glutathione.

The present invention also relates to a method for treating or preventing diseases that involve hyperproliferating cells in their etiology, including, for example, cancer, said method comprising administering to a subject an effective amount of a compound or composition according to the present invention and an intracellular oxidizing agent such as oxygen.

The present invention also relates to a method for treating or preventing diseases that involve hyperproliferating cells in their etiology, including, for example, cancer, said method comprising administering to a subject an effective amount of a compound or composition according to the present invention and an excipient and an intracellular oxidizing agent such as oxygen.

The present invention also relates to a method using the compounds of the invention as an in vivo diagnostic agent via intracellular luminescence or colorimetric methods.

The present invention also relates to a method using the compounds of the invention as immune-modulating agents to mediate the rejection of secondary tumors.

The present invention further relates to a method of preparing the compounds of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF PREFERRED EMBODIMENTS OF THE INVENTION

Figure 1:
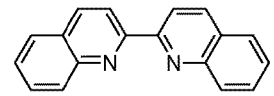
FIG. 1: Representative examples of the compounds of the disclosure.
Figure 1:
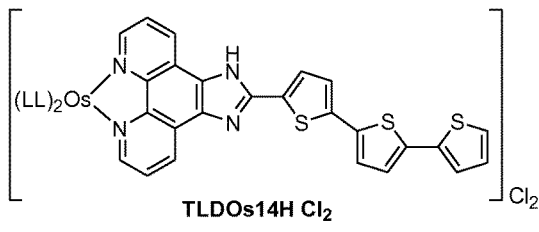
Figure 1:
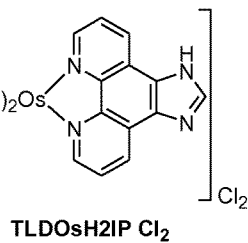
Figure 1:
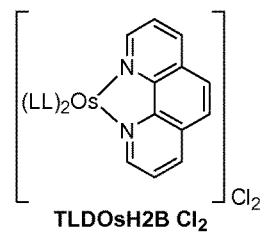
Figure 1:
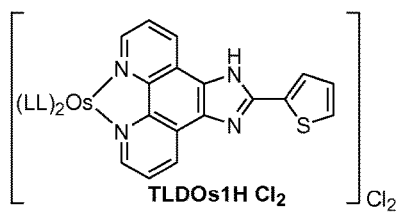
Figure 1:
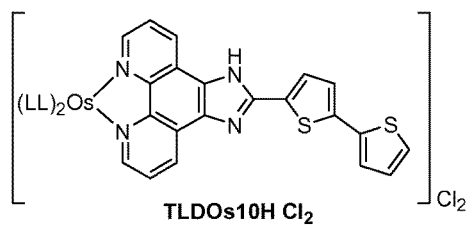
Figure 1:
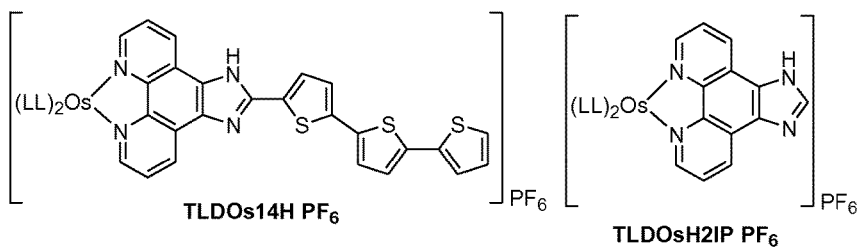
Figure 1:
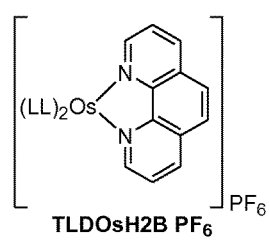
Figure 1:
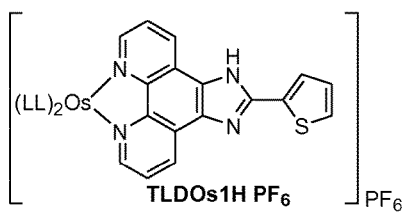
Figure 1:
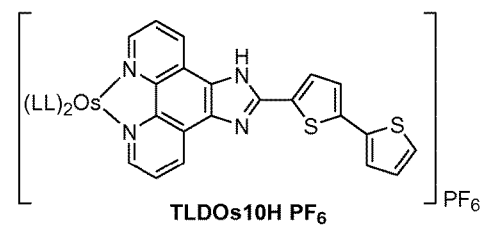

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$ amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., $-CF_3$, $-CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiophenyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

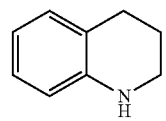

is, for the purposes of the present invention, considered a heterocyclic unit. 6,7-Dihydro-5H-cyclopentapyrimidine having the formula:

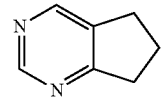

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

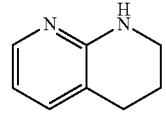

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —$NO_2$, oxo (=O), —$OR^9$, —$SR^9$, —$N(R^9)_2$, —$NR^9C(O)R^9$, —$SO_2R^9$, —$SO_2OR^9$, —$SO_2N(R^9)_2$, —$C(O)R^9$, —$C(O)OR^9$, —$C(O)N(R^9)_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —$NO_2$, oxo, and $R^x$; wherein $R^x$, at each occurrence, independently is hydrogen, —$OR^{10}$, —$SR^{10}$, —$C(O)R^{10}$, —$C(O)OR^{10}$, —$C(O)N(R^{10})_2$, —$SO_2R^{10}$, —$S(O)_2OR^{10}$, —$N(R^{10})_2$, —$NR^{10}C(O)R^{10}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^x$ units taken together with the atom(s) to which they are bound form an optionally substituted carbocycle or heterocycle wherein said carbocycle or heterocycle has 3 to 7 ring atoms; wherein $R^{10}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{10}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —$OR^{11}$; for example, —OH, —$OCH_3$, —$OCH_2CH_3$, —$OCH_2CH_2CH_3$;
ii) —$C(O)R^{11}$; for example, —$COCH_3$, —$COCH_2CH_3$, —$COCH_2CH_2CH_3$;
iii) —$C(O)OR^{11}$; for example, —$CO_2CH_3$, —$CO_2CH_2CH_3$, —$CO_2CH_2CH_2CH_3$;
iv) —$C(O)N(R^{11})_2$; for example, —$CONH_2$, —$CONHCH_3$, —$CON(CH_3)_2$;
v) —$N(R^{11})_2$; for example, —$NH_2$, —$NHCH_3$, —$N(CH_3)_2$, —$NH(CH_2CH_3)$;
vi) halogen: —F, —Cl, —Br, and —I;
vii) —$CH_eX_g$; wherein X is halogen, m is from 0 to 2, e+g=3; for example, —$CH_2F$, —$CHF_2$, —$CF_3$, —$CCl_3$, or —$CBr_3$;
viii) —$SO_2R^{11}$; for example, —$SO_2H$; —$SO_2CH_3$; —$SO_2C_6H_5$;
ix) $C_1$-$C_6$ linear, branched, or cyclic alkyl;
x) Cyano
xi) Nitro;
xii) $N(R^{11})C(O)R^{11}$;
xiii) Oxo (=O);
xiv) Heterocycle; and
xv) Heteroaryl.

wherein each $R^{11}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two $R^{11}$ units can be taken together to form a ring comprising 3-7 ring atoms. In certain aspects, each $R^{11}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the inventive compounds described herein, be they photodynamic or not, including all enantiomeric forms, diastereomeric forms, salts, and the like, and the terms "compound," "analog," and "composition of matter" are used interchangeably throughout the present specification.

For the purposes of the present invention the term "bpy" will stand equally well for 2,2'-bipyridine and [2,2']bipyridine.

For the purposes of the present invention the term "phen" will stand equally well for [1,10]phenanthroline and 1,10-phenanthroline.

For the purposes of the present invention the term "dmb" will stand equally well for 4,4'-dimethyl-2,2'-bipyridine.

For the purposes of the present invention the term "biq" will stand equally well for 2,2'-biquinoline.

For the purposes of the present invention the term "dpq" will stand equally well for

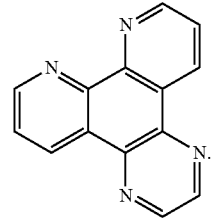 [SMILES: c1cnc2c(c1)c1nccnc1c1cccnc12]

For the purposes of the present invention the term "dppz" will stand equally well for

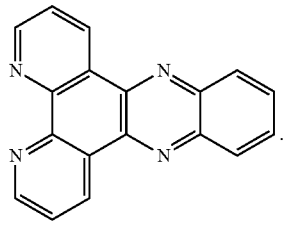 [SMILES: c1ccc2nc3c4cccnc4c4ncccc4c3nc2c1]

For the purposes of the present invention the term "dppn" will stand equally well for For the purposes of the present invention the term "dpqC" will stand equally well for

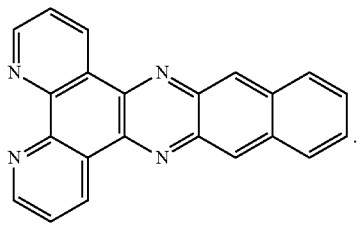 [SMILES: c1ccc2cc3nc4c5cccnc5c5ncccc5c4nc3cc2c1]

For the purposes of the present invention the term "dppza" will stand equally well for

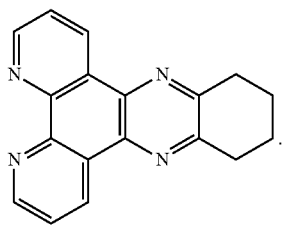 [SMILES: c1cnc2c(c1)c1nc3c(nc1c1cccnc12)CCCC3]

For the purposes of the present invention the term "dppzc" will stand equally well for

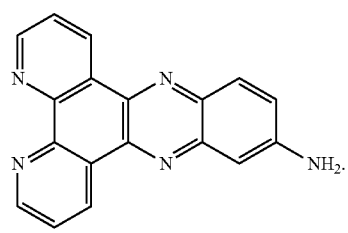 [SMILES: Nc1ccc2nc3c4cccnc4c4ncccc4c3nc2c1]

For the purposes of the present invention the term "dppzs" will stand equally well for

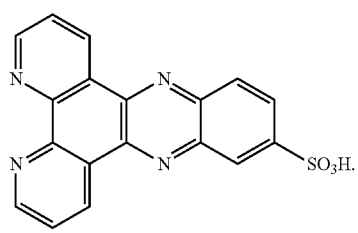 [SMILES: O=C(O)c1ccc2nc3c4cccnc4c4ncccc4c3nc2c1]

For the purposes of the present invention the term "HAT" will stand equally well for

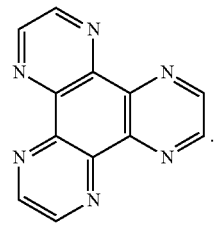 [SMILES: c1cnc2c(n1)c1nccnc1c1nccnc21]

For the purposes of the present invention the term "TAP" will stand equally well for

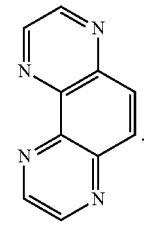

For the purposes of the present invention the term "PHE-HAT" will stand equally well for

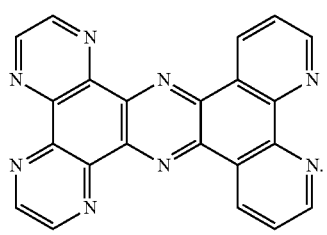 [SMILES: c1cnc2c(c1)c1nc3c4nccnc4c4nccnc4c3nc1c1cccnc12]

For the purposes of the present invention the term "tpac" will stand equally well for

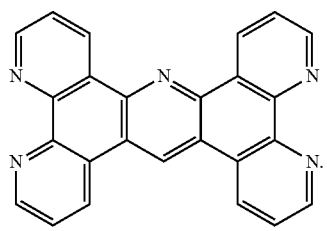 [SMILES: c1cnc2c(c1)c1cc3c4cccnc4c4ncccc4c3nc1c1cccnc12]

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^6)_2$, each $R^6$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

As used herein, the term "photodynamic therapy" shall mean a treatment for destroying cells or modulating immune function, including immune response, of cells and tissue through use of a drug that can be activated by light of a certain wavelength and dose.

As used herein, the term "photodynamic compound" shall mean a compound that provides photodynamic therapy.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

Compounds

The compounds of the present invention are metal-based coordination compounds derived from organic ligands chelated to a metal, are preferably tunable photodynamic compounds, and include all enantiomeric and diastereomeric forms and pharmaceutically accepted salts thereof having the formula (I),

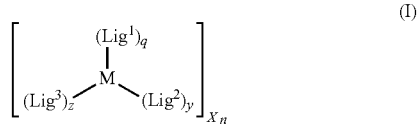

including hydrates, solvates, pharmaceutically acceptable salts, prodrugs and complexes thereof, wherein:

M at each occurrence is independently selected from the group consisting of osmium, manganese, molybdenum, rhenium, ruthenium, iron, cobalt, rhodium, iridium, nickel, platinum, palladium, vanadium, chromium, tungsten, technetium, and copper;

X is selected from the group consisting of $Cl^-$, $PF_6^-$, $Br^-$, $BF_4^-$, $ClO_4^-$, $CF_3SO_3^-$, and $SO_4^{-2}$;

n=0, 1, 2, 3, 4, or 5;

q is independently at each occurrence 0, 1, or 2;

y is independently at each occurrence 0, 1, or 2;

z is independently at each occurrence 1, 2, or 3;

$Lig^1$ is a bidentate ligand that at each occurrence at each occurrence is each independently selected from the group consisting of

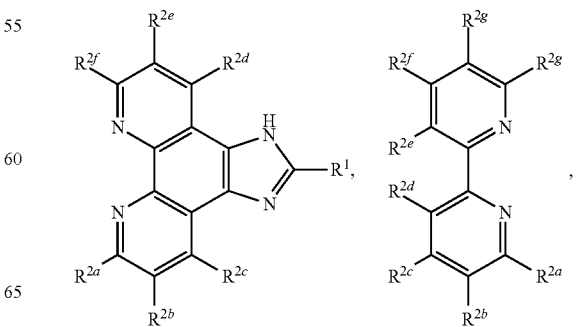

-continued
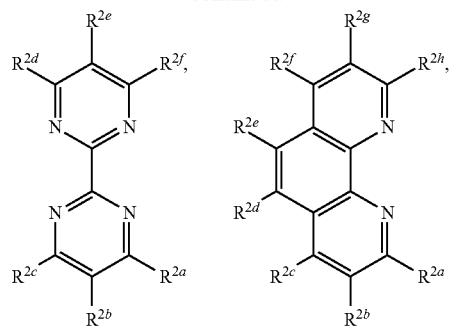
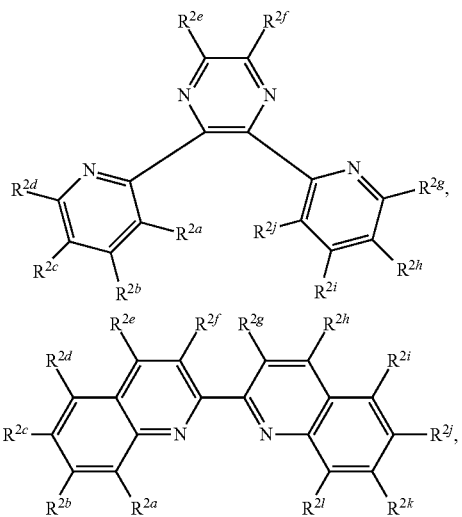
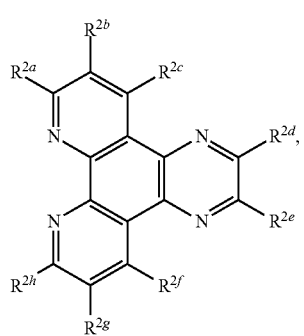
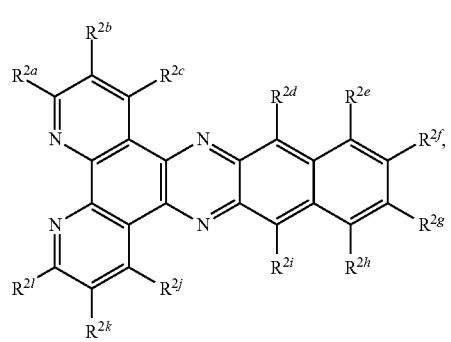
-continued
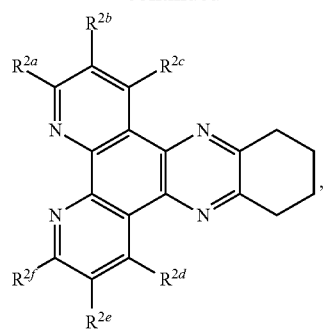
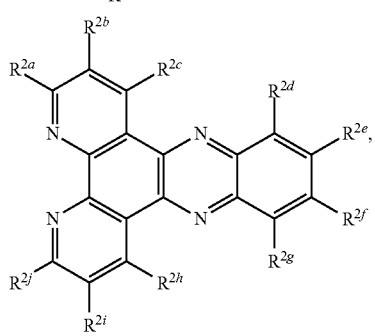
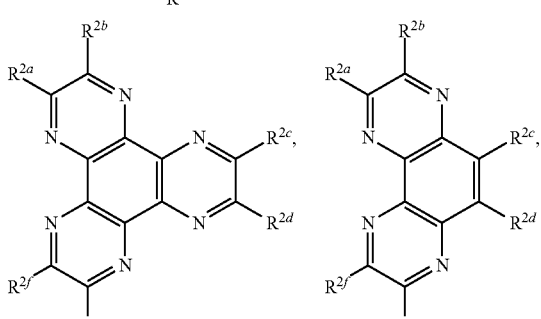
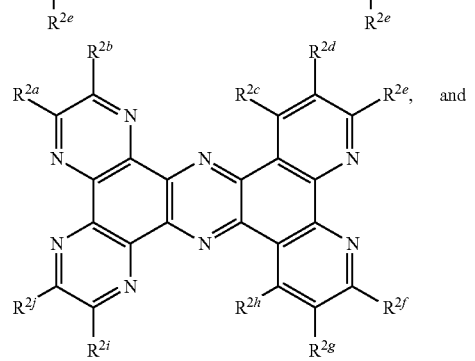
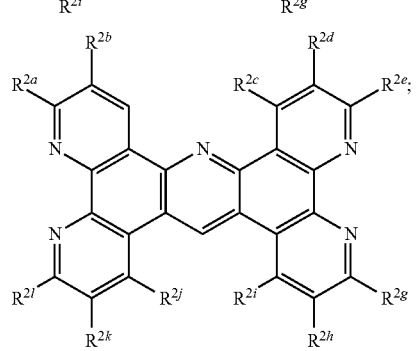
$Lig^2$ is a bidentate ligand that at each occurrence is each independently selected from the group consisting of

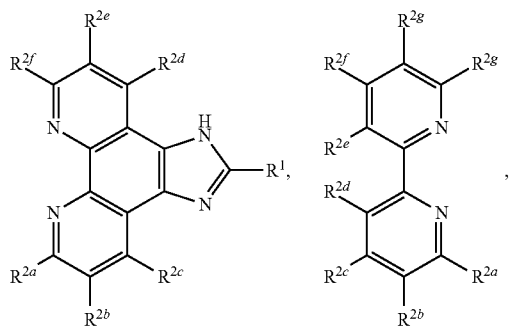
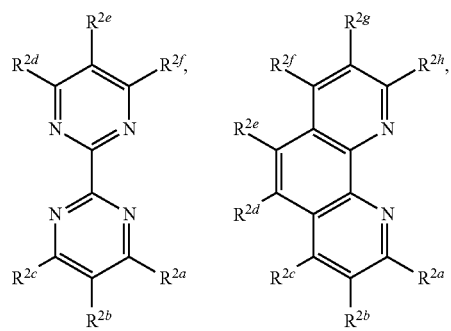
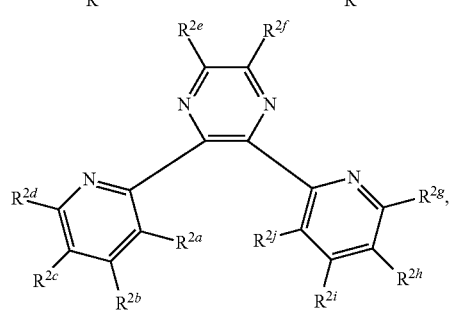
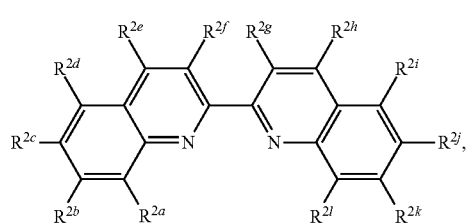
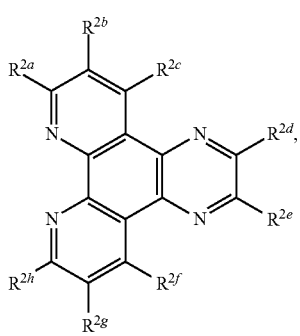
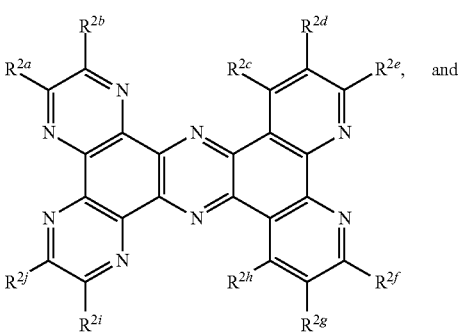

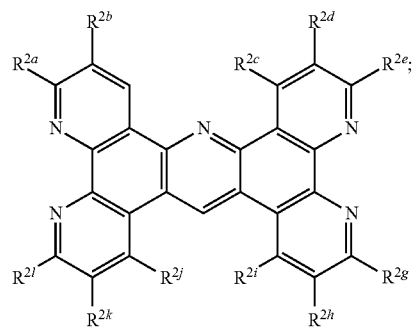
Lig³ is a bidentate ligand that at each occurrence is each independently selected from the group consisting of
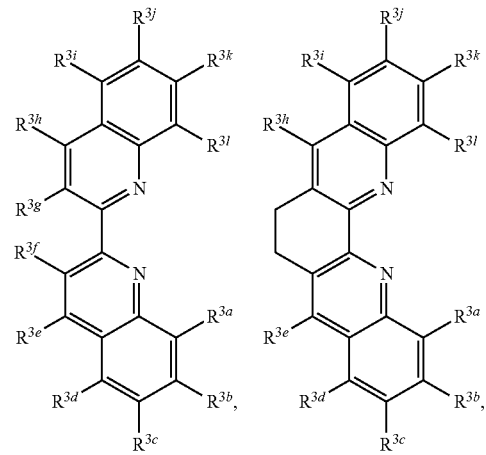
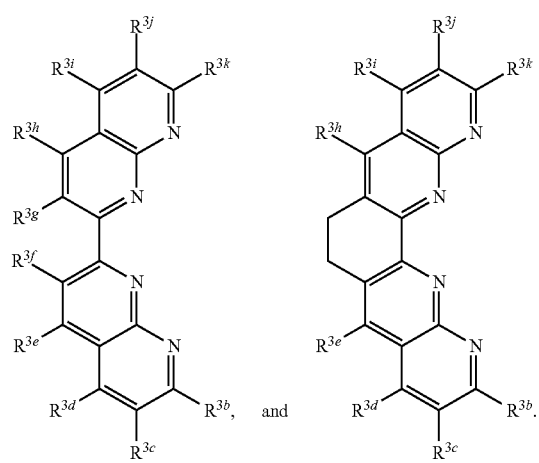
R¹ is selected from the group consisting of hydrogen, optionally substituted phenyl, optionally substituted aryl, optionally substituted heteroaryl, 4-pyridyl, 3-pyridyl, 2-thiazole, 2-pyrrolyl, 2-furanyl,
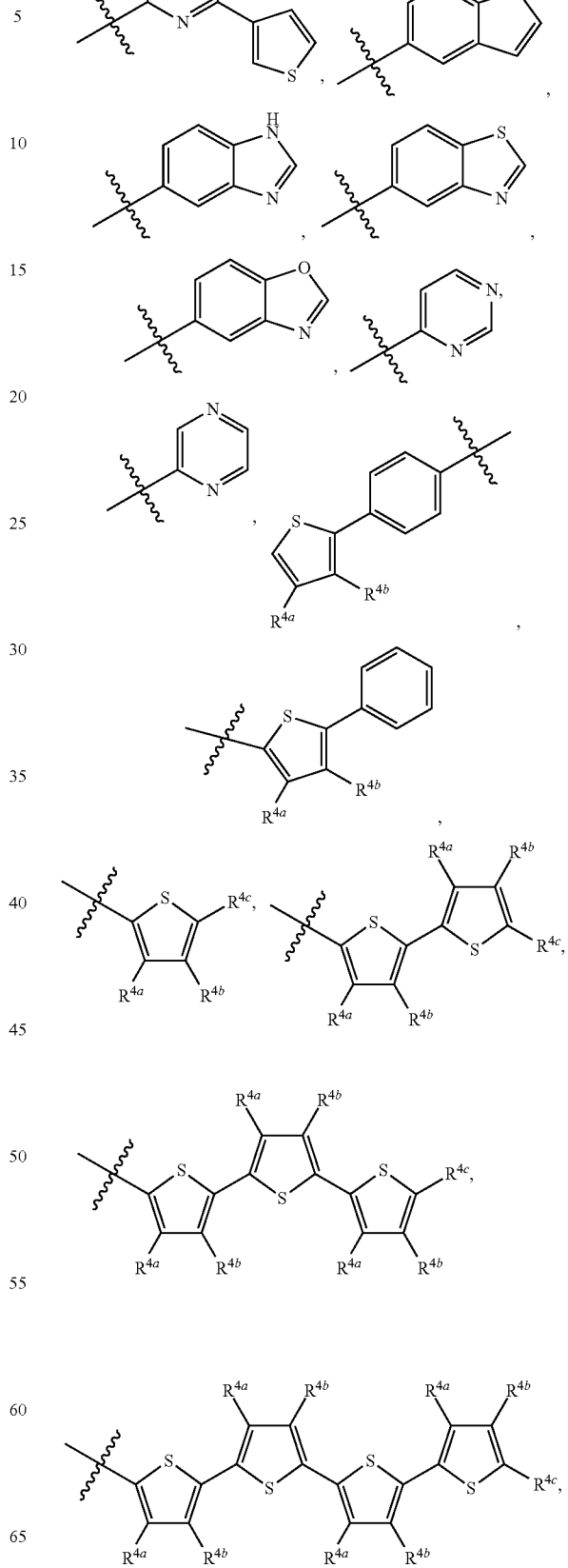

-continued

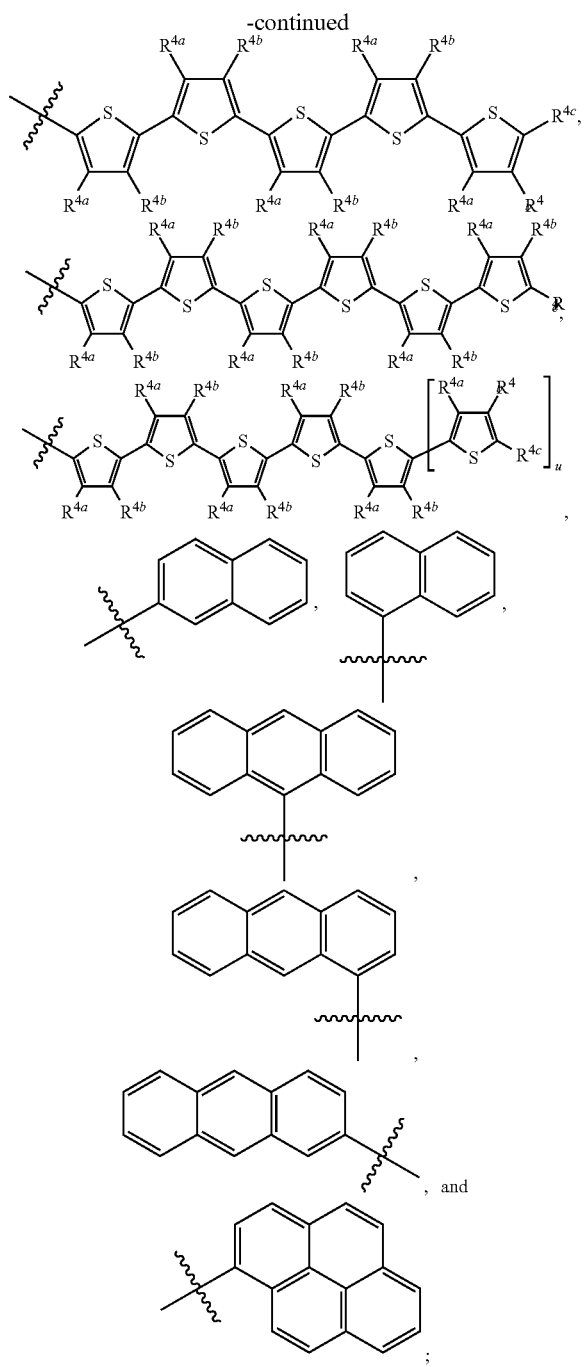

u is an integer;
$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;
$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;
$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;
$R^{4a}$ and $R^{4b}$ at each occurrence on a thiophene ring are taken together with the atom to which they are bound to form an optionally substituted ring having from 6 ring atoms containing 2 oxygen atoms;
$R^5$ at each occurrence are each independently selected from the group consisting of hydrogen and optionally substituted alkyl;
$R^6$ at each occurrence are each independently selected from the group consisting of hydrogen and optionally substituted alkyl;
$R^7$ at each occurrence are each independently selected from the group consisting of hydrogen and optionally substituted alkyl;
$R^8$ at each occurrence are each independently selected from the group consisting of hydrogen and optionally substituted alkyl;

The compounds of the present invention includes compounds having formula (II),

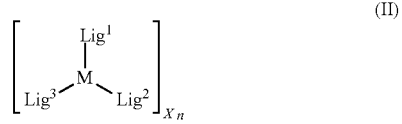

(II)

including hydrates, solvates, pharmaceutically acceptable salts, prodrugs and complexes thereof.

The compounds of the present invention includes compounds having formula (III):

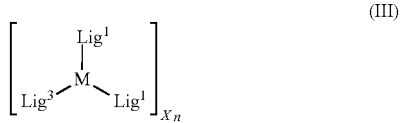

(III)

including hydrates, solvates, pharmaceutically acceptable salts, prodrugs and complexes thereof.

The compounds of the present invention includes compounds having formula (IV):

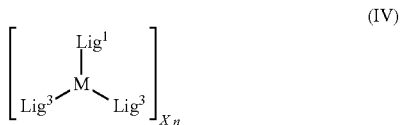

(IV)

including hydrates, solvates, pharmaceutically acceptable salts, prodrugs and complexes thereof.

The present invention is also directed toward novel compounds of formula (V):

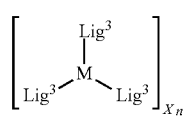

(V)

including hydrates, solvates, pharmaceutically acceptable salts, prodrugs and complexes thereof.

The present invention is also directed toward novel compounds of formula (VI):

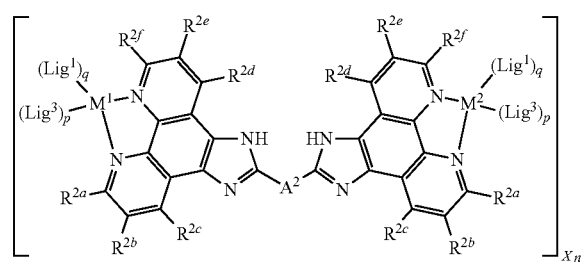

(VI)

including hydrates, solvates, pharmaceutically acceptable salts, prodrugs and complexes thereof wherein:

$A^2$ is selected from the group consisting of

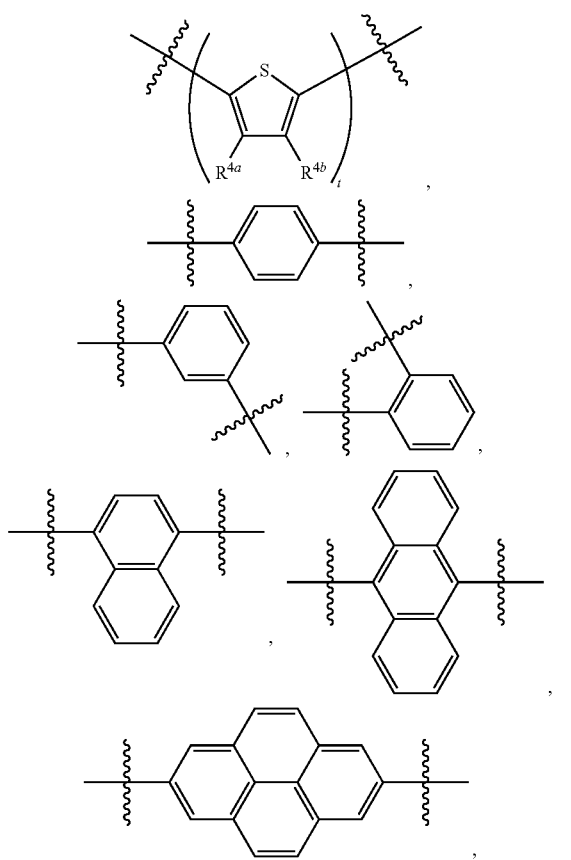

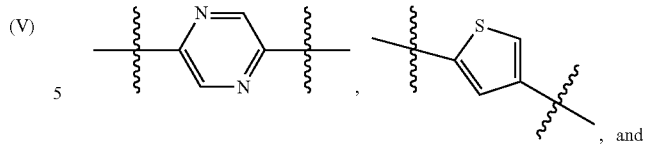

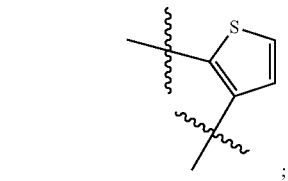

$t$ is an integer.

The present invention is also directed toward novel compounds of formula (VIIa):

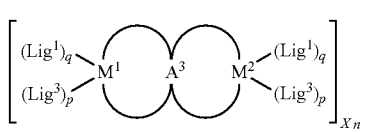

(VIIa)

including hydrates, solvates, pharmaceutically acceptable salts, prodrugs and complexes thereof wherein:

$A^3$ is selected from the group consisting of

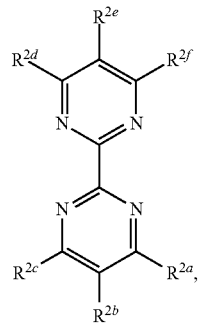

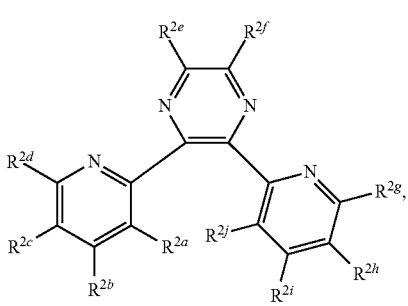

-continued

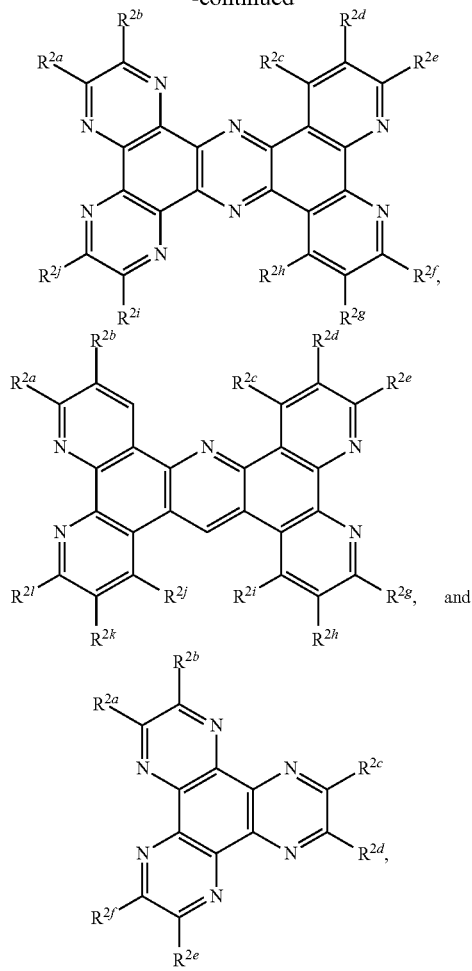

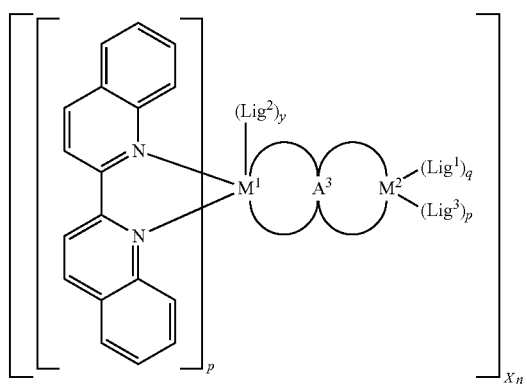

Wherein $A^3$ is a bridging ligand bound to $M^1$ as a bidentate ligand and $A^3$ is bound to $M^2$ as a bidentate ligand.

The present invention is also directed toward novel compounds of formula (VIIb):

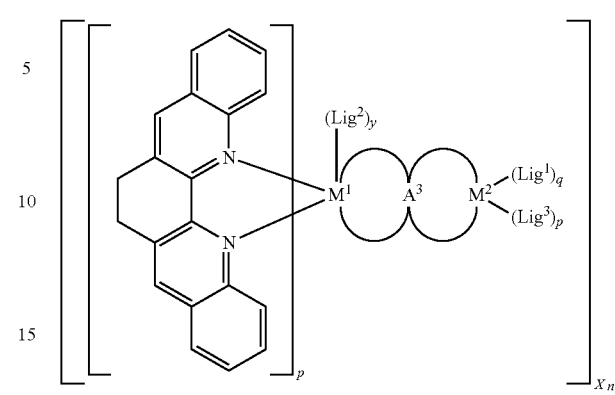
(VIIb)

including hydrates, solvates, pharmaceutically acceptable salts, prodrugs and complexes thereof.

The present invention is also directed toward novel compounds of formula (VIIc):

(VIIc)

including hydrates, solvates, pharmaceutically acceptable salts, prodrugs and complexes thereof.

The present invention is also directed toward novel compounds of formula (VIId):

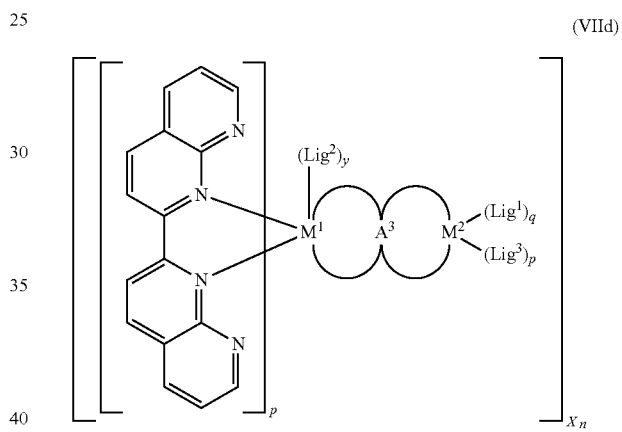
(VIId)

including hydrates, solvates, pharmaceutically acceptable salts, prodrugs and complexes thereof.

The present invention is also directed toward novel compounds of formula (VIIe):

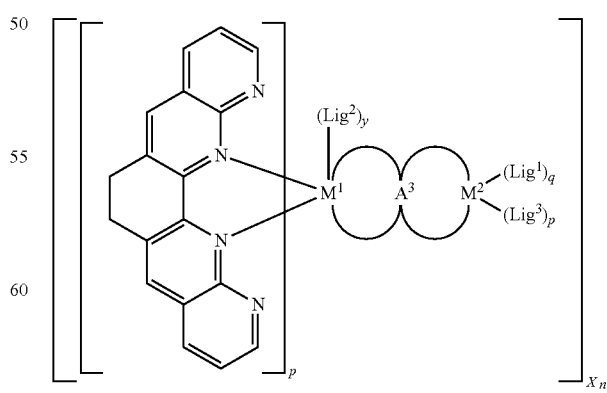
(VIIe)

including hydrates, solvates, pharmaceutically acceptable salts, prodrugs and complexes thereof.

The present invention is also directed toward novel compounds of formula (VIIf):

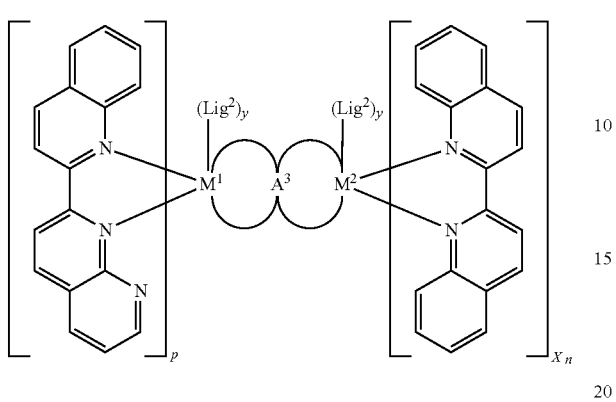

including hydrates, solvates, pharmaceutically acceptable salts, prodrugs and complexes thereof.

In some embodiments M is osmium, manganese, molybdenum, rhenium, ruthenium, iron, cobalt, rhodium, iridium, nickel, platinum, palladium, vanadium, chromium, tungsten, technetium, or copper.

In some embodiments $M^1$ is osmium, manganese, molybdenum, rhenium, ruthenium, iron, cobalt, rhodium, iridium, nickel, platinum, palladium, vanadium, chromium, tungsten, technetium, or copper.

In some embodiments $M^2$ is osmium, manganese, molybdenum, rhenium, ruthenium, iron, cobalt, rhodium, iridium, nickel, platinum, palladium, vanadium, chromium, tungsten, technetium, or copper.

In some embodiments X is $Cl^-$, $PF_6^-$, $Br^-$, $BF_4^-$, $ClO_4^-$, $CF_3SO_3^-$, or $SO_4^{-2}$.

In some embodiments n is 0.
In some embodiments n is 1.
In some embodiments n is 2.
In some embodiments n is 3.
In some embodiments n is 4.
In some embodiments n is 5.
In some embodiments y is 0.
In some embodiments y is 1.
In some embodiments y is 2.
In some embodiments z is 1.
In some embodiments z is 2.
In some embodiments z is 3.
In some embodiments q is 0.
In some embodiments q is 1.
In some embodiments q is 2.
In some embodiments $Lig^1$ is

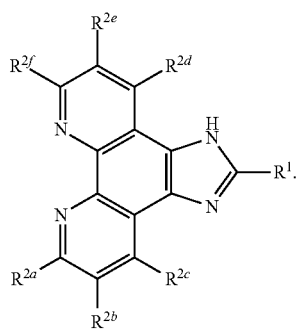

In some embodiments $Lig^1$ is

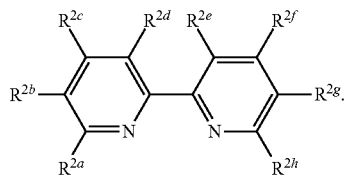

In some embodiments $Lig^1$ is

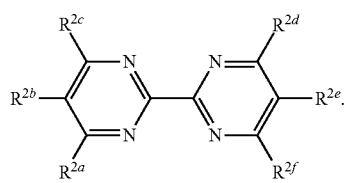

In some embodiments $Lig^1$ is

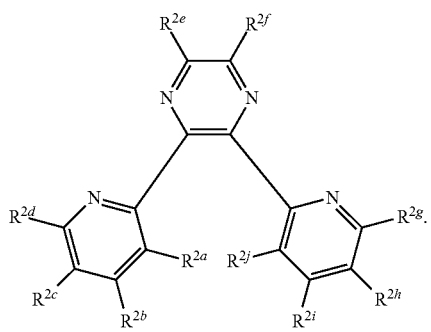

In some embodiments $Lig^1$ is

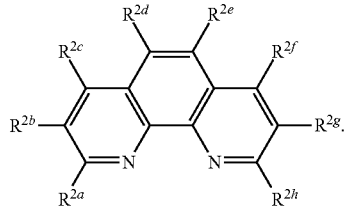

In some embodiments $Lig^1$ is

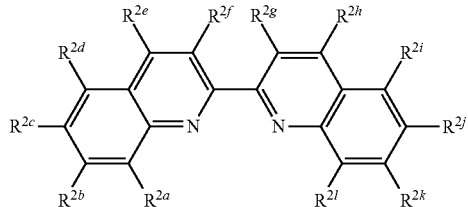

In some embodiments Lig¹ is
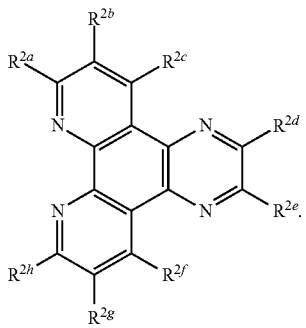
In some embodiments Lig¹ is
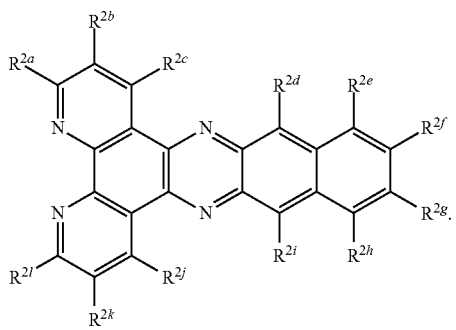
In some embodiments Lig¹ is
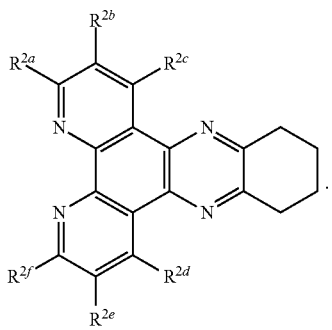
In some embodiments Lig¹ is
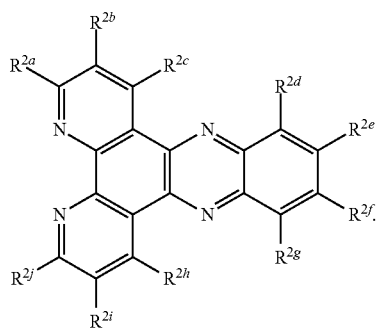
In some embodiments Lig¹ is
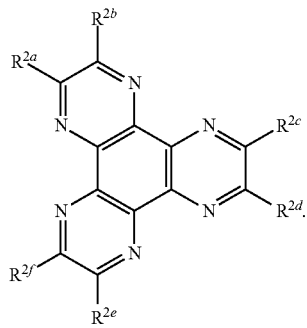
In some embodiments Lig¹ is
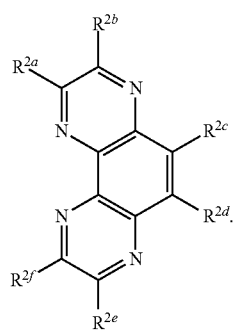
In some embodiments Lig¹ is
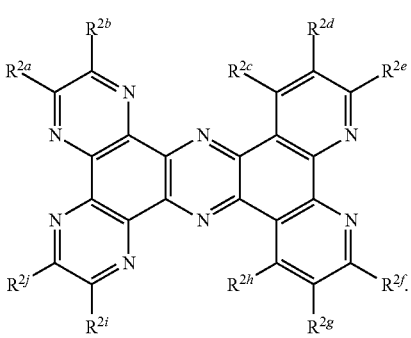
In some embodiments Lig¹ is
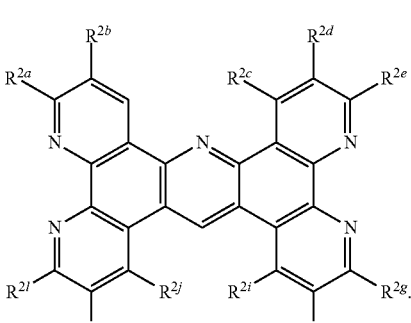

In some embodiments Lig² is
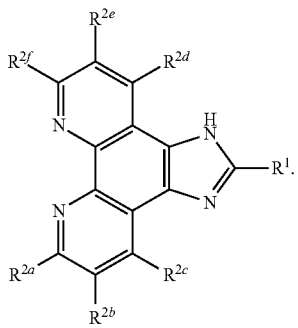
In some embodiments Lig² is
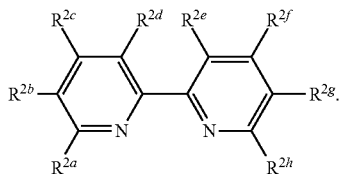
In some embodiments Lig² is
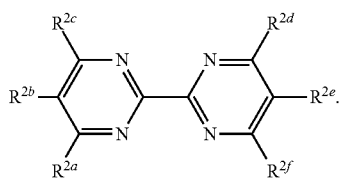
In some embodiments Lig² is
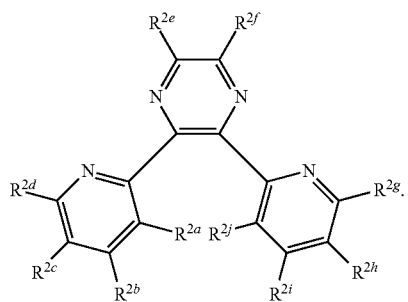
In some embodiments Lig² is
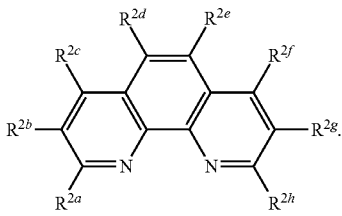
In some embodiments Lig² is
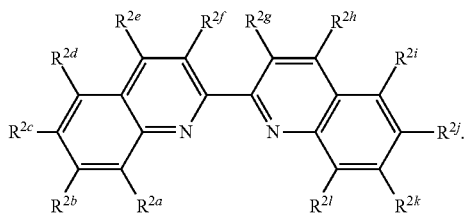
In some embodiments Lig² is
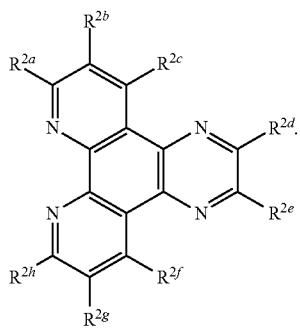
In some embodiments Lig² is
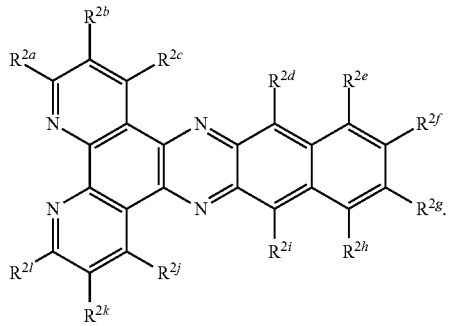
In some embodiments Lig² is
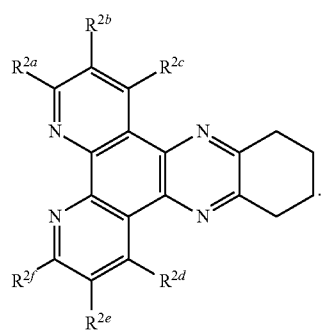

In some embodiments Lig² is
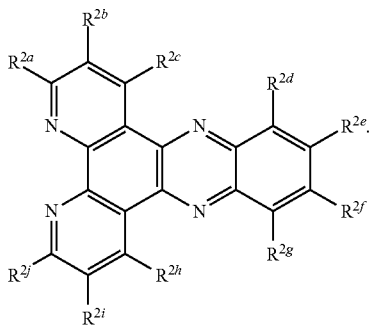
In some embodiments Lig² is
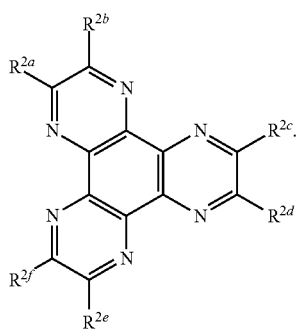
In some embodiments Lig² is
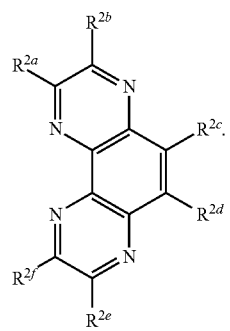
In some embodiments Lig² is
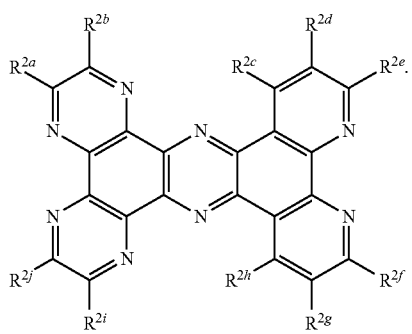
In some embodiments Lig² is
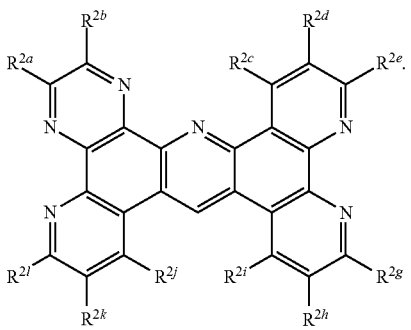
In some embodiments Lig³ is
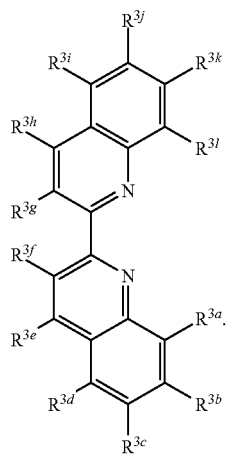
In some embodiments Lig³ is
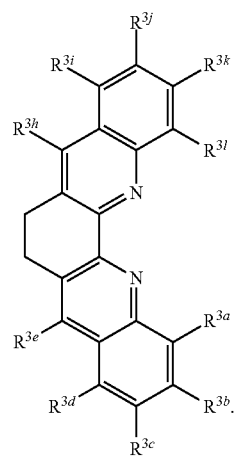

In some embodiments Lig³ is

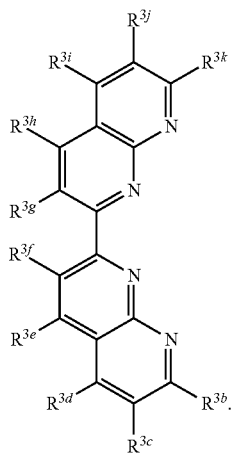

In some embodiments Lig³ is

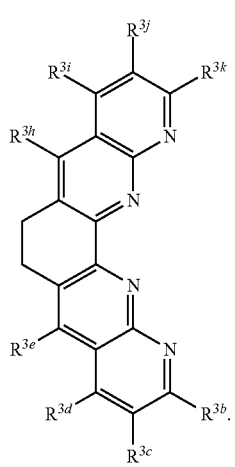

In some embodiments R¹ is hydrogen.
In some embodiments R¹ is optionally substituted phenyl.
In some embodiments R¹ is optionally substituted aryl.
In some embodiments R¹ is optionally substituted heteroaryl.
In some embodiments R¹ is 2-furanyl.
In some embodiments R¹ is 3-pyridyl.
In some embodiments R¹ is 4-pyridyl
In some embodiments R¹ is 2-thiazole
In some embodiments R¹ is 2-pyrolyl
In some embodiments R¹ is

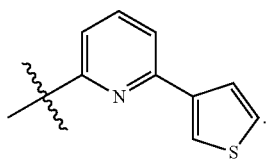 [SMILES: *c1cccc(-c2ccsc2)n1]

In some embodiments R¹ is

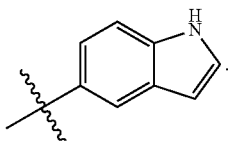 [SMILES: *c1ccc2[nH]ccc2c1]

In some embodiments R¹ is

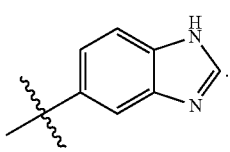 [SMILES: *c1ccc2[nH]cnc2c1]

In some embodiments R¹ is

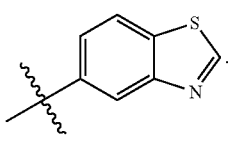 [SMILES: *c1ccc2scnc2c1]

In some embodiments R¹ is

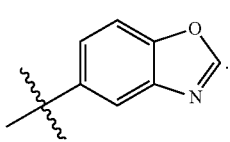 [SMILES: *c1ccc2ocnc2c1]

In some embodiments R¹ is

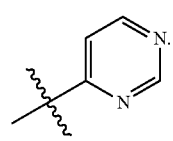 [SMILES: *c1ccncn1]

In some embodiments R¹ is

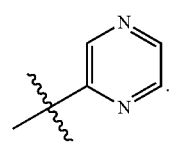 [SMILES: *c1cnccn1]

In some embodiments R¹ is
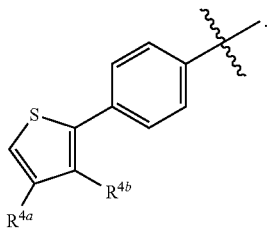
In some embodiments R¹ is
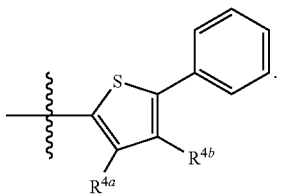
In some embodiments R¹ is
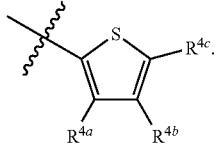
In some embodiments R¹ is
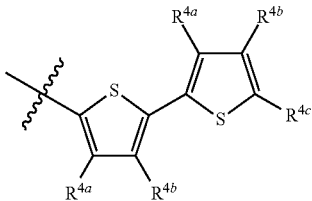
In some embodiments R¹ is
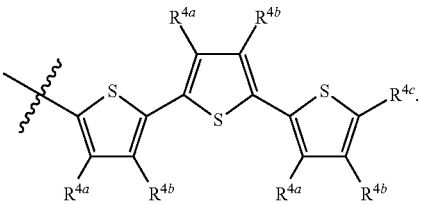
In some embodiments R¹ is
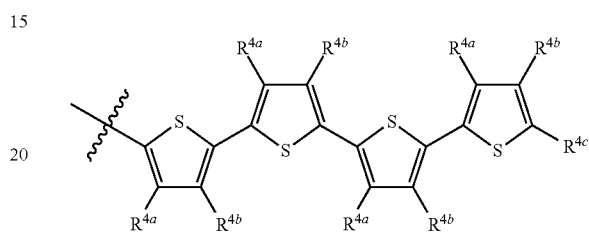
In some embodiments R¹ is
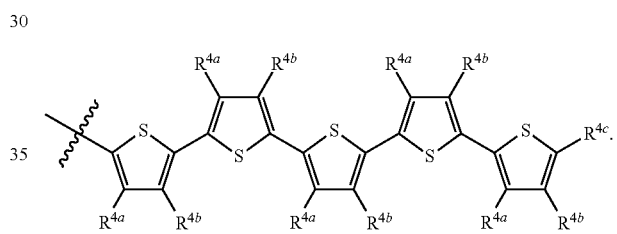
In some embodiments R¹ is
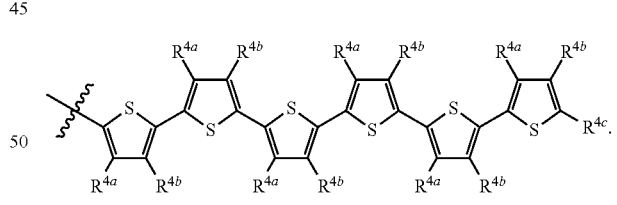
In some embodiments, R¹ is
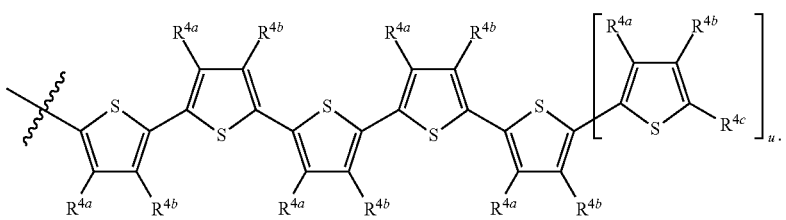
In some embodiments u is an integer.

In some embodiments, R¹ is
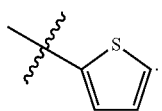 [SMILES: *c1cccs1]
In some embodiments, R¹ is
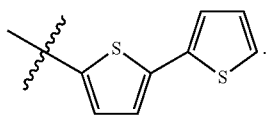 [SMILES: *c1ccc(-c2cccs2)s1]
In some embodiments, R¹ is
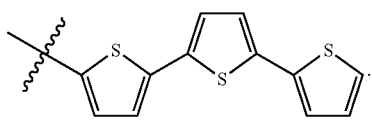 [SMILES: *c1ccc(-c2ccc(-c3cccs3)s2)s1]
In some embodiments, R¹ is
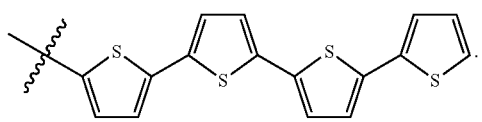 [SMILES: *c1ccc(-c2ccc(-c3ccc(-c4cccs4)s3)s2)s1]
In some embodiments, R¹ is
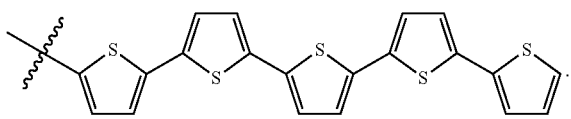 [SMILES: *c1ccc(-c2ccc(-c3ccc(-c4ccc(-c5cccs5)s4)s3)s2)s1]
In some embodiments, R¹ is
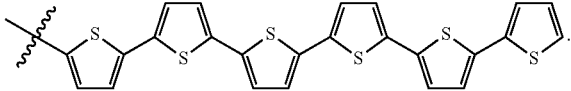 [SMILES: *c1ccc(-c2ccc(-c3ccc(-c4ccc(-c5ccc(-c6cccs6)s5)s4)s3)s2)s1]
In some embodiments R¹ is
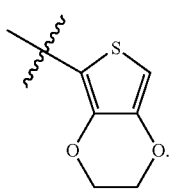 [SMILES: *c1scc2c1OCCO2]
In some embodiments R¹ is
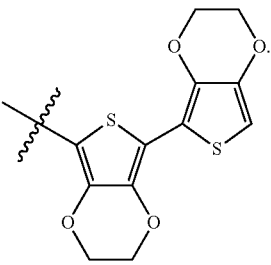 [SMILES: *c1sc(-c2scc3c2OCCO3)c2c1OCCO2]
In some embodiments R¹ is
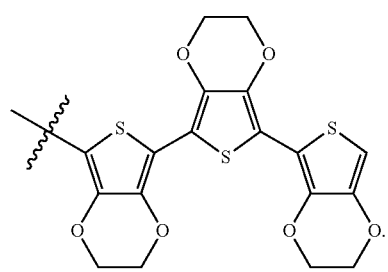 [SMILES: *c1sc(-c2sc(-c3scc4c3OCCO4)c3c2OCCO3)c2c1OCCO2]
In some embodiments R¹ is
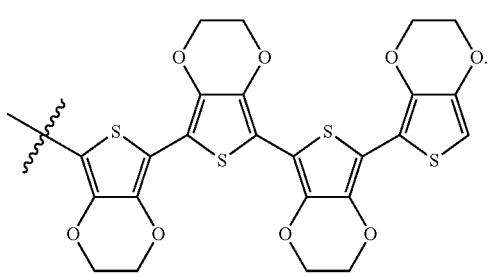 [SMILES: *c1sc(-c2sc(-c3sc(-c4scc5c4OCCO5)c4c3OCCO4)c3c2OCCO3)c2c1OCCO2]
In some embodiments R¹ is
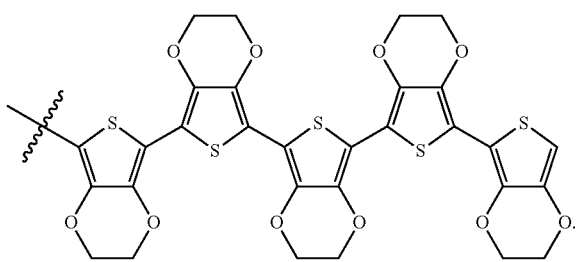 [SMILES: *c1sc(-c2sc(-c3sc(-c4sc(-c5scc6c5OCCO6)c5c4OCCO5)c4c3OCCO4)c3c2OCCO3)c2c1OCCO2]
In some embodiments R¹ is
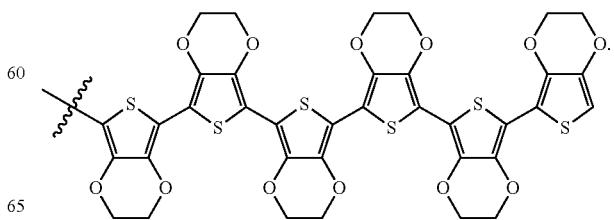

In some embodiments $R^1$ is

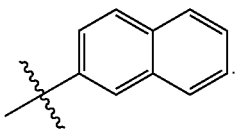

In some embodiments $R^1$ is

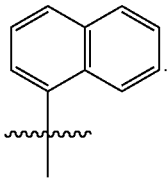 [SMILES: *c1cccc2ccccc12]

In some embodiments $R^1$ is

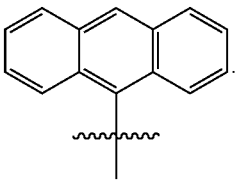 [SMILES: *c1c2ccccc2cc2ccccc12]

In some embodiments $R^1$ is

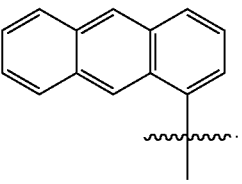 [SMILES: *c1cccc2cc3ccccc3cc12]

In some embodiments $R^1$ is

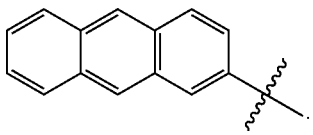 [SMILES: *c1ccc2cc3ccccc3cc2c1]

In some embodiments $R^1$ is

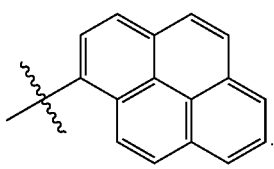 [SMILES: *c1ccc2ccc3cccc4ccc1c2c34]

In some embodiments $R^{2a}$ is hydrogen.
In some embodiments $R^{2a}$ is $C_{1-6}$ optionally substituted alkyl.
In some embodiments $R^{2a}$ is $C_{1-6}$ optionally substituted branched alkyl.
In some embodiments $R^{2a}$ is $C_{3-7}$ optionally substituted cycloalkyl.
In some embodiments $R^{2a}$ is $C_{1-6}$ optionally substituted haloalkyl.
In some embodiments $R^{2a}$ is $C_{1-6}$ optionally substituted alkoxy.
In some embodiments $R^{2a}$ is $CO_2R^5$.
In some embodiments $R^{2a}$ is $CONR^6_2$.
In some embodiments $R^{2a}$ is $NR^7_2$.
In some embodiments $R^{2a}$ is $SO_3H$.
In some embodiments $R^{2a}$ is sulfate.
In some embodiments $R^{2a}$ is sulfonate.
In some embodiments $R^{2a}$ is optionally substituted aryl.
In some embodiments $R^{2a}$ is optionally substituted aryloxy.
In some embodiments $R^{2a}$ is optionally substituted heteroaryl.
In some embodiments $R^{2a}$ is optionally substituted heterocycle.
In some embodiments $R^{2b}$ is hydrogen.
In some embodiments $R^{2b}$ is $C_{1-6}$ optionally substituted alkyl.
In some embodiments $R^{2b}$ is $C_{1-6}$ optionally substituted branched alkyl.
In some embodiments $R^{2b}$ is $C_{3-7}$ optionally substituted cycloalkyl.
In some embodiments $R^{2b}$ is $C_{1-6}$ optionally substituted haloalkyl.
In some embodiments $R^{2b}$ is $C_{1-6}$ optionally substituted alkoxy.
In some embodiments $R^{2b}$ is $CO_2R^5$.
In some embodiments $R^{2b}$ is $CONR^6_2$.
In some embodiments $R^{2b}$ is $NR^7_2$.
In some embodiments $R^{2b}$ is $SO_3H$.
In some embodiments $R^{2b}$ is sulfate.
In some embodiments $R^{2b}$ is sulfonate.
In some embodiments $R^{2b}$ is optionally substituted aryl.
In some embodiments $R^{2b}$ is optionally substituted aryloxy.
In some embodiments $R^{2b}$ is optionally substituted heteroaryl.
In some embodiments $R^{2b}$ is optionally substituted heterocycle.
In some embodiments $R^{2c}$ is hydrogen.
In some embodiments $R^{2c}$ is $C_{1-6}$ optionally substituted alkyl.
In some embodiments $R^{2c}$ is $C_{1-6}$ optionally substituted branched alkyl.
In some embodiments $R^{2c}$ is $C_{3-7}$ optionally substituted cycloalkyl.
In some embodiments $R^{2c}$ is $C_{1-6}$ optionally substituted haloalkyl.
In some embodiments $R^{2c}$ is $C_{1-6}$ optionally substituted alkoxy.
In some embodiments $R^{2c}$ is $CO_2R^5$.
In some embodiments $R^{2c}$ is $CONR^6_2$.
In some embodiments $R^{2c}$ is $NR^7_2$.
In some embodiments $R^{2c}$ is $SO_3H$.
In some embodiments $R^{2c}$ is sulfate.
In some embodiments $R^{2c}$ is sulfonate.
In some embodiments $R^{2c}$ is optionally substituted aryl.
In some embodiments $R^{2c}$ is optionally substituted aryloxy.
In some embodiments $R^{2c}$ is optionally substituted heteroaryl.
In some embodiments $R^{2c}$ is optionally substituted heterocycle.

In some embodiments $R^{2d}$ is hydrogen.
In some embodiments $R^{2d}$ is $C_{1-6}$ optionally substituted alkyl.
In some embodiments $R^{2d}$ is $C_{1-6}$ optionally substituted branched alkyl.
In some embodiments $R^{2d}$ is $C_{3-7}$ optionally substituted cycloalkyl.
In some embodiments $R^{2d}$ is $C_{1-6}$ optionally substituted haloalkyl.
In some embodiments $R^{2d}$ is $C_{1-6}$ optionally substituted alkoxy.
In some embodiments $R^{2d}$ is $CO_2R^5$.
In some embodiments $R^{2d}$ is $CONR^6{}_2$.
In some embodiments $R^{2d}$ is $NR^7{}_2$.
In some embodiments $R^{2d}$ is $SO_3H$.
In some embodiments $R^{2d}$ is sulfate.
In some embodiments $R^{2d}$ is sulfonate.
In some embodiments $R^{2d}$ is optionally substituted aryl.
In some embodiments $R^{2d}$ is optionally substituted aryloxy.
In some embodiments $R^{2d}$ is optionally substituted heteroaryl.
In some embodiments $R^{2d}$ is optionally substituted heterocycle.
In some embodiments $R^{2e}$ is hydrogen.
In some embodiments $R^{2e}$ is $C_{1-6}$ optionally substituted alkyl.
In some embodiments $R^{2e}$ is $C_{1-6}$ optionally substituted branched alkyl.
In some embodiments $R^{2e}$ is $C_{3-7}$ optionally substituted cycloalkyl.
In some embodiments $R^{2e}$ is $C_{1-6}$ optionally substituted haloalkyl.
In some embodiments $R^{2e}$ is $C_{1-6}$ optionally substituted alkoxy.
In some embodiments $R^{2e}$ is $CO_2R^5$.
In some embodiments $R^{2e}$ is $CONR^6{}_2$.
In some embodiments $R^{2e}$ is $NR^7{}_2$.
In some embodiments $R^{2e}$ is $SO_3H$.
In some embodiments $R^{2e}$ is sulfate.
In some embodiments $R^{2e}$ is sulfonate.
In some embodiments $R^{2e}$ is optionally substituted aryl.
In some embodiments $R^{2e}$ is optionally substituted aryloxy.
In some embodiments $R^{2e}$ is optionally substituted heteroaryl.
In some embodiments $R^{2e}$ is optionally substituted heterocycle.
In some embodiments $R^{2f}$ is hydrogen.
In some embodiments $R^{2f}$ is $C_{1-6}$ optionally substituted alkyl.
In some embodiments $R^{2f}$ is $C_{1-6}$ optionally substituted branched alkyl.
In some embodiments $R^{2f}$ is $C_{3-7}$ optionally substituted cycloalkyl.
In some embodiments $R^{2f}$ is $C_{1-6}$ optionally substituted haloalkyl.
In some embodiments $R^{2f}$ is $C_{1-6}$ optionally substituted alkoxy.
In some embodiments $R^{2f}$ is $CO_2R^5$.
In some embodiments $R^{2f}$ is $CONR^6{}_2$.
In some embodiments $R^{2f}$ is $NR^7{}_2$.
In some embodiments $R^{2f}$ is $SO_3H$.
In some embodiments $R^{2f}$ is sulfate.
In some embodiments $R^{2f}$ is sulfonate.
In some embodiments $R^{2f}$ is optionally substituted aryl.
In some embodiments $R^{2f}$ is optionally substituted aryloxy.
In some embodiments $R^{2f}$ is optionally substituted heteroaryl.
In some embodiments $R^{2f}$ is optionally substituted heterocycle.
In some embodiments $R^{2g}$ is hydrogen.
In some embodiments $R^{2g}$ is $C_{1-6}$ optionally substituted alkyl.
In some embodiments $R^{2g}$ is $C_{1-6}$ optionally substituted branched alkyl.
In some embodiments $R^{2g}$ is $C_{3-7}$ optionally substituted cycloalkyl.
In some embodiments $R^{2g}$ is $C_{1-6}$ optionally substituted haloalkyl.
In some embodiments $R^{2g}$ is $C_{1-6}$ optionally substituted alkoxy.
In some embodiments $R^{2g}$ is $CO_2R^5$.
In some embodiments $R^{2g}$ is $CONR^6{}_2$.
In some embodiments $R^{2g}$ is $NR^7{}_2$.
In some embodiments $R^{2g}$ is $SO_3H$.
In some embodiments $R^{2g}$ is sulfate.
In some embodiments $R^{2g}$ is sulfonate.
In some embodiments $R^{2g}$ is optionally substituted aryl.
In some embodiments $R^{2g}$ is optionally substituted aryloxy.
In some embodiments $R^{2g}$ is optionally substituted heteroaryl.
In some embodiments $R^{2g}$ is optionally substituted heterocycle.
In some embodiments $R^{2h}$ is hydrogen.
In some embodiments $R^{2h}$ is $C_{1-6}$ optionally substituted alkyl.
In some embodiments $R^{2h}$ is $C_{1-6}$ optionally substituted branched alkyl.
In some embodiments $R^{2h}$ is $C_{3-7}$ optionally substituted cycloalkyl.
In some embodiments $R^{2h}$ is $C_{1-6}$ optionally substituted haloalkyl.
In some embodiments $R^{2h}$ is $C_{1-6}$ optionally substituted alkoxy.
In some embodiments $R^{2h}$ is $CO_2R^5$.
In some embodiments $R^{2h}$ is $CONR^6{}_2$.
In some embodiments $R^{2h}$ is $NR^7{}_2$.
In some embodiments $R^{2h}$ is $SO_3H$.
In some embodiments $R^{2h}$ is sulfate.
In some embodiments $R^{2h}$ is sulfonate.
In some embodiments $R^{2h}$ is optionally substituted aryl.
In some embodiments $R^{2h}$ is optionally substituted aryloxy.
In some embodiments $R^{2h}$ is optionally substituted heteroaryl.
In some embodiments $R^{2h}$ is optionally substituted heterocycle.
In some embodiments $R^{2f}$ is hydrogen.
In some embodiments $R^{2i}$ is $C_{1-6}$ optionally substituted alkyl.
In some embodiments $R^{2i}$ is $C_{1-6}$ optionally substituted branched alkyl.
In some embodiments $R^{2i}$ is $C_{3-7}$ optionally substituted cycloalkyl.
In some embodiments $R^{2i}$ is $C_{1-6}$ optionally substituted haloalkyl.
In some embodiments $R^{2i}$ is $C_{1-6}$ optionally substituted alkoxy.
In some embodiments $R^{2i}$ is $CO_2R^5$.
In some embodiments $R^{2i}$ is $CONR^6{}_2$.

In some embodiments $R^{2i}$ is $NR^7{}_2$.
In some embodiments $R^{2i}$ is $SO_3H$.
In some embodiments $R^{2i}$ is sulfate.
In some embodiments $R^{2i}$ is sulfonate.
In some embodiments $R^{2i}$ is optionally substituted aryl.
In some embodiments $R^{2i}$ is optionally substituted aryloxy.
In some embodiments $R^{2i}$ is optionally substituted heteroaryl.
In some embodiments $R^{2i}$ is optionally substituted heterocycle.
In some embodiments $R^{2j}$ is hydrogen.
In some embodiments $R^{2j}$ is $C_{1-6}$ optionally substituted alkyl.
In some embodiments $R^{2j}$ is $C_{1-6}$ optionally substituted branched alkyl.
In some embodiments $R^{2j}$ is $C_{3-7}$ optionally substituted cycloalkyl.
In some embodiments $R^{2j}$ is $C_{1-6}$ optionally substituted haloalkyl.
In some embodiments $R^{2j}$ is $C_{1-6}$ optionally substituted alkoxy.
In some embodiments $R^{2j}$ is $CO_2R^5$.
In some embodiments $R^{2j}$ is $CONR^6{}_2$.
In some embodiments $R^{2j}$ is $NR^7{}_2$.
In some embodiments $R^{2j}$ is $SO_3H$.
In some embodiments $R^{2j}$ is sulfate.
In some embodiments $R^{2j}$ is sulfonate.
In some embodiments $R^{2j}$ is optionally substituted aryl.
In some embodiments $R^{2j}$ is optionally substituted aryloxy.
In some embodiments $R^{2j}$ is optionally substituted heteroaryl.
In some embodiments $R^{2j}$ is optionally substituted heterocycle.
In some embodiments $R^{2k}$ is hydrogen.
In some embodiments $R^{2k}$ is $C_{1-6}$ optionally substituted alkyl.
In some embodiments $R^{2k}$ is $C_{1-6}$ optionally substituted branched alkyl.
In some embodiments $R^{2k}$ is $C_{3-7}$ optionally substituted cycloalkyl.
In some embodiments $R^{2k}$ is $C_{1-6}$ optionally substituted haloalkyl.
In some embodiments $R^{2k}$ is $C_{1-6}$ optionally substituted alkoxy.
In some embodiments $R^{2k}$ is $CO_2R^5$.
In some embodiments $R^{2k}$ is $CONR^6{}_2$.
In some embodiments $R^{2k}$ is $NR^7{}_2$.
In some embodiments $R^{2k}$ is $SO_3H$.
In some embodiments $R^{2k}$ is sulfate.
In some embodiments $R^{2k}$ is sulfonate.
In some embodiments $R^{2k}$ is optionally substituted aryl.
In some embodiments $R^{2k}$ is optionally substituted aryloxy.
In some embodiments $R^{2k}$ is optionally substituted heteroaryl.
In some embodiments $R^{2k}$ is optionally substituted heterocycle.
In some embodiments $R^{2l}$ is hydrogen.
In some embodiments $R^{2l}$ is $C_{1-6}$ optionally substituted alkyl.
In some embodiments $R^{2l}$ is $C_{1-6}$ optionally substituted branched alkyl.
In some embodiments $R^{2l}$ is $C_{3-7}$ optionally substituted cycloalkyl.
In some embodiments $R^{2l}$ is $C_{1-6}$ optionally substituted haloalkyl.
In some embodiments $R^{2l}$ is $C_{1-6}$ optionally substituted alkoxy.
In some embodiments $R^{2l}$ is $CO_2R^5$.
In some embodiments $R^{2l}$ is $CONR^6{}_2$.
In some embodiments $R^{2l}$ is $NR^7{}_2$.
In some embodiments $R^{2l}$ is $SO_3H$.
In some embodiments $R^{2l}$ is sulfate.
In some embodiments $R^{2l}$ is sulfonate.
In some embodiments $R^{2l}$ is optionally substituted aryl.
In some embodiments $R^{2l}$ is optionally substituted aryloxy.
In some embodiments $R^{2l}$ is optionally substituted heteroaryl.
In some embodiments $R^{2l}$ is optionally substituted heterocycle.
In some embodiments $R^{3a}$ is hydrogen.
In some embodiments $R^{3a}$ is $C_{1-6}$ optionally substituted alkyl.
In some embodiments $R^{3a}$ is $C_{1-6}$ optionally substituted branched alkyl.
In some embodiments $R^{3a}$ is $C_{1-6}$ optionally substituted haloalkyl.
In some embodiments $R^{3a}$ is $C_{1-6}$ optionally substituted alkoxy.
In some embodiments $R^{3a}$ is optionally substituted phenyl.
In some embodiments $R^{3a}$ is $CO_2R^8$.
In some embodiments $R^{3b}$ is hydrogen.
In some embodiments $R^{3b}$ is $C_{1-6}$ optionally substituted alkyl.
In some embodiments $R^{3b}$ is $C_{1-6}$ optionally substituted branched alkyl.
In some embodiments $R^{3b}$ is $C_{1-6}$ optionally substituted haloalkyl.
In some embodiments $R^{3b}$ is $C_{1-6}$ optionally substituted alkoxy.
In some embodiments $R^{3b}$ is optionally substituted phenyl.
In some embodiments $R^{3b}$ is $CO_2R^8$.
In some embodiments $R^{3c}$ is hydrogen.
In some embodiments $R^{3c}$ is $C_{1-6}$ optionally substituted alkyl.
In some embodiments $R^{3c}$ is $C_{1-6}$ optionally substituted branched alkyl.
In some embodiments $R^{3c}$ is $C_{1-6}$ optionally substituted haloalkyl.
In some embodiments $R^{3c}$ is $C_{1-6}$ optionally substituted alkoxy.
In some embodiments $R^{3c}$ is optionally substituted phenyl.
In some embodiments $R^{3c}$ is $CO_2R^8$.
In some embodiments $R^{3d}$ is hydrogen.
In some embodiments $R^{3d}$ is $C_{1-6}$ optionally substituted alkyl.
In some embodiments $R^{3d}$ is $C_{1-6}$ optionally substituted branched alkyl.
In some embodiments $R^{3d}$ is $C_{1-6}$ optionally substituted haloalkyl.
In some embodiments $R^{3d}$ is $C_{1-6}$ optionally substituted alkoxy.
In some embodiments $R^{3d}$ is optionally substituted phenyl.
In some embodiments $R^{3d}$ is $CO_2R^8$.
In some embodiments $R^{3e}$ is hydrogen.

In some embodiments $R^{3e}$ is $C_{1-6}$ optionally substituted alkyl.
In some embodiments $R^{3e}$ is $C_{1-6}$ optionally substituted branched alkyl.
In some embodiments $R^{3e}$ is $C_{1-6}$ optionally substituted haloalkyl.
In some embodiments $R^{3e}$ is $C_{1-6}$ optionally substituted alkoxy.
In some embodiments $R^{3e}$ is optionally substituted phenyl.
In some embodiments $R^{3e}$ is $CO_2R^8$.
In some embodiments $R^{3f}$ is hydrogen.
In some embodiments $R^{3f}$ is $C_{1-6}$ optionally substituted alkyl.
In some embodiments $R^{3f}$ is $C_{1-6}$ optionally substituted branched alkyl.
In some embodiments $R^{3f}$ is $C_{1-6}$ optionally substituted haloalkyl.
In some embodiments $R^{3f}$ is $C_{1-6}$ optionally substituted alkoxy.
In some embodiments $R^{3f}$ is optionally substituted phenyl.
In some embodiments $R^{3f}$ is $CO_2R^8$.
In some embodiments $R^{3g}$ is hydrogen.
In some embodiments $R^{3g}$ is $C_{1-6}$ optionally substituted alkyl.
In some embodiments $R^{3g}$ is $C_{1-6}$ optionally substituted branched alkyl.
In some embodiments $R^{3g}$ is $C_{1-6}$ optionally substituted haloalkyl.
In some embodiments $R^{3g}$ is $C_{1-6}$ optionally substituted alkoxy.
In some embodiments $R^{3g}$ is optionally substituted phenyl.
In some embodiments $R^{3g}$ is $CO_2R^8$.
In some embodiments $R^{3h}$ is hydrogen.
In some embodiments $R^{3h}$ is $C_{1-6}$ optionally substituted alkyl.
In some embodiments $R^{3h}$ is $C_{1-6}$ optionally substituted branched alkyl.
In some embodiments $R^{3h}$ is $C_{1-6}$ optionally substituted haloalkyl
In some embodiments $R^{3h}$ is $C_{1-6}$ optionally substituted alkoxy.
In some embodiments $R^{3h}$ is optionally substituted phenyl.
In some embodiments $R^{3h}$ is $CO_2R^8$.
In some embodiments $R^{3i}$ is hydrogen.
In some embodiments $R^{3i}$ is $C_{1-6}$ optionally substituted alkyl.
In some embodiments $R^{3i}$ is $C_{1-6}$ optionally substituted branched alkyl.
In some embodiments $R^{3i}$ is $C_{1-6}$ optionally substituted haloalkyl.
In some embodiments $R^{3i}$ is $C_{1-6}$ optionally substituted alkoxy.
In some embodiments $R^{3i}$ is optionally substituted phenyl.
In some embodiments $R^{3i}$ is $CO_2R^8$.
In some embodiments $R^{3j}$ is hydrogen.
In some embodiments $R^{3j}$ is $C_{1-6}$ optionally substituted alkyl.
In some embodiments $R^{3j}$ is $C_{1-6}$ optionally substituted branched alkyl.
In some embodiments $R^{3j}$ is $C_{1-6}$ optionally substituted haloalkyl.
In some embodiments $R^{3j}$ is $C_{1-6}$ optionally substituted alkoxy.
In some embodiments $R^{3j}$ is optionally substituted phenyl.
In some embodiments $R^{3j}$ is $CO_2R^8$.
In some embodiments $R^{3k}$ is hydrogen.
In some embodiments $R^{3k}$ is $C_{1-6}$ optionally substituted alkyl.
In some embodiments $R^{3k}$ is $C_{1-6}$ optionally substituted branched alkyl.
In some embodiments $R^{3k}$ is $C_{1-6}$ optionally substituted haloalkyl.
In some embodiments $R^{3k}$ is $C_{1-6}$ optionally substituted alkoxy.
In some embodiments $R^{3k}$ is optionally substituted phenyl.
In some embodiments $R^{3k}$ is $CO_2R^8$.
In some embodiments $R^{3l}$ is hydrogen.
In some embodiments $R^{3l}$ is $C_{1-6}$ optionally substituted alkyl.
In some embodiments $R^{3l}$ is $C_{1-6}$ optionally substituted branched alkyl.
In some embodiments $R^{3l}$ is $C_{1-6}$ optionally substituted haloalkyl.
In some embodiments $R^{3l}$ is $C_{1-6}$ optionally substituted alkoxy.
In some embodiments $R^{3l}$ is optionally substituted phenyl.
In some embodiments $R^{3l}$ is $CO_2R^8$.
In some embodiments $R^{4a}$ is hydrogen.
In some embodiments $R^{4a}$ is $C_{1-6}$ optionally substituted alkyl.
In some embodiments $R^{4a}$ is $C_{1-6}$ optionally substituted branched alkyl.
In some embodiments $R^{4a}$ is $C_{1-6}$ optionally substituted cycloalkyl.
In some embodiments $R^{4a}$ is $C_{1-6}$ optionally substituted haloalkyl.
In some embodiments $R^{4a}$ is $C_{1-6}$ optionally substituted alkoxy.
In some embodiments $R^{4a}$ is $CO_2R^5$.
In some embodiments $R^{4a}$ is $CONR^6_2$
In some embodiments $R^{4a}$ is $NR^7_2$.
In some embodiments $R^{4a}$ is sulfate.
In some embodiments $R^{4a}$ is sulfonate.
In some embodiments $R^{4a}$ is optionally substituted aryl.
In some embodiments $R^{4a}$ is optionally substituted aryloxy.
In some embodiments $R^{4a}$ is optionally substituted heteroaryl.
In some embodiments $R^{4a}$ is optionally substituted heterocycle.
In some embodiments $R^{4b}$ is hydrogen.
In some embodiments $R^{4b}$ is $C_{1-6}$ optionally substituted alkyl.
In some embodiments $R^{4b}$ is $C_{1-6}$ optionally substituted branched alkyl.
In some embodiments $R^{4b}$ is $C_{1-6}$ optionally substituted cycloalkyl.
In some embodiments $R^{4b}$ is $C_{1-6}$ optionally substituted haloalkyl.
In some embodiments $R^{4b}$ is $C_{1-6}$ optionally substituted alkoxy.
In some embodiments $R^{4b}$ is $CO_2R^5$.
In some embodiments $R^{4b}$ is $CONR^6_2$
In some embodiments $R^{4b}$ is $NR^7_2$.
In some embodiments $R^{4b}$ is sulfate.
In some embodiments $R^{4b}$ is sulfonate.
In some embodiments $R^{4b}$ is optionally substituted aryl.
In some embodiments $R^{4b}$ is optionally substituted aryloxy.

In some embodiments R$^{4b}$ is optionally substituted heteroaryl.

In some embodiments R$^{4b}$ is optionally substituted heterocycle.

In some embodiments R$^{4c}$ is hydrogen.

In some embodiments R$^{4c}$ is C$_{1-6}$ optionally substituted alkyl.

In some embodiments R$^{4c}$ is C$_{1-6}$ optionally substituted branched alkyl.

In some embodiments R$^{4c}$ is C$_{1-6}$ optionally substituted cycloalkyl.

In some embodiments R$^{4c}$ is C$_{1-6}$ optionally substituted haloalkyl.

In some embodiments R$^{4c}$ is C$_{1-6}$ optionally substituted alkoxy.

In some embodiments R$^{4c}$ is CO$_2$R$^5$.

In some embodiments R$^{4c}$ is CONR$^6{}_2$.

In some embodiments R$^{4c}$ is NR$^7{}_2$.

In some embodiments R$^{4c}$ is sulfate.

In some embodiments R$^{4c}$ is sulfonate.

In some embodiments R$^{4c}$ is optionally substituted aryl.

In some embodiments R$^{4c}$ is optionally substituted aryloxy.

In some embodiments R$^{4c}$ is optionally substituted heteroaryl.

In some embodiments R$^{4c}$ is optionally substituted heterocycle.

In some embodiments R$^{4a}$ and R$^{4b}$ are taken together with the atom to which they are bound to form an optionally substituted ring having from 6 ring atoms containing 2 oxygen atoms.

In some embodiments R$^5$ is hydrogen.
In some embodiments R$^5$ is optionally substituted alkyl.
In some embodiments R$^6$ is hydrogen.
In some embodiments R$^6$ is optionally substituted alkyl.
In some embodiments R$^7$ is hydrogen.
In some embodiments R$^7$ is optionally substituted alkyl.
In some embodiments R$^8$ is hydrogen.
In some embodiments R$^8$ is optionally substituted alkyl.
In some embodiment t is an integer.
In some embodiments t is 1.
In some embodiments t is 2.
In some embodiments t is 3.
In some embodiments t is 4.
In some embodiments t is 5.
In some embodiments t is 6.
In some embodiments A$^2$ is

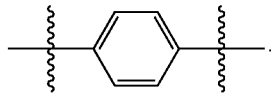

In some embodiments A$^2$ is

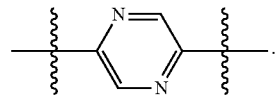

In some embodiments A$^2$ is

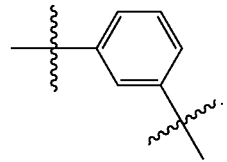 [SMILES: *c1cccc(*)c1]

In some embodiments A$^2$ is

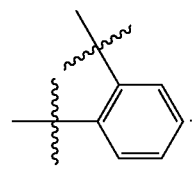 [SMILES: *c1ccccc1*]

In some embodiments A$^2$ is

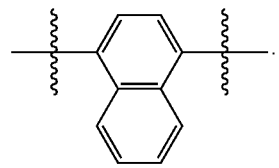

In some embodiments A$^2$ is

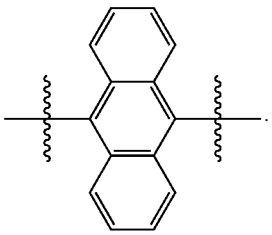 [SMILES: *c1c2ccccc2c(*)c2ccccc12]

In some embodiments A$^2$ is

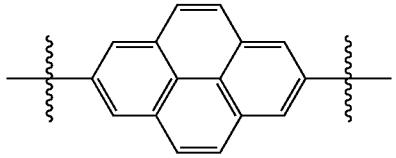

In some embodiments $A^2$ is
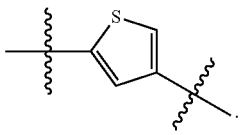 [SMILES: *c1csc(*)c1]
In some embodiments $A^2$ is
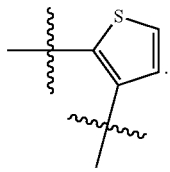 [SMILES: *c1ccsc1*]
In some embodiments $A^3$ is
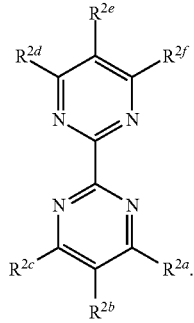
In some embodiments $A^3$ is
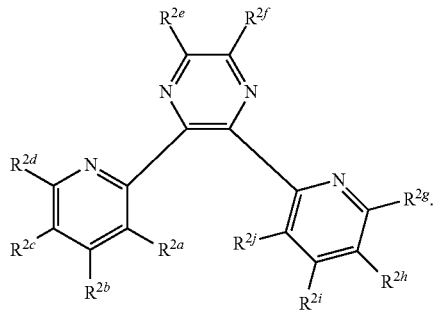
In some embodiments $A^3$ is
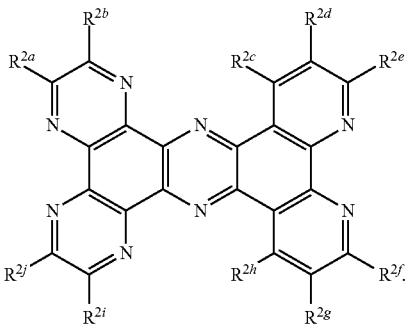
In some embodiments $A^3$ is
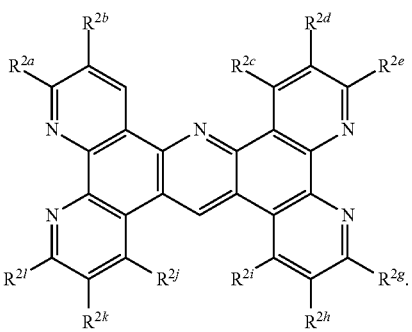
In some embodiments $A^3$ is
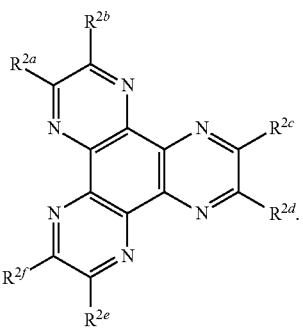
Exemplary embodiments include compounds having the formula (VIII) or a pharmaceutically acceptable salt form thereof:

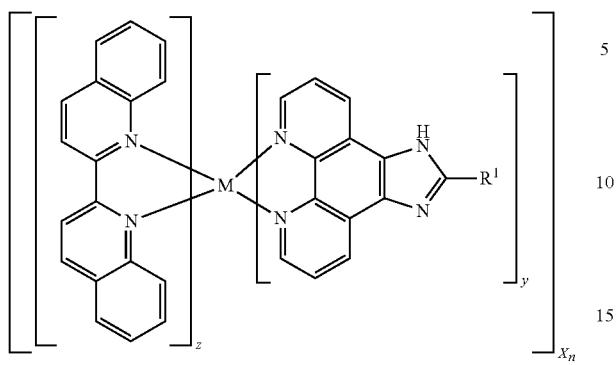
(VIII)
wherein non-limiting examples of M, z, y, X, n, and R¹ are defined herein below in Table 1.
TABLE 1
| Entry | M | z | Y | R¹ | X | n |
|---|---|---|---|---|---|---|
| 1 | Os | 1 | 2 | H | Cl | 2 |
| 2 | Os | 1 | 2 | (thiophene) | Cl | 2 |
| 3 | Os | 1 | 2 | (bithiophene) | Cl | 2 |
| 4 | Os | 1 | 2 | (terthiophene) | Cl | 2 |
| 5 | Os | 1 | 2 | (quaterthiophene) | Cl | 2 |
| 6 | Os | 1 | 2 | (quinquethiophene) | Cl | 2 |
| 7 | Os | 1 | 2 | (sexithiophene) | Cl | 2 |
| 8 | Os | 1 | 2 | (EDOT) | Cl | 2 |

TABLE 1-continued

| Entry | M | z | Y | R¹ | X | n |
|---|---|---|---|---|---|---|
| 9 | Os | 1 | 2 | (bis-EDOT thiophene group) | Cl | 2 |
| 10 | Os | 1 | 2 | (EDOT-thiophene-EDOT group) | Cl | 2 |
| 11 | Os | 1 | 2 | (tetra-EDOT/thiophene group) | Cl | 2 |
| 12 | Os | 1 | 2 | (penta-thiophene/EDOT group) | Cl | 2 |
| 13 | Os | 1 | 2 | (hexa-thiophene/EDOT group) | Cl | 2 |
| 14 | Os | 1 | 2 | (pyrenyl group) | Cl | 2 |

TABLE 1-continued
| Entry | M | z | Y | R¹ | X | n |
|---|---|---|---|---|---|---|
| 15 | Os | 1 | 2 | 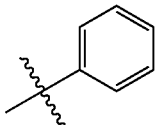 [SMILES: *c1ccccc1] | Cl | 2 |
| 16 | Os | 1 | 2 | 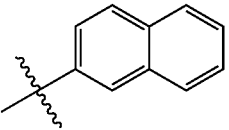 [SMILES: *c1ccc2ccccc2c1] | Cl | 2 |
| 17 | Os | 1 | 2 | 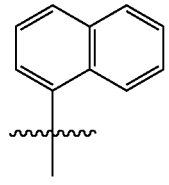 [SMILES: *c1cccc2ccccc12] | Cl | 2 |
| 18 | Os | 1 | 2 | 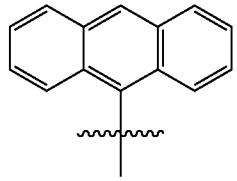 [SMILES: *c1c2ccccc2cc2ccccc12] | Cl | 2 |
| 19 | Os | 1 | 2 | 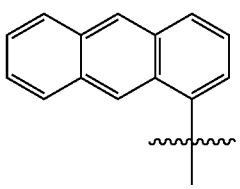 [SMILES: *c1cccc2cc3ccccc3cc12] | Cl | 2 |
| 20 | Os | 1 | 2 | 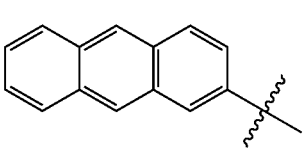 | Cl | 2 |
| 21 | Os | 1 | 2 | H | PF$_6$ | 2 |
| 22 | Os | 1 | 2 | 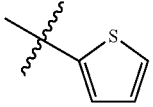 [SMILES: *c1cccs1] | PF$_6$ | 2 |
| 23 | Os | 1 | 2 | 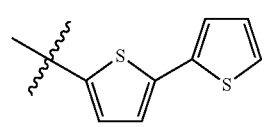 [SMILES: *c1ccc(-c2cccs2)s1] | PF$_6$ | 2 |
| 24 | Os | 1 | 2 | 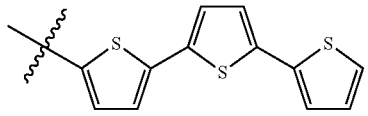 [SMILES: *c1ccc(-c2ccc(-c3cccs3)s2)s1] | PF$_6$ | 2 |
| 25 | Os | 1 | 2 | 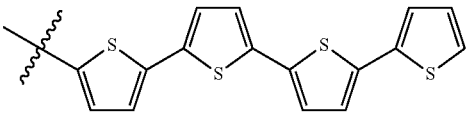 [SMILES: *c1ccc(-c2ccc(-c3ccc(-c4cccs4)s3)s2)s1] | PF$_6$ | 2 |

TABLE 1-continued
| Entry | M | z | Y | R¹ | X | n |
|---|---|---|---|---|---|---|
| 26 | Os | 1 | 2 | 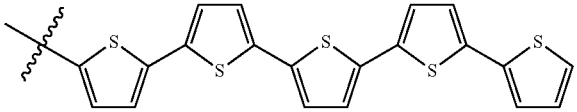 [SMILES: *c1ccc(-c2ccc(-c3ccc(-c4ccc(-c5cccs5)s4)s3)s2)s1] | PF₆ | 2 |
| 27 | Os | 1 | 2 | 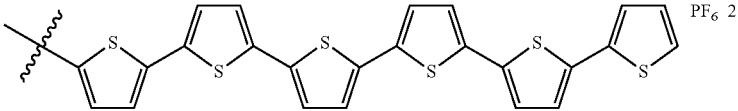 | PF₆ | 2 |
| 28 | Os | 1 | 2 | 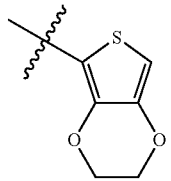 [SMILES: *c1scc2c1OCCO2] | PF₆ | 2 |
| 29 | Os | 1 | 2 | 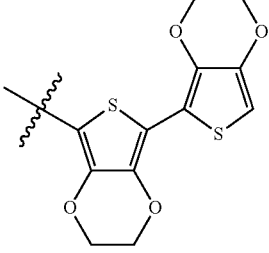 | PF₆ | 2 |
| 30 | Os | 1 | 2 | 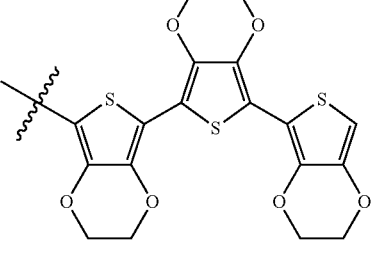 | PF₆ | 2 |
| 31 | Os | 1 | 2 | 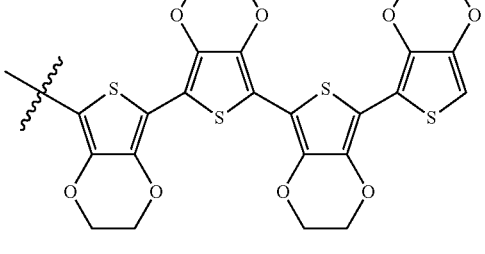 | PF₆ | 2 |
| 32 | Os | 1 | 2 | 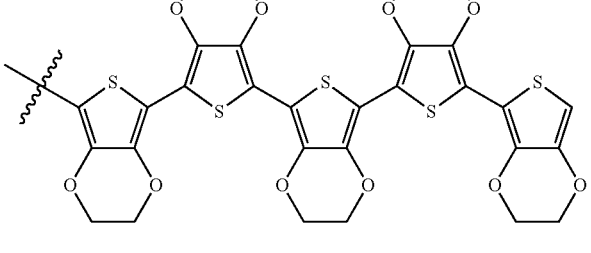 | PF₆ | 2 |

TABLE 1-continued
| Entry | M | z | Y | R¹ | X | n |
|---|---|---|---|---|---|---|
| 33 | Os | 1 | 2 | 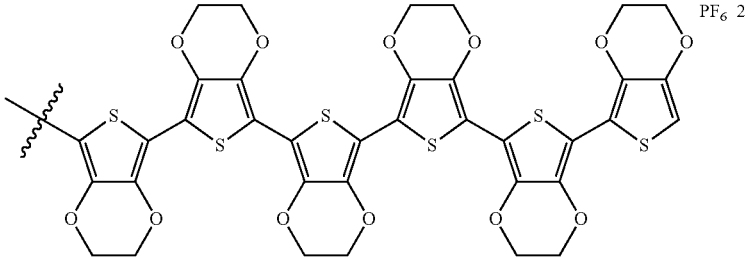 | PF$_6$ | 2 |
| 34 | Os | 1 | 2 | 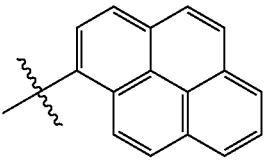 [SMILES: *c1ccc2ccc3cccc4ccc1c2c34] | PF$_6$ | 2 |
| 35 | Os | 1 | 2 | 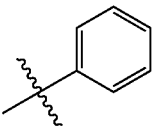 | PF$_6$ | 2 |
| 36 | Os | 1 | 2 | 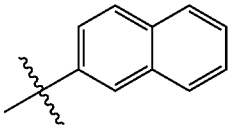 [SMILES: *c1ccc2ccccc2c1] | PF$_6$ | 2 |
| 37 | Os | 1 | 2 | 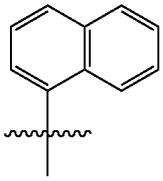 [SMILES: *c1cccc2ccccc12] | PF$_6$ | 2 |
| 38 | Os | 1 | 2 | 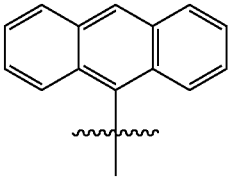 [SMILES: *c1c2ccccc2cc2ccccc12] | PF$_6$ | 2 |
| 39 | Os | 1 | 2 | 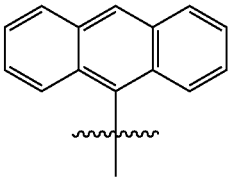 [SMILES: *c1c2ccccc2cc2ccccc12] | PF$_6$ | 2 |
| 40 | Os | 1 | 2 | 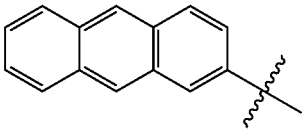 [SMILES: *c1ccc2cc3ccccc3cc2c1] | PF$_6$ | 2 |
| 41 | Os | 2 | 1 | H | Cl | 2 |

TABLE 1-continued

| Entry | M | z | Y | R¹ | X | n |
|---|---|---|---|---|---|---|
| 42 | Os | 1 | 2 | thiophene | Cl | 2 |
| 43 | Os | 1 | 2 | bithiophene | Cl | 2 |
| 44 | Os | 1 | 2 | terthiophene | Cl | 2 |
| 45 | Os | 1 | 2 | quaterthiophene | Cl | 2 |
| 46 | Os | 1 | 2 | quinquethiophene | Cl | 2 |
| 47 | Os | 1 | 2 | sexithiophene | Cl | 2 |
| 48 | Os | 1 | 2 | EDOT | Cl | 2 |
| 49 | Os | 1 | 2 | bis-EDOT | Cl | 2 |
| 50 | Os | 1 | 2 | tris-EDOT | Cl | 2 |

TABLE 1-continued
| Entry | M | z | Y | R¹ | X | n |
|---|---|---|---|---|---|---|
| 51 | Os | 1 | 2 | 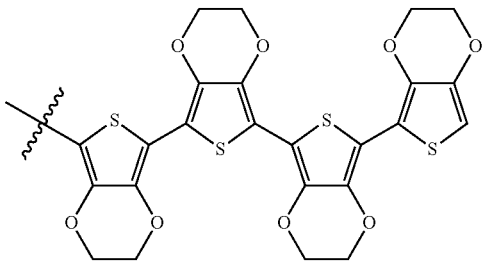 [SMILES: *c1sc(-c2sc(-c3sc(-c4scc5c4OCCO5)c4c3OCCO4)c3c2OCCO3)c2c1OCCO2] | Cl | 2 |
| 52 | Os | 1 | 2 | 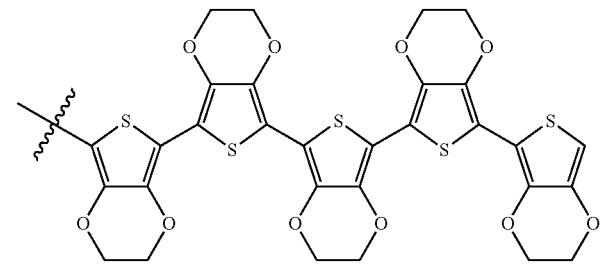 [SMILES: *c1sc(-c2sc(-c3sc(-c4sc(-c5scc6c5OCCO6)c5c4OCCO5)c4c3OCCO4)c3c2OCCO3)c2c1OCCO2] | Cl | 2 |
| 53 | Os | 1 | 2 | 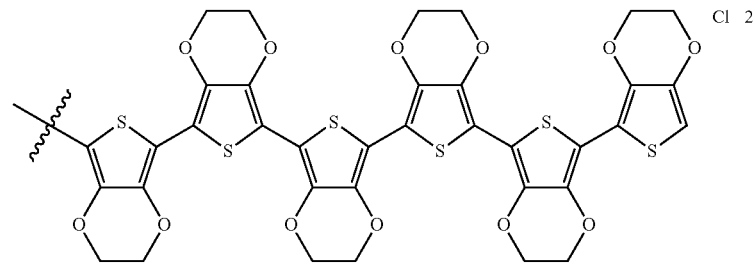 | Cl | 2 |
| 54 | Os | 1 | 2 | 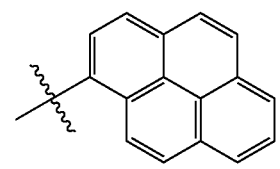 [SMILES: *c1ccc2ccc3cccc4ccc1c2c34] | Cl | 2 |
| 55 | Os | 1 | 2 | 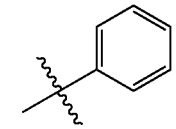 [SMILES: *c1ccccc1] | Cl | 2 |
| 56 | Os | 1 | 2 | 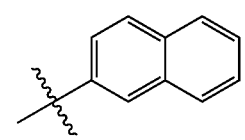 [SMILES: *c1ccc2ccccc2c1] | Cl | 2 |
| 57 | Os | 1 | 2 | 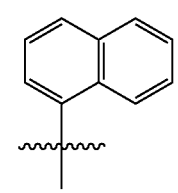 [SMILES: *c1cccc2ccccc12] | Cl | 2 |

TABLE 1-continued
| Entry | M | z | Y | R¹ | X | n |
|---|---|---|---|---|---|---|
| 58 | Os | 1 | 2 | 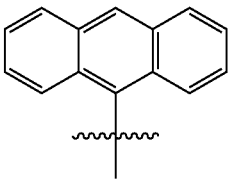 [SMILES: *c1c2ccccc2cc2ccccc12] | Cl | 2 |
| 59 | Os | 1 | 2 | 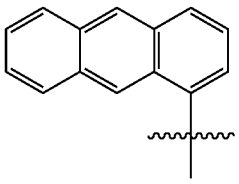 [SMILES: *c1cccc2cc3ccccc3cc12] | Cl | 2 |
| 60 | Os | 1 | 2 | 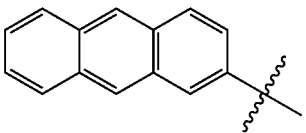 [SMILES: *c1ccc2cc3ccccc3cc2c1] | Cl | 2 |
| 61 | Os | 1 | 2 | H | $PF_6$ | 2 |
| 62 | Os | 1 | 2 | 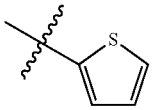 [SMILES: *c1cccs1] | $PF_6$ | 2 |
| 63 | Os | 1 | 2 | 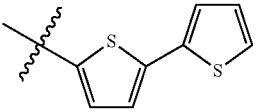 [SMILES: *c1ccc(-c2cccs2)s1] | $PF_6$ | 2 |
| 64 | Os | 1 | 2 | 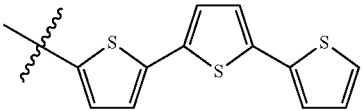 [SMILES: *c1ccc(-c2ccc(-c3cccs3)s2)s1] | $PF_6$ | 2 |
| 65 | Os | 1 | 2 | 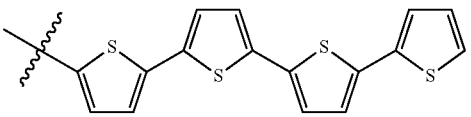 [SMILES: *c1ccc(-c2ccc(-c3ccc(-c4cccs4)s3)s2)s1] | $PF_6$ | 2 |
| 66 | Os | 1 | 2 | 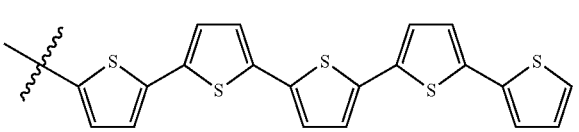 | $PF_6$ | 2 |
| 67 | Os | 1 | 2 | 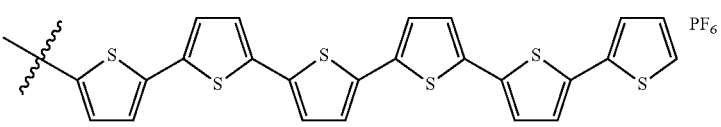 | $PF_6$ | 2 |
| 68 | Os | 1 | 2 | 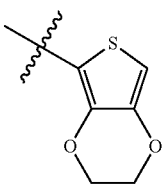 | $PF_6$ | 2 |

TABLE 1-continued
| Entry | M | z | Y | R¹ | X | n |
|---|---|---|---|---|---|---|
| 69 | Os | 1 | 2 | 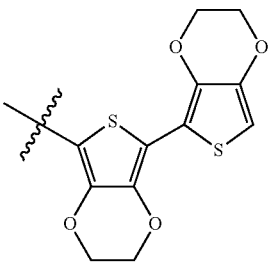 [SMILES: *c1sc(-c2scc3c2OCCO3)c2c1OCCO2] | PF$_6$ | 2 |
| 70 | Os | 1 | 2 | 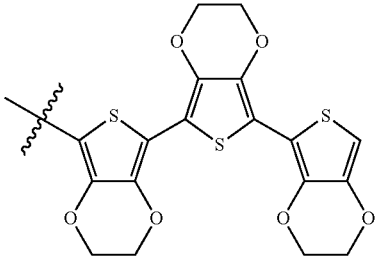 [SMILES: *c1sc(-c2sc(-c3scc4c3OCCO4)c3c2OCCO3)c2c1OCCO2] | PF$_6$ | 2 |
| 71 | Os | 1 | 2 | 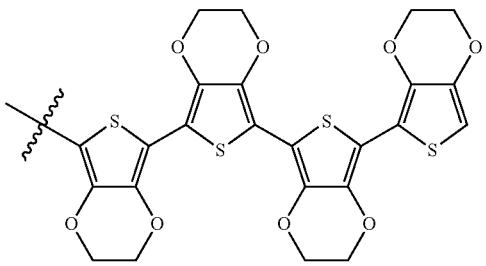 [SMILES: *c1sc(-c2sc(-c3sc(-c4scc5c4OCCO5)c4c3OCCO4)c3c2OCCO3)c2c1OCCO2] | PF$_6$ | 2 |
| 72 | Os | 1 | 2 | 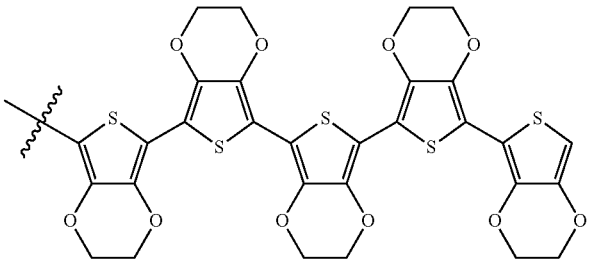 [SMILES: *c1sc(-c2sc(-c3sc(-c4sc(-c5scc6c5OCCO6)c5c4OCCO5)c4c3OCCO4)c3c2OCCO3)c2c1OCCO2] | PF$_6$ | 2 |
| 73 | Os | 1 | 2 | 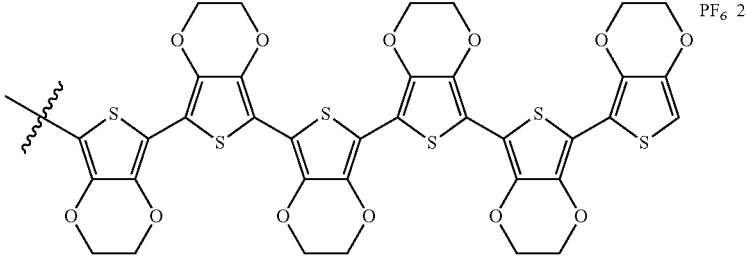 | PF$_6$ | 2 |
| 74 | Os | 1 | 2 | 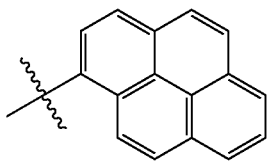 [SMILES: *c1ccc2ccc3cccc4ccc1c2c34] | PF$_6$ | 2 |

TABLE 1-continued
| Entry | M | z | Y | R¹ | X | n |
|---|---|---|---|---|---|---|
| 75 | Os | 1 | 2 | 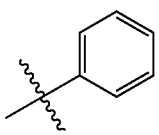 | PF₆ | 2 |
| 76 | Os | 1 | 2 | 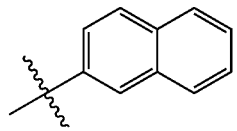 [SMILES: *c1ccc2ccccc2c1] | PF₆ | 2 |
| 77 | Os | 1 | 2 | 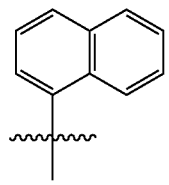 | PF₆ | 2 |
| 78 | Os | 1 | 2 | 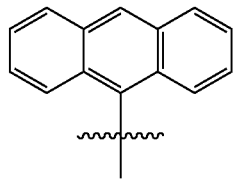 [SMILES: *c1c2ccccc2cc2ccccc12] | PF₆ | 2 |
| 79 | Os | 1 | 2 | 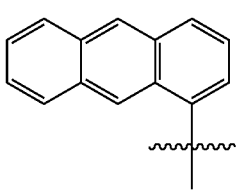 [SMILES: *c1cccc2cc3ccccc3cc12] | PF₆ | 2 |
| 80 | Os | 1 | 2 | 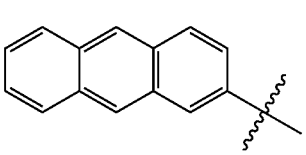 [SMILES: *c1ccc2cc3ccccc3cc2c1] | PF₆ | 2 |
Exemplary embodiments include compounds having the formula (IX) or a pharmaceutically acceptable salt form thereof:
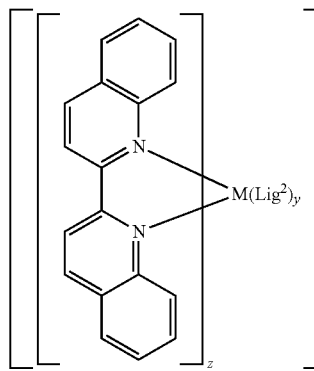
(IX)
Wherein non-limiting examples of M, Lig, y, z, X, and n are defined herein below in Table 2.
TABLE 2
| Entry | M | Lig² | Y | z | X | N |
|---|---|---|---|---|---|---|
| 1 | Os | 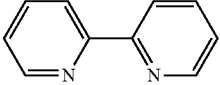 | 1 | 2 | Cl | 2 |
| 2 | Os | 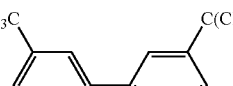 | 1 | 2 | Cl | 2 |
| 3 | Os | 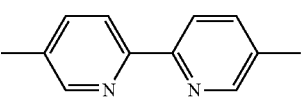 | 1 | 2 | Cl | 2 |

TABLE 2-continued

| Entry | M | Lig² | Y | z | X | N |
|---|---|---|---|---|---|---|
| 4 | Os | 4,4'-dimethyl-2,2'-bipyridine | 1 | 2 | Cl | 2 |
| 5 | Os | 4,4',6,6'-tetramethyl-2,2'-bipyridine | 1 | 2 | Cl | 2 |
| 6 | Os | 4,4'-dimethoxy-2,2'-bipyridine | 1 | 2 | Cl | 2 |
| 7 | Os | 4,4'-bis(methoxycarbonyl)-2,2'-bipyridine | 1 | 2 | Cl | 2 |
| 8 | Os | 2,2'-bipyrimidine | 1 | 2 | Cl | 2 |
| 9 | Os | 2,3-bis(2-pyridyl)pyrazine | 1 | 2 | Cl | 2 |
| 10 | Os | 3,4,7,8-tetramethyl-1,10-phenanthroline | 1 | 2 | Cl | 2 |
| 11 | Os | 5,6-dimethyl-1,10-phenanthroline | 1 | 2 | Cl | 2 |
| 12 | Os | 4-methyl-1,10-phenanthroline | 1 | 2 | Cl | 2 |
| 13 | Os | 5-methyl-1,10-phenanthroline | 1 | 2 | Cl | 2 |
| 14 | Os | 5-chloro-1,10-phenanthroline | 1 | 2 | Cl | 2 |
| 15 | Os | 4,7-diphenyl-1,10-phenanthroline | 1 | 2 | Cl | 2 |
| 16 | Os | 5-amino-1,10-phenanthroline | 1 | 2 | Cl | 2 |
| 17 | Os | 1,10-phenanthroline | 1 | 2 | Cl | 2 |
| 18 | Os | pyrazino[2,3-f][1,10]phenanthroline | 1 | 2 | Cl | 2 |
| 19 | Os | dipyrido[3,2-a:2',3'-c]phenazine | 1 | 2 | Cl | 2 |
| 20 | Os | benzo-dipyrido-phenazine derivative | 1 | 2 | Cl | 2 |
| 21 | Os | tetrahydro-dipyrido-phenazine derivative | 1 | 2 | Cl | 2 |

TABLE 2-continued

| Entry | M | Lig² | Y | z | X | N |
|---|---|---|---|---|---|---|
| 22 | Os | (dipyridophenazine with NH₂) | 1 | 2 | Cl | 2 |
| 23 | Os | (dipyridophenazine with CO₂H) | 1 | 2 | Cl | 2 |
| 24 | Os | (dipyridophenazine with SO₃H) | 1 | 2 | Cl | 2 |
| 25 | Os | (pyrazino-phenanthroline) | 1 | 2 | Cl | 2 |
| 26 | Os | (pyrazino-quinoxaline) | 1 | 2 | Cl | 2 |
| 27 | Os | (extended fused N-heterocycle) | 1 | 2 | Cl | 2 |
| 28 | Os | (extended fused N-heterocycle) | 1 | 2 | Cl | 2 |
| 29 | Os | 2,2'-bipyridine | 1 | 2 | PF₆ | 2 |
| 30 | Os | 4,4'-di-tert-butyl-2,2'-bipyridine | 1 | 2 | PF₆ | 2 |
| 31 | Os | 5,5'-dimethyl-2,2'-bipyridine | 1 | 2 | PF₆ | 2 |
| 32 | Os | 4,4'-dimethyl-2,2'-bipyridine | 1 | 2 | PF₆ | 2 |
| 33 | Os | 6,6'-dimethyl-2,2'-bipyridine | 1 | 2 | PF₆ | 2 |
| 34 | Os | 4,4'-dimethoxy-2,2'-bipyridine | 1 | 2 | PF₆ | 2 |
| 35 | Os | 4,4'-bis(methoxycarbonyl)-2,2'-bipyridine | 1 | 2 | PF₆ | 2 |
| 36 | Os | 2,2'-bipyrimidine | 1 | 2 | PF₆ | 2 |
| 37 | Os | 2,3-di(pyridin-2-yl)pyrazine | 1 | 2 | PF₆ | 2 |
| 38 | Os | 3,4,7,8-tetramethyl-1,10-phenanthroline | 1 | 2 | PF₆ | 2 |
| 39 | Os | 5,6-dimethyl-1,10-phenanthroline | 1 | 2 | PF₆ | 2 |

TABLE 2-continued

| Entry | M | Lig² | Y | z | X | N |
|---|---|---|---|---|---|---|
| 40 | Os | (4-methyl-1,10-phenanthroline) | 1 | 2 | PF₆ | 2 |
| 41 | Os | (5-methyl-1,10-phenanthroline) | 1 | 2 | PF₆ | 2 |
| 42 | Os | (methyl-1,10-phenanthroline) | 1 | 2 | PF₆ | 2 |
| 43 | Os | (4,7-diphenyl-1,10-phenanthroline) | 1 | 2 | PF₆ | 2 |
| 44 | Os | (amino-1,10-phenanthroline) | 1 | 2 | PF₆ | 2 |
| 45 | Os | (1,10-phenanthroline) | 1 | 2 | PF₆ | 2 |
| 46 | Os | (pyrazino-phenanthroline) | 1 | 2 | PF₆ | 2 |
| 47 | Os | (dipyrido-phenazine) | 1 | 2 | PF₆ | 2 |
| 48 | Os | (dipyrido-benzo-phenazine) | 1 | 2 | PF₆ | 2 |
| 49 | Os | (tetrahydro-dipyrido-phenazine) | 1 | 2 | PF₆ | 2 |
| 50 | Os | (amino-dipyrido-phenazine) | 1 | 2 | PF₆ | 2 |
| 51 | Os | (carboxy-dipyrido-phenazine) | 1 | 2 | PF₆ | 2 |
| 52 | Os | (sulfo-dipyrido-phenazine) | 1 | 2 | PF₆ | 2 |
| 53 | Os | (tetraazo-phenanthroline) | 1 | 2 | PF₆ | 2 |
| 54 | Os | (pyrazino-pyrido-pyrazine) | 1 | 2 | PF₆ | 2 |

TABLE 2-continued

| Entry | M | Lig² | Y | z | X | N |
|---|---|---|---|---|---|---|
| 55 | Os | (structure) | 1 | 2 | PF₆ | 2 |
| 56 | Os | (structure) | 1 | 2 | PF₆ | 2 |
| 57 | Os | (structure) | 2 | 1 | Cl | 2 |
| 58 | Os | (structure) | 2 | 1 | Cl | 2 |
| 59 | Os | (structure) | 2 | 1 | Cl | 2 |
| 60 | Os | (structure) | 2 | 1 | Cl | 2 |
| 61 | Os | (structure) | 2 | 1 | Cl | 2 |
| 62 | Os | (structure) | 2 | 1 | Cl | 2 |
| 63 | Os | (structure) | 2 | 1 | Cl | 2 |
| 64 | Os | (structure) | 2 | 1 | Cl | 2 |
| 65 | Os | (structure) | 2 | 1 | Cl | 2 |
| 66 | Os | (structure) | 2 | 1 | Cl | 2 |
| 67 | Os | (structure) | 2 | 1 | Cl | 2 |
| 68 | Os | (structure) | 2 | 1 | Cl | 2 |
| 69 | Os | (structure) | 2 | 1 | Cl | 2 |
| 70 | Os | (structure) | 2 | 1 | Cl | 2 |
| 71 | Os | (structure) | 2 | 1 | Cl | 2 |
| 72 | Os | (structure) | 2 | 1 | Cl | 2 |
| 73 | Os | (structure) | 2 | 1 | Cl | 2 |

TABLE 2-continued

| Entry | M | Lig² | Y | z | X | N |
|---|---|---|---|---|---|---|
| 74 | Os | [structure] | 2 | 1 | Cl | 2 |
| 75 | Os | [structure] | 2 | 1 | Cl | 2 |
| 76 | Os | [structure] | 2 | 1 | Cl | 2 |
| 77 | Os | [structure] | 2 | 1 | Cl | 2 |
| 78 | Os | [structure with NH₂] | 2 | 1 | Cl | 2 |
| 79 | Os | [structure with CO₂H] | 2 | 1 | Cl | 2 |
| 80 | Os | [structure with SO₃H] | 2 | 1 | Cl | 2 |
| 81 | Os | [structure] | 2 | 1 | Cl | 2 |
| 82 | Os | [structure] | 2 | 1 | Cl | 2 |
| 83 | Os | [structure] | 2 | 1 | Cl | 2 |
| 84 | Os | [structure] | 2 | 1 | Cl | 2 |
| 85 | Os | [bipyridine] | 2 | 1 | PF₆ | 2 |
| 86 | Os | (CH₃)₃C-[bipyridine]-C(CH₃)₃ | 2 | 1 | PF₆ | 2 |
| 87 | Os | [dimethyl bipyridine] | 2 | 1 | PF₆ | 2 |
| 88 | Os | [dimethyl bipyridine] | 2 | 1 | PF₆ | 2 |
| 89 | Os | [dimethyl bipyridine] | 2 | 1 | PF₆ | 2 |

TABLE 2-continued

| Entry | M | Lig² | Y | z | X | N |
|---|---|---|---|---|---|---|
| 90 | Os |  4,4'-dimethoxy-2,2'-bipyridine | 2 | 1 | PF₆ | 2 |
| 91 | Os |  dimethyl 2,2'-bipyridine-4,4'-dicarboxylate | 2 | 1 | PF₆ | 2 |
| 92 | Os |  2,2'-bipyrimidine | 2 | 1 | PF₆ | 2 |
| 93 | Os | 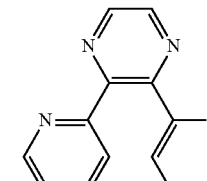 2,3-di(pyridin-2-yl)pyrazine | 2 | 1 | PF₆ | 2 |
| 94 | Os | 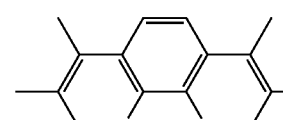 3,4,7,8-tetramethyl-1,10-phenanthroline | 2 | 1 | PF₆ | 2 |
| 95 | Os | 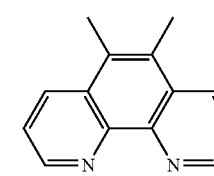 5,6-dimethyl-1,10-phenanthroline | 2 | 1 | PF₆ | 2 |
| 96 | Os | 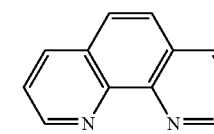 4-methyl-1,10-phenanthroline | 2 | 1 | PF₆ | 2 |
| 97 | Os | 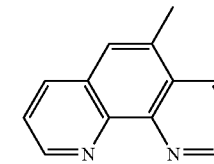 5-methyl-1,10-phenanthroline | 2 | 1 | PF₆ | 2 |
| 98 | Os | 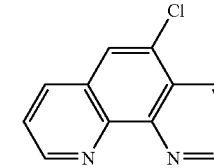 5-chloro-1,10-phenanthroline | 2 | 1 | PF₆ | 2 |
| 99 | Os | 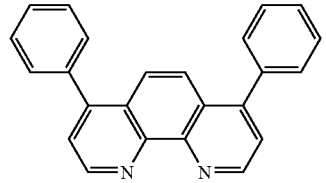 [SMILES: c1ccc(-c2ccnc3c2ccc2c(-c4ccccc4)ccnc23)cc1] 4,7-diphenyl-1,10-phenanthroline | 2 | 1 | PF₆ | 2 |
| 100 | Os | 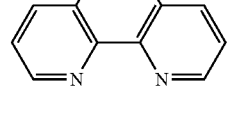 5-amino-1,10-phenanthroline | 2 | 1 | PF₆ | 2 |
| 101 | Os | 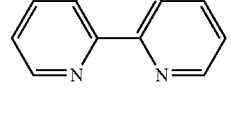 1,10-phenanthroline | 2 | 1 | PF₆ | 2 |
| 102 | Os | 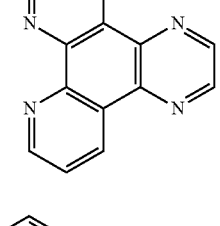 | 2 | 1 | PF₆ | 2 |
| 103 | Os | 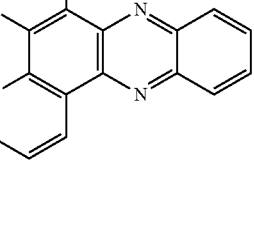 | 2 | 1 | PF₆ | 2 |
| 104 | Os | 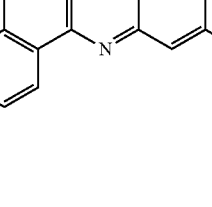 | 2 | 1 | PF₆ | 2 |
| 105 | Os | 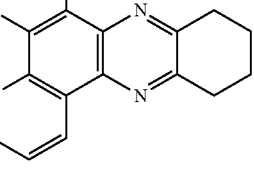 | 2 | 1 | PF₆ | 2 |

TABLE 2-continued
| Entry | M | Lig² | Y | z | X | N |
|---|---|---|---|---|---|---|
| 106 | Os | 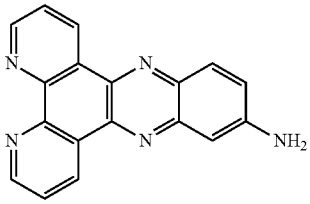 [SMILES: Nc1ccc2nc3c4cccnc4c4ncccc4c3nc2c1] | 2 | 1 | PF₆ | 2 |
| 107 | Os | 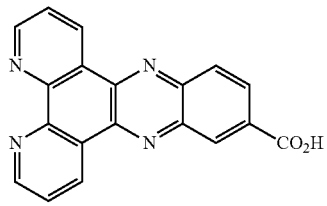 [SMILES: O=C(O)c1ccc2nc3c4cccnc4c4ncccc4c3nc2c1] | 2 | 1 | PF₆ | 2 |
| 108 | Os | 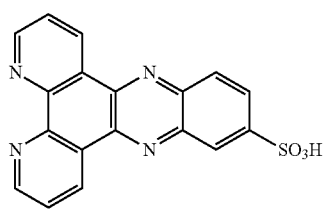 | 2 | 1 | PF₆ | 2 |
| 109 | Os | 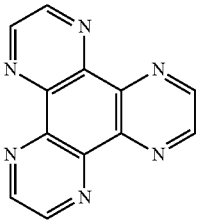 [SMILES: c1cnc2c(n1)c1nccnc1c1nccnc21] | 2 | 1 | PF₆ | 2 |
| 110 | Os | 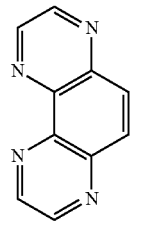 | 2 | 1 | PF₆ | 2 |
| 111 | Os | 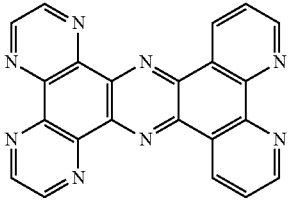 [SMILES: c1cnc2c(c1)c1nc3c4nccnc4c4nccnc4c3nc1c1cccnc12] | 2 | 1 | PF₆ | 2 |
| 112 | Os | 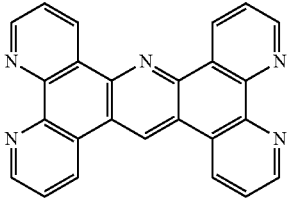 [SMILES: c1cnc2c(c1)c1cc3c4cccnc4c4ncccc4c3nc1c1cccnc12] | 2 | 1 | PF₆ | 2 |
Exemplary embodiments include compounds having the formula (X) or a pharmaceutically acceptable salt form thereof:
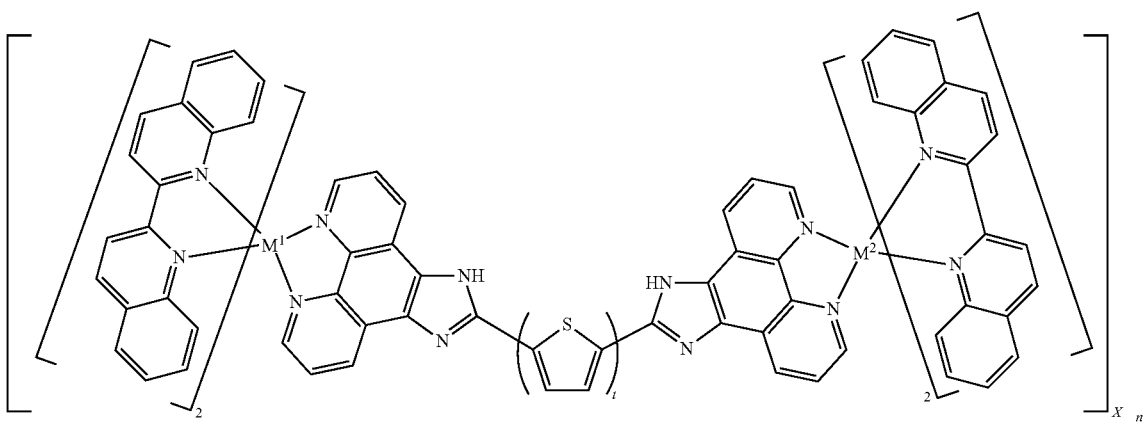
(X)
wherein non-limiting examples of M, t, X, and q are defined herein below in Table 4.

TABLE 4

| Entry | M[1] | M[2] | t | X | n | Entry | M[1] | M[2] | t | X | n |
|---|---|---|---|---|---|---|---|---|---|---|---|
| 1 | Os | Os | 1 | Cl | 4 | 7 | Os | Os | 1 | PF$_6$ | 4 |
| 2 | Os | Os | 2 | Cl | 4 | 8 | Os | Os | 2 | PF$_6$ | 4 |
| 3 | Os | Os | 3 | Cl | 4 | 9 | Os | Os | 3 | PF$_6$ | 4 |
| 4 | Os | Os | 4 | Cl | 4 | 10 | Os | Os | 4 | PF$_6$ | 4 |
| 5 | Os | Os | 5 | Cl | 4 | 11 | Os | Os | 5 | PF$_6$ | 4 |
| 6 | Os | Os | 6 | Cl | 4 | 12 | Os | Os | 6 | PF$_6$ | 4 |
| 7 | Os | Ru | 1 | Cl | 4 | 7 | Os | Ru | 1 | PF$_6$ | 4 |
| 8 | Os | Ru | 2 | Cl | 4 | 8 | Os | Ru | 2 | PF$_6$ | 4 |
| 9 | Os | Ru | 3 | Cl | 4 | 9 | Os | Ru | 3 | PF$_6$ | 4 |
| 10 | Os | Ru | 4 | Cl | 4 | 10 | Os | Ru | 4 | PF$_6$ | 4 |
| 11 | Os | Ru | 5 | Cl | 4 | 11 | Os | Ru | 5 | PF$_6$ | 4 |
| 12 | Os | Ru | 6 | Cl | 4 | 12 | Os | Ru | 6 | PF$_6$ | 4 |

Exemplary embodiments include compounds having the formula (XI) or a pharmaceutically acceptable salt form thereof:

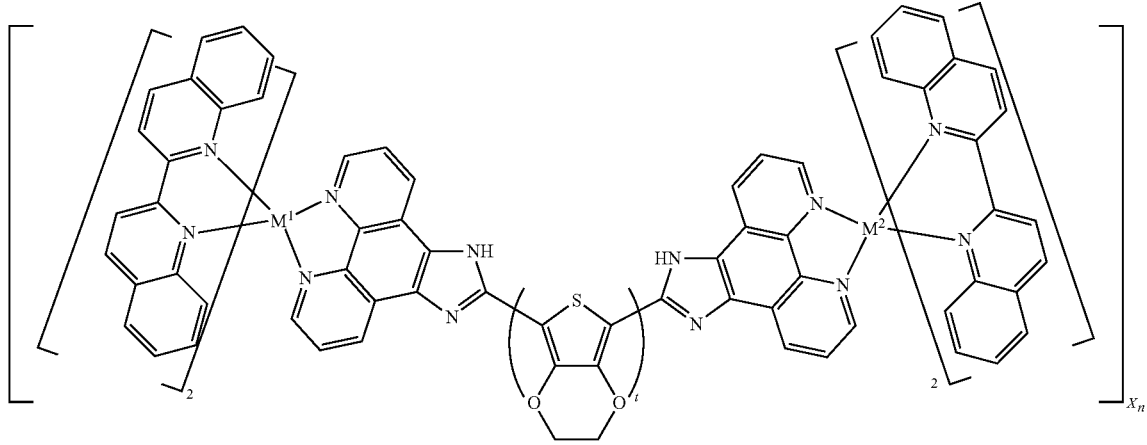

(XI)

wherein non-limiting examples of M, Lig, t, X, and q are defined herein below in Table 5.

TABLE 5

| Entry | M[1] | M[2] | t | X | n | Entry | M[1] | M[2] | t | X | n |
|---|---|---|---|---|---|---|---|---|---|---|---|
| 1 | Os | Os | 1 | Cl | 4 | 7 | Os | Os | 1 | PF$_6$ | 4 |
| 2 | Os | Os | 2 | Cl | 4 | 8 | Os | Os | 2 | PF$_6$ | 4 |
| 3 | Os | Os | 3 | Cl | 4 | 9 | Os | Os | 3 | PF$_6$ | 4 |
| 4 | Os | Os | 4 | Cl | 4 | 10 | Os | Os | 4 | PF$_6$ | 4 |
| 5 | Os | Os | 5 | Cl | 4 | 11 | Os | Os | 5 | PF$_6$ | 4 |
| 6 | Os | Os | 6 | Cl | 4 | 12 | Os | Os | 6 | PF$_6$ | 4 |
| 7 | Os | Ru | 1 | Cl | 4 | 7 | Os | Ru | 1 | PF$_6$ | 4 |
| 8 | Os | Ru | 2 | Cl | 4 | 8 | Os | Ru | 2 | PF$_6$ | 4 |
| 9 | Os | Ru | 3 | Cl | 4 | 9 | Os | Ru | 3 | PF$_6$ | 4 |
| 10 | Os | Ru | 4 | Cl | 4 | 10 | Os | Ru | 4 | PF$_6$ | 4 |
| 11 | Os | Ru | 5 | Cl | 4 | 11 | Os | Ru | 5 | PF$_6$ | 4 |
| 12 | Os | Ru | 6 | Cl | 4 | 12 | Os | Ru | 6 | PF$_6$ | 4 |

Exemplary embodiments include compounds having the formula (XII) or a pharmaceutically acceptable salt form thereof:

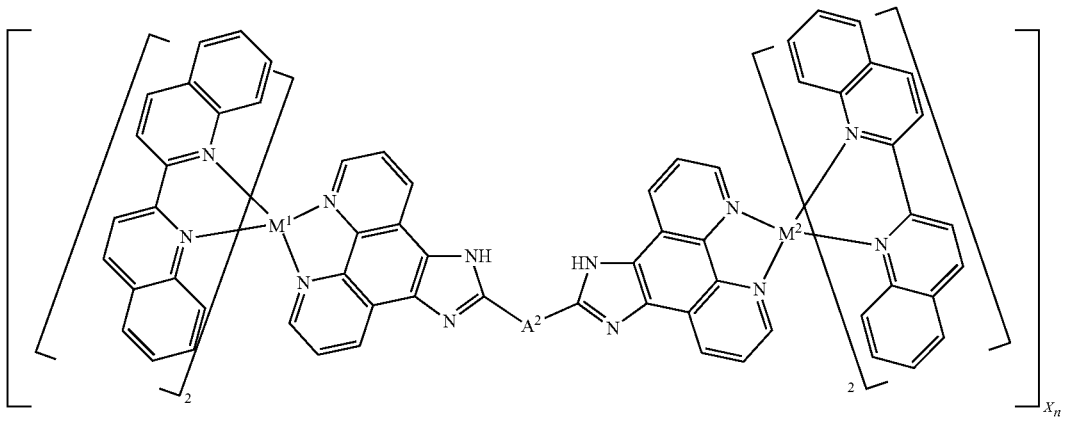

(XII)

wherein non-limiting examples of M, Lig, t, X, and q are defined herein below in Table 6.

TABLE 6

| Entry | M¹ | M² | A² | X | n |
|---|---|---|---|---|---|
| 1 | Os | Os | (thiophene with R$^{4a}$, R$^{4b}$)$_t$ | Cl | 4 |
| 2 | Os | Os | 1,4-phenylene | Cl | 4 |
| 3 | Os | Os | 1,3-phenylene | Cl | 4 |
| 4 | Os | Os | 1,2-phenylene | Cl | 4 |
| 5 | Os | Os | naphthalene-1,4-diyl | Cl | 4 |
| 6 | Os | Os | anthracene-9,10-diyl | Cl | 4 |
| 7 | Os | Os | pyrene-2,7-diyl | Cl | 4 |
| 8 | Os | Os | pyrazine-2,5-diyl | Cl | 4 |
| 9 | Os | Os | thiophene-2,4-diyl | Cl | 4 |
| 10 | Os | Os | thiophene-2,3-diyl | Cl | 4 |
| 11 | Os | Os | (thiophene with R$^{4a}$, R$^{4b}$)$_t$ | PF$_6$ | 4 |
| 12 | Os | Os | 1,4-phenylene | PF$_6$ | 4 |
| 13 | Os | Os | 1,3-phenylene | PF$_6$ | 4 |
| 14 | Os | Os | 1,2-phenylene | PF$_6$ | 4 |
| 15 | Os | Os | naphthalene-1,4-diyl | PF$_6$ | 4 |
| 16 | Os | Os | anthracene-9,10-diyl | PF$_6$ | 4 |
| 17 | Os | Os | pyrene-2,7-diyl | PF$_6$ | 4 |
| 18 | Os | Os | pyrazine-2,5-diyl | PF$_6$ | 4 |

TABLE 6-continued

| Entry | M¹ | M² | A² | X | n |
|---|---|---|---|---|---|
| 19 | Os | Os | (thiophene linker) | PF$_6$ | 4 |
| 20 | Os | Os | (thiophene linker) | PF$_6$ | 4 |

Exemplary embodiments include compounds having the formula (XIII) or a pharmaceutically acceptable salt form thereof:

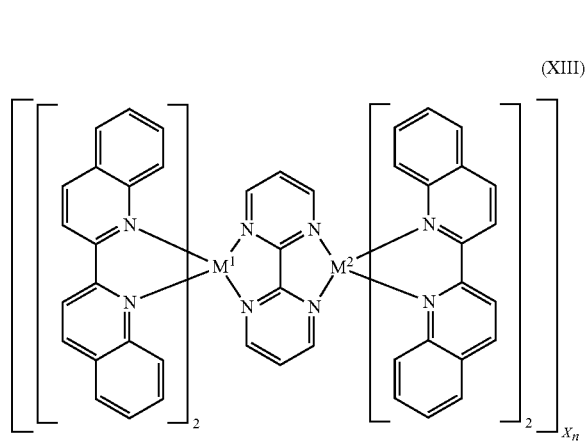

(XIII)

wherein non-limiting examples of M¹, M², X, and n are defined herein below in Table 7.

TABLE 7

| Entry | M¹ | M² | X | n |
|---|---|---|---|---|
| 1 | Os | Os | Cl | 4 |
| 2 | Os | Ru | Cl | 4 |
| 3 | Ru | Ru | Cl | 4 |
| 4 | Os | Os | PF$_6$ | 4 |
| 5 | Os | Ru | PF$_6$ | 4 |
| 6 | Ru | Ru | PF$_6$ | 4 |

Exemplary embodiments include compounds having the formula (XIV) or a pharmaceutically acceptable salt form thereof:

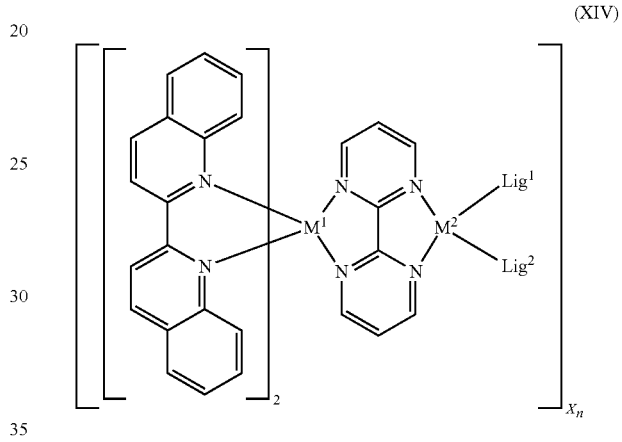

(XIV)

wherein non-limiting examples of M¹, M², Lig¹, Lig², X, and n are defined herein below in Table 8.

TABLE 8

| Entry | M¹ | M² | Lig¹ | Lig² | X | N |
|---|---|---|---|---|---|---|
| 1 | Os | Os | (4,4'-dimethyl-2,2'-bipyridine) | (imidazo-phenanthroline-terthiophene) | Cl | 4 |
| 2 | Os | Ru | (4,4'-dimethyl-2,2'-bipyridine) | (imidazo-phenanthroline-terthiophene) | Cl | 4 |

TABLE 8-continued
| Entry | M¹ | M² | Lig¹ | Lig² | X | N |
|---|---|---|---|---|---|---|
| 3 | Ru | Os | | | Cl | 4 |
| 4 | Os | Os | | | PF$_6$ | 4 |
| 5 | Os | Ru | | | PF$_6$ | 4 |
| 6 | Ru | Os | | | PF$_6$ | 4 |
Exemplary embodiments include compounds having the formula (XV) or a pharmaceutically acceptable salt form thereof:
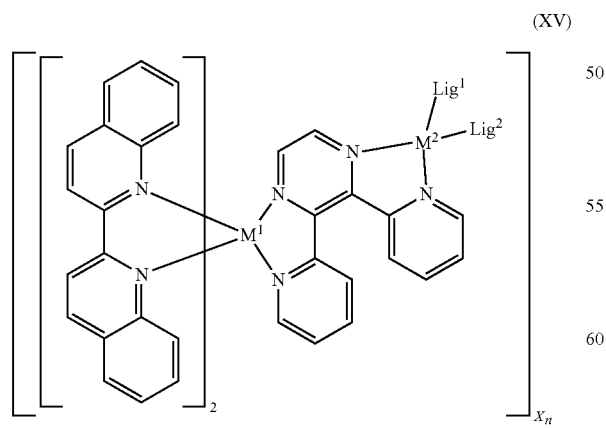
(XV)
wherein non-limiting examples of M¹, M², Lig¹, Lig², X, and n are defined herein below in Table 9.

TABLE 9
| Entry | M¹ | M² | Lig¹ | Lig² | X | N |
|---|---|---|---|---|---|---|
| 1 | Os | Os | | | Cl | 4 |
| 2 | Os | Ru | | | Cl | 4 |
| 3 | Ru | Ru | | | Cl | 4 |
| 4 | Os | Os | | | PF₆ | 4 |
| 5 | Os | Ru | | | PF₆ | 4 |
| 6 | Ru | Ru | | | PF₆ | 4 |
Exemplary embodiments include compounds having the formula (XVI) or a pharmaceutically acceptable salt form thereof:
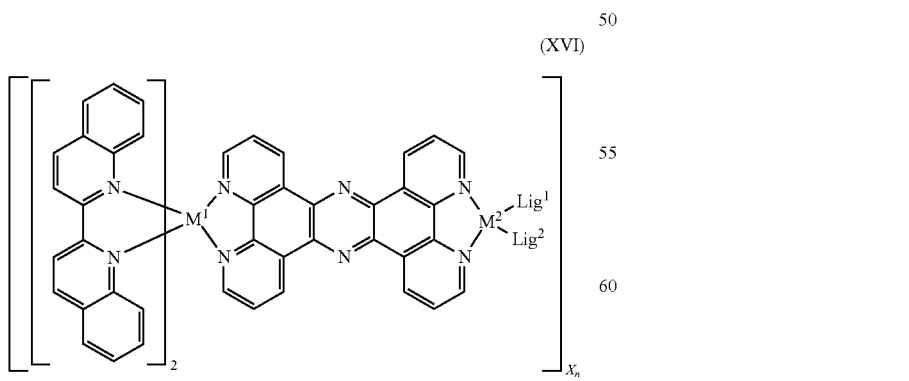
(XVI)
wherein non-limiting examples of M¹, M², Lig¹, Lig², X, and n are defined herein below in Table 10.

| Entry | M¹ | M² | Lig¹ | Lig² | X | n |
|---|---|---|---|---|---|---|
| 1 | Os | Os | | | Cl | 4 |
| 2 | Os | Ru | | | Cl | 4 |
| 3 | Ru | Ru | | | Cl | 4 |
| 4 | Os | Os | | | PF₆ | 4 |
| 5 | Os | Ru | | | PF₆ | 4 |
| 6 | Ru | Ru | | | PF₆ | 4 |
Exemplary embodiments include compounds having the formula (XVII) or a pharmaceutically acceptable salt form thereof:
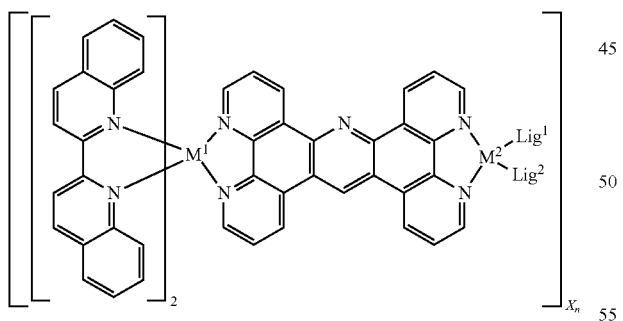
(XVII)
wherein non-limiting examples of M¹, M², Lig¹, Lig², X, and n are defined herein below in Table 11.
| Entry | M¹ | M² | Lig¹ | Lig² | X | n |
|---|---|---|---|---|---|---|
| 1 | Os | Os | | | Cl | 4 |

| Entry | M¹ | M² | Lig¹ | Lig² | X | n |
|---|---|---|---|---|---|---|
| 2 | Os | Ru | (structure) | (structure) | Cl | 4 |
| 3 | Ru | Ru | (structure) | (structure) | Cl | 4 |
| 4 | Os | Os | (structure) | (structure) | $PF_6$ | 4 |
| 5 | Os | Ru | (structure) | (structure) | $PF_6$ | 4 |
| 6 | Ru | Ru | (structure) | (structure) | $PF_6$ | 4 |

For the purposes of the present invention, a compound depicted by the racemic formula will stand equally well for either of the two enantiomers or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Properties of the compounds of the invention:

With the serendipitous discovery of cisdiamminodichloroplatinum(II), i.e., cisplatin, and its unprecedented success as an anticancer chemotherapeutic, metallopharmaceuticals as anticancer agents have garnered considerable attention although few have been approved for clinical use. Complexes derived from gold, iron, and ruthenium have been reported to possess anticancer activity, and two organometallic complexes of ruthenium (Imidazolium [trans-tetrachloro(1H-imidazole)(S-dimethylsulfoxide)ruthenate(III)], NAMI-A and indazolium [trans-tetrachlorobis(1H-indazole)ruthenate(III)], KP1019) are currently in clinical trials (Alessio, E.; Mestroni, G.; Bergamo, A.; Sava, G. Current Topics in Medicinal Chemistry 2004, 4, 1525-1535. Hartinger, C. G.; Zorbas-Seifried, S.; Jakupec, M. A.; Kynast, B.; Zorbas, H.; Keppler, B. K. Journal of Inorganic Biochemistry 2006, 100, 891-904). In contrast, metallopharmaceuticals derived from the third-row transition metal osmium remain largely unexplored ((a) Ni, W.-X.; Man, W.-L.; Cheung, M. T.-W.; Sun, R. W.-Y.; Shu, Y.-L.; Lam, Y.-W.; Che, C.-M.; Lau, T.-C. Chemical Communications 2011, 47, 2140-2142. (b) Kostrhunova, H.; Florian, J.; Novakova, O.; Peacock, A. F. A.; Sadler, P. J.; Brabec, V. Journal of Medicinal Chemistry 2008, 51, 3635-3643), most likely due to a perceived reputation for being highly toxic (e.g., $OsO_4$) and substitutionally inert ($Os^{2+}$, $Os^{3+}$). Recently organometallic complexes based on an Os(II) arene motif have shown potent in vitro cytotoxic and anti-metastatic properties, but this activity did not translate to anticancer activity in vivo (Bergamo, A.; Masi, A.; Peacock, A.; Habtemariam, A.; Sadler, P.; Sava, G. Journal of Inorganic Biochemistry 2010, 104, 79-86). To date, only high-valent nitridoosmium(VI) Schiff bases have shown promise in vivo. Together these preliminary studies regarding Os-based complexes highlight several salient points: (i) potent cytotoxicity in vitro does not lead a priori to in vivo anticancer activity, (ii) there are some high-valent Os-based complexes that exhibit potent cytotoxicity in vitro that translates to tumor-suppression in vivo, and (iii) most importantly, not all Os-based compounds display dose-limiting host toxicity. To date, there exist no examples of metal based coordination complex based photodynamic compounds (PDCs) that have successfully demonstrated in vitro or in vivo PDT effects. (Ni, W.-X.; Man, W.-L.; Cheung, M. T.-W.; Sun, R. W.-Y.; Shu, Y.-L.; Lam, Y.-W.; Che, C.-M.; Lau, T.-C. Chemical Communications 2011, 47, 2140-2142. Kostrhunova, H.; Florian, J.; Novakova, O.; Peacock, A. F. A.; Sadler, P. J.; Brabec, V. Journal of Medicinal Chemistry 2008, 51, 3635-3643. Bergamo, A.; Masi, A.; Peacock, A.; Habtemariam, A.; Sadler, P.; Sava, G. Journal of Inorganic Biochemistry 2010, 104, 79-86).

The compounds of the disclosure described herein are the first examples of the use of simple, metal-based coordination complexes as photodynamic compounds (PDCs) useful for the treatment and diagnosis of disease states, particularly for the destruction of infectious organisms, hyperproliferating cells, and tumor cells. The compounds of the disclosure (i) are metal-based coordination complexes, (ii) absorb ultraviolet (UV), visible, and infrared (IR) (particularly, near infrared (NIR)) light and are activated by wavelengths from UV to IR, particularly >800 nm, (iii) kill human cancer cells in culture and in animals, and (iv) destroy bacteria and antibiotic-resistant bacteria.

Compounds using the organic constructs described herein and employing the metals osmium, manganese, molybdenum, rhenium, ruthenium, iron, cobalt, rhodium, iridium, nickel, platinum, palladium, vanadium, chromium, tungsten, technetium, and copper are also capable of acting as PDT agents, are useful for the treatment and diagnosis of disease states, particularly for the destruction of infectious organisms, hyperproliferating cells, and tumor cells, and are included in the compounds of the disclosure.

Compounds of the disclosure are water-soluble, saline soluble and water-insoluble PDT agents. The water solubility, saline solubility and lipophilicity of said compounds can be tuned by altering the substituents. Complexes with structures (b) and (c) in FIG. 1 lack significant hydrophobicity and, consequently, are water-soluble while structures (a), (d), and (e) are water-insoluble. Water-soluble compounds can be made more lipophilic and lipophilic compounds can be made hydrophilic by structural modifications, judicious choice of solvents, dilutions, excipients, and the like.

Compounds of the disclosure are useful as tumor-targeting PDT agents. The hydrophobicity, hydrophilicity, lipophilicity, and tumor retention of compounds of the disclosure can be controlled by altering the substituents. Inclusion of at least one thiophene-appended imidazo[4,5-f][1,10] phenanthroline ligand (structure (a) in FIG. 1) leads to tumor-retention in a murine subcutaneous model of colon cancer of at least 4 hours. The number of thiophone units in the imidazo[4,5-f][1,10]phenanthroline ligand can be manipulated to control water-solubility versus tumor-retention (structures (a), (e), and (f) in FIG. 1).

Figure 2:
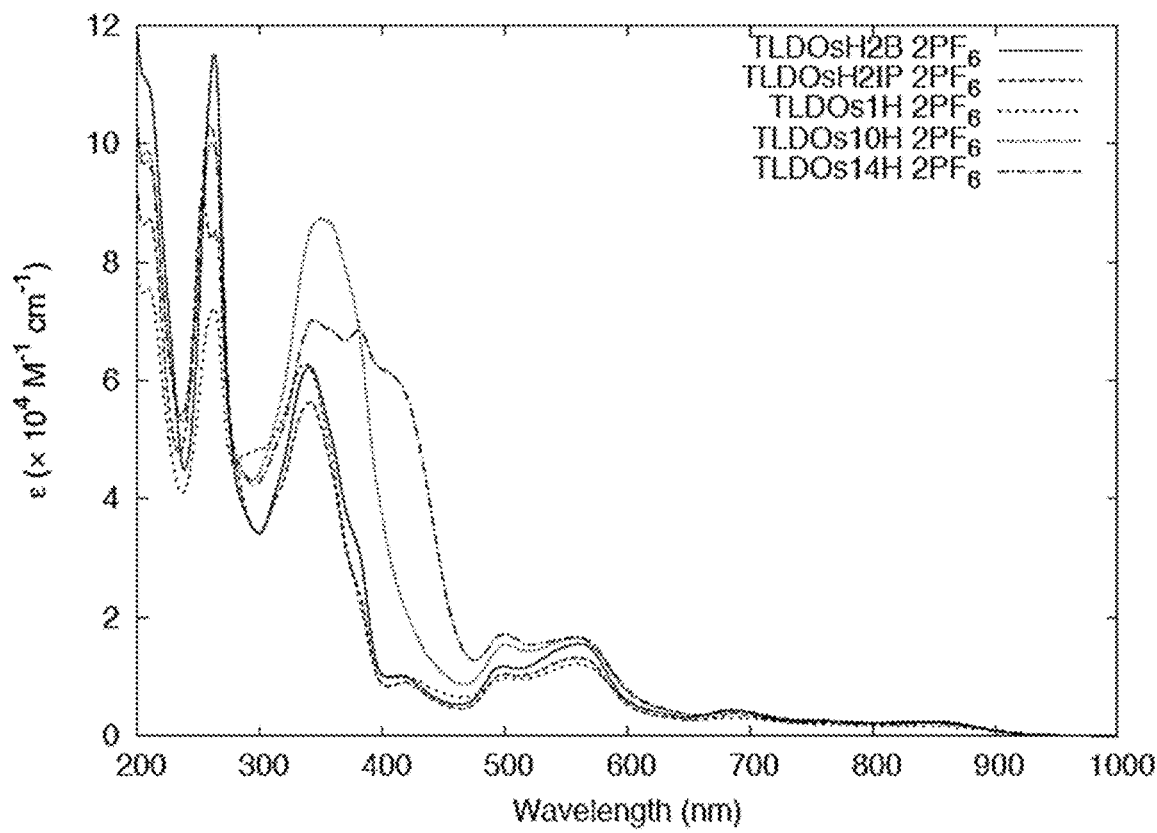
FIG. 2: UV-NIR absorption by exemplary compounds of the disclosure using a Jasco V530 UV-Vis spectrometer and Spectra Manager software.

Compounds of the disclosure absorb light from UV through IR light, particularly the near IR light (FIG. 2) and are useful as photodynamic therapy agents. The diimine ligand 2,2'-biquinoline ("biq") provides NIR-absorbing capacity to the compounds of the disclosure, while the identity of the remaining ligands can be altered to control both the physical and pharmacokinetic properties of the complex as well as its mechanism of action for PDT agents of the disclosure.

Compounds of the disclosure are nontoxic to cells, even at concentrations exceeding 100 uM. Further, compounds of the disclosure exhibit a strong PDT effect with increasing light dose (FIG. 3), even at low effective concentrations of 0.8 uM. Relative to the clinical agent ALA, these compounds are much more stable (FIGS. 4, 5) and exhibit stronger photon absorption. The compounds exhibit the ability to act as Type 1 or Type 2 PDT agents depending on the combination of ligands chosen, where Type 1 photochemistry involves the generation of radicals such as the highly toxic hydroxyl radical and Type 2 photochemistry involves singlet oxygen sensitization by the PDT agent. These contrasting mechanisms of action can be probed by including scavengers of the respective reactive oxygen species in the PDT experiment and noting whether the PDT effect is diminished or eliminated; for example, elimination of PDT in the presence of a scavenger for hydroxyl radical signals that hydroxyl radical is involved in the mechanism of action. Compounds of this class described in the present invention exhibit a spectrum of activities that range from pure Type 1 to pure Type 2 and also with elements of both.

Figure 6:
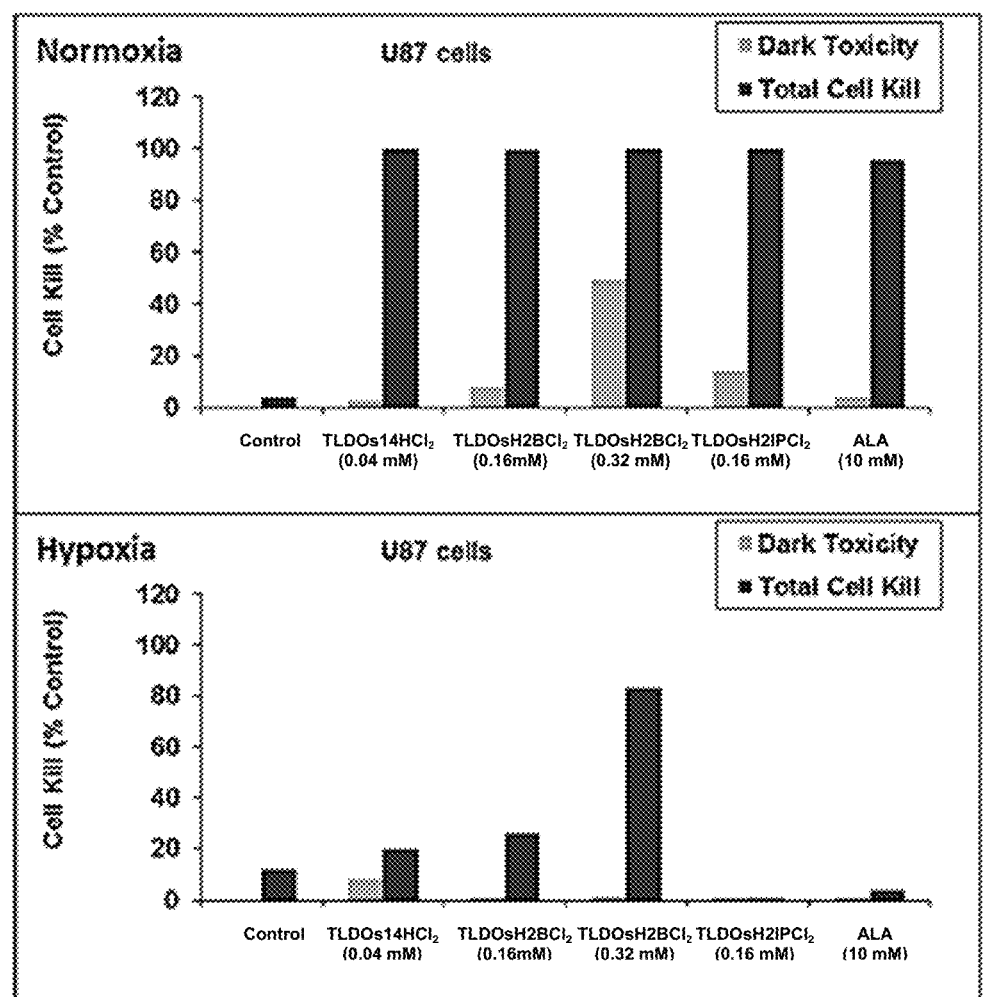
FIG. 6: Experimental evidence for in vitro PDT in normoxia (TLDOsH2B $Cl_2$, TLDOsH2IP $Cl_2$, and TLDOs14H $Cl_2$) and in hypoxia (TLDOsh2b $Cl_2$>TLDOs14h $Cl_2$>TLDOs2IP $Cl_2$). Hypoxic conditions refer to an environment approximately 0.1-0.5% in oxygen. The effects of TLDOs14H $Cl_2$ (40 µM), TLDOsH2B $Cl_2$ (160 and 320 µM), TLDOshH2IP $Cl_2$ (100 µM) and 12.5 mM ALA (used as an oxygen-sensitive positive control) without light (gray bars) and with light (black bars) on cell kill are expressed as a percentage of control (no PS, no light). Light dose: 635 nm, 90 $J \cdot cm^{-2}$.

The ligands of the compounds of the disclosure can be varied (i) to obtain both water-soluble and water-insoluble formulations that readily penetrate cellular membranes and (ii) to switch activity between normoxia and hypoxia (FIG. 6). The compounds of the disclosure, acting as photosensitizers, bind DNA directly, inducing high levels of DNA condensation and subsequent apoptosis, and are able to produce a sufficient therapeutic amount of singlet oxygen and hydroxyl radicals (reactive oxygen species, ROS, FIG. 7), thereby killing microbial and cancer cells even in hypoxic environments.

The compounds of the disclosure are nontoxic to cells but display potent photocytotoxicity toward cancer cells and microorganisms and can be used to generate the PDT effect (FIGS. 8, 9) useful for the treatment of disease associated with cellular hyperproliferation, such as cancer, including but not limited to breast cancer, colon cancer, brain cancer, melanoma, leukemia, and bladder cancer, and the destruction of microorganisms, bacteria, viruses, protozoa and fungi.

Established clinical agents for PDT possess respectable singlet oxygen quantum yields, indicating a high probability that in vivo PDT relies, at least in part, on the production of singlet oxygen. The compounds of the disclosure, surprisingly, exhibit very low singlet oxygen quantum yields at all excitation wavelengths (Table 1). While it is not surprising that sensitization of singlet oxygen by one-photon absorption would fail in the phototherapeutic window (780-950 nm), owing to low-photon energy (Starkey, J. R.; Rebane, A. K.; Drobizhev, M. A.; Meng, F.; Gong, A.; Elliott, A.; McInnerney, K.; Spangler, C. W. Clinical Cancer Research 2008, 14, 6564-6573), the low singlet oxygen quantum yields at shorter wavelengths is unexpected given the potent PDT observed in vitro and in vivo with compounds of the disclosure. Therefore, superoxide, hydrogen peroxide, and hydroxyl radicals may account for the acute oxidative burst of ROS but secondary reactive nitrogen species (RNS) may also play an important role (Coleman, J.; Scherz, A., European Urological Review, 2012; 7(2):106-8). Photothermal effects have not been ruled out.

TABLE 1

Singlet oxygen quantum yields of exemplary compounds of the disclosure.

| Photosensitizer | 480 nM $\Phi_\Delta$ | 532 nM | 808 nM |
|---|---|---|---|
| TLDOsH2B 2PF6 | 5.5% | 3.5% | <3% |
| TLDOsH2IP 2PF6 | 3.3% | 4.4% | <3% |
| TLDOsH2H 2PF$_6$ | 4.3% | 4.0% | <3% |
| TLDOs10H 2PF$_6$ | 3.2% | 3.5% | <3% |
| TLDOs14H 2PF$_6$ | 3.5% | 3.0% | <3% |

Embodiments of the disclosure produce emission at wavelengths >800 nm, and the quantum yields for emission increase by less than a factor of two in degassed or argon-purged solution. This minimal oxygen dependence and long wavelength output can be useful for diagnostic purposes, specifically in medical applications ((a) Starkey, J. R.; Rebane, A. K.; Drobizhev, M. A.; Meng, F.; Gong, A.; Elliott, A.; McInnerney, K.; Spangler, C. W. Clinical Cancer Research 2008, 14, 6564-6573. (b) Cullander, C. The Journal of Investigative Dermatology. Symposium Proceedings/ the Society for Investigative Dermatology, Inc. [and] European Society for Dermatological Research 1998, 3, 166-171). Additionally, the deeply pigmented compounds can be used as colorimetric indicators for cancer cells and tissue (FIG. 10) as indicated by the high rention of compounds of the disclosure by cancers cells.

Figure 11:
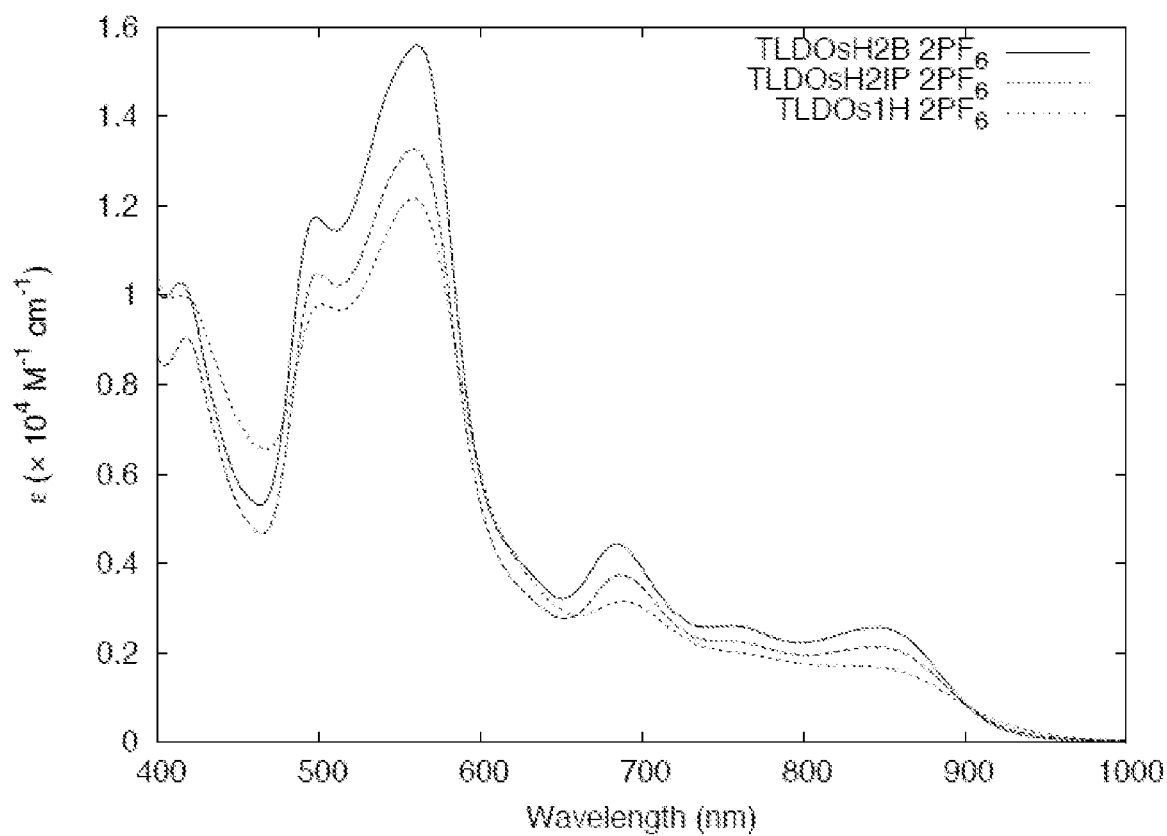
FIG. 11: Visible-NIR absorption profiles for photosensitizers of the general structure $[Os(biq)_2(LL)]Cl_2$, where biq=2,2'-biquinoline and LL=1,10-phenanthroline (TLDOsH2B $Cl_2$), imidazo[4,5-f][1,10]phenanthroline (TLDOsH2IP $Cl_2$), or 2-(2-(2"-thienyl)-imidazo[4,5-f][1,10]phenanthroline (TLDOs1H $Cl_2$) using a Jasco V530 UV-Vis spectrometer and Spectra Manager software.

Compounds of the disclosure have the ability to harvest low energy photons, expanding the spectral response well into the NIR region of the electromagnetic spectrum not available to previously described photosensitizers, making them useful in dye-sensitized solar cells (DSSCs). Embodiments of the disclosure exhibit both panchromatic absorption and high optical density (FIGS. 1 and 11, TLDOsH2B $Cl_2$). The 2,2'-biquinoline ligand of the compounds of the disclosure serve as aromatic n-delocalized ligand that enhance the oscillator strength of NIR spin-forbidden transitions by borrowing intensity from significantly red-shifted spin-allowed singlet-singlet transitions (Kinoshita, T.; Fujisawa, J.-i.; Nakazaki, J.; Uchida, S.; Kubo, T.; Segawa, H. J. Phys. Chem. Lett. 2012, 3, 394-398). Additional ligands are incorporated without significantly altering the NIR absorption signature of the model compound TLDOsH2B $Cl_2$. FIG. 11 demonstrates that 1,10-phenanthroline can be replaced by imidazo[4,5-f][1,10]phenanthroline (TLDOsH2IP $Cl_2$) or 2-(2"-thienyl)-imidazo[4,5-f][1,10] phenanthroline (TLDOs1H $Cl_2$), a photobiologically active compound useful as a PDT agents that can be activated with NIR light sources.

Figure 15:
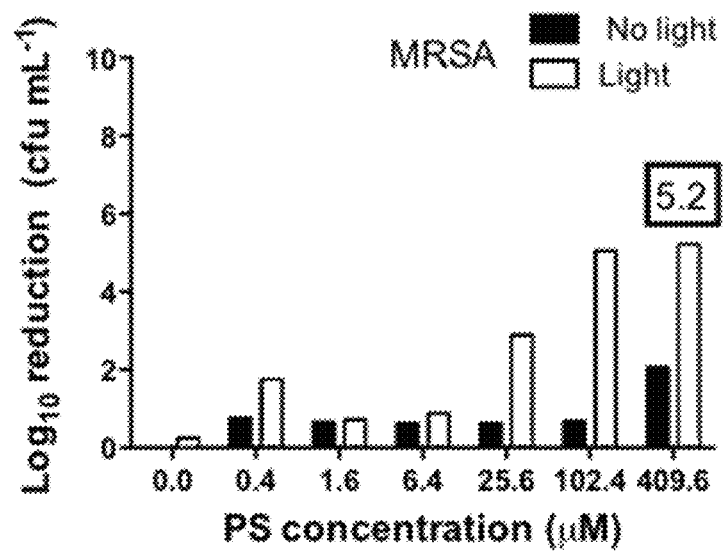
FIG. 15: Photodynamic inactivation (PDI) of methicillin-resistant S. aureus (MRSA) mediated by photosensitizers TLDOsH2IP $Cl_2$ (a) and TLDOsH2B $Cl_2$ (b). Maximum logs of kill achieved with a red light source were 5.2 and 4.6 for TLDOsH2IP $Cl_2$ and TLDOsH2B $Cl_2$, respectively.
Figure 15:
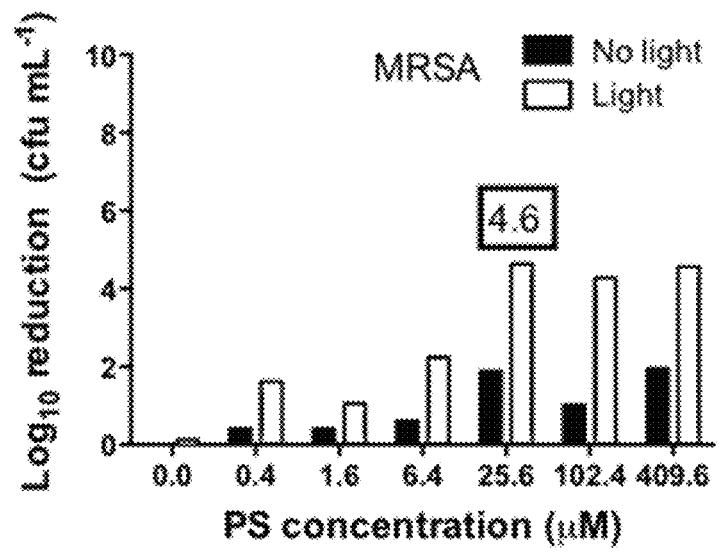

Compounds of the disclosure are also capable of destroying microorganisms, such as *Staphylococcus aureus* (SA) and methicillin-resistant *S. aureus* (MRSA), with activation by UV to IR light, particularly red and NIR light. As an example, activation of TLDOsH2IP $Cl_2$ (as low as 25 μM) with red light yielded substantial photodynamic inactivation of MRSA measured as $log_{10}$ reduction in colony forming units (cfu) per mL of bacterial solution. At peak concentrations, $log_{10}$ reductions of 5.2 and 4.6 were achieved with TLDOsH2IP $Cl_2$ and TLDOsH2B $Cl_2$, respectively (FIG. 15). Thus, photodynamic inactivation (PDI) mediated by this new class of photosensitizers has been demonstrated for a particularly opportunistic pathogen, and this photodynamic effect can be applied to both gram-positive and gram-negative bacteria (resistant and non-resistant) in various degrees of oxygen tension by judicious choice of the photosensitizer and its wavelength of activation.

Figure 16:
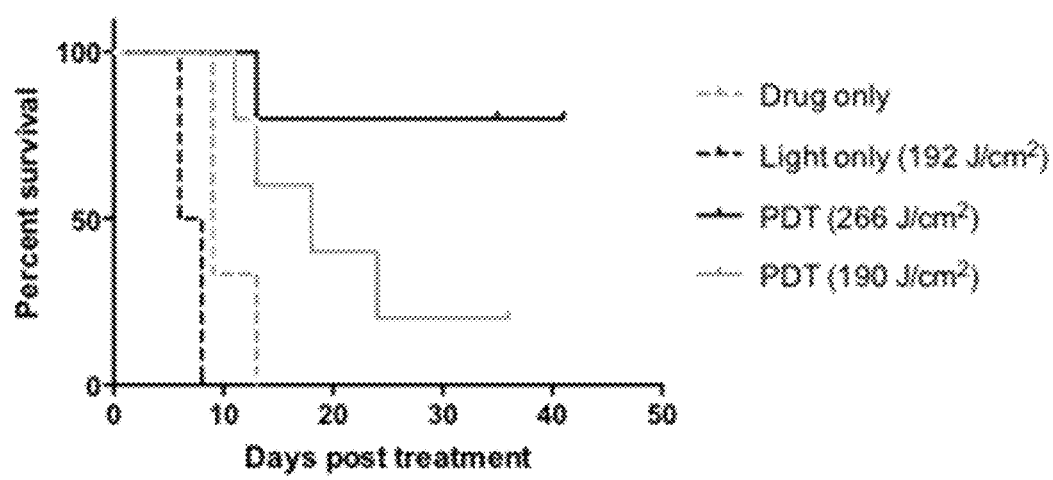
FIG. 16: Kaplan Meier survival curves for TLDOsH2IP $Cl_2$-mediated PDT with red light (635 nm, 100 $mW/cm^2$) in a subcutaneous adenocarcinoma mouse model of colon cancer. Animals were dosed with 3 mg/kg (1/6 $MTD_{50}$) prior to PDT at 190 $J/cm^2$ or 266 $J/cm^2$. Control mice receiving light treatment only or photosensitizer only are included for comparison.

Compounds of the disclosure are also capable of increasing survival time in mice bearing adenocarcinoma colon tumors with activation by irradiation at the appropriate wavelength. Exemplary results with compounds of the disclosure are shown in FIG. 16. TLDOsH2IP $Cl_2$-mediated PDT with red light (635 nm) at 190 or 266 $J/cm^2$ was performed on mice (CT26CL25 immunogenic type) bearing subcutaneous adenocarcinoma colon tumors. FIG. 16 contains Kaplan Meier survival curves demonstrating that light or photosensitizer alone do not lead to prolonged animal survival. However, mice treated with light plus photosensitizer experience prolonged survival, and this survival increases with increasing light dose. When TLDOsH2IP $Cl_2$ is activated by 266 $J/cm^2$ of red light, long term survival of the animals is evident in over 80% of the population. Therefore, the class of compounds described in this invention hold promise as therapeutic tools for cancer treatment (and destruction of unwanted cells in general, such and microorganisms and viruses).

Compounds of the disclosure are also have immune-modulating function, whereby in vivo PDT treatment has been used to mediate rejection of secondary tumors. PDT-treated mice were rechallenged with CT26.CL25 (antigenic) cells that express a tumor antigen and no tumors resulted. In control mice that did not receive previous PDT treatment, tumor regrowth was reported as early as 4 days in all mice. Hence, PDT with compounds of this invention may modify cellular immune responses that lead to systemic, antigen-specific anti-tumor immunity.

Process

The present invention further relates to a process for preparing the compounds of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and coordination complexes and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic and inorganic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., 1H or 13C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic and inorganic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic and inorganic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of formula (5) may be prepared according to the process outlined in the following schemes.

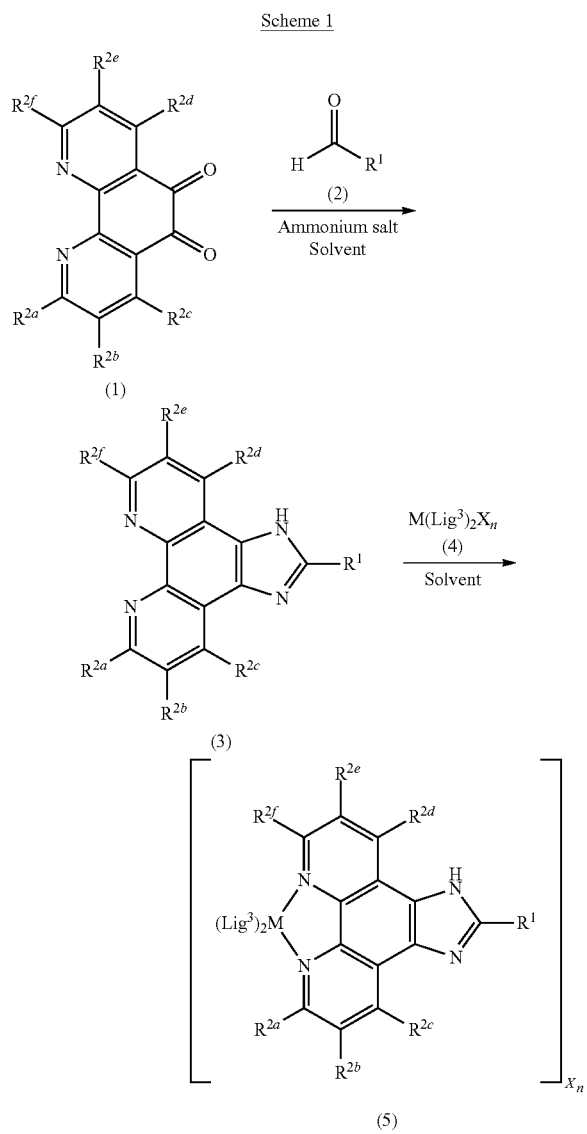

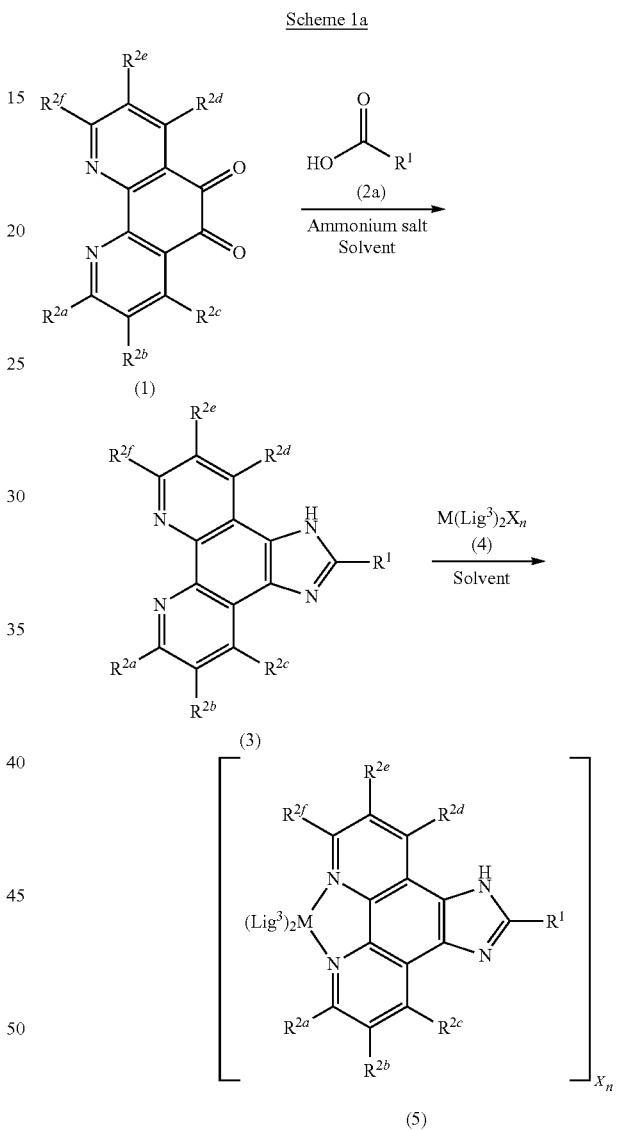

Accordingly, a suitably substituted compound of the formula (1), a known compound or compound prepared by known methods, is reacted with a suitably substituted compound of the formula (2) in the presence of an ammonium salt such as ammonium acetate, ammonium formate, ammonium chloride, ammonium bromide, ammonium sulfate and the like in a solvent such as acetic acid, formic acid, propionic acid and the like, optionally in the presence of methanol, ethanol, N,N-dimethylformamide and the like, optionally heated, optionally heated with microwave irradiation, to provide a compound of the formula (3). A compound of the formula (3) was then reacted with a compound of the formula (4) in a solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the formula (5). Compounds of the formula (5) may be converted to alternative salt forms by conventional methods known to those skilled in the art.

Alternatively, a suitably substituted compound of the formula (1), a known compound or compound prepared by known methods, is reacted with a suitably substituted compound of the formula (2a) in the presence of an ammonium salt such as ammonium acetate, ammonium formate, ammonium chloride, ammonium bromide, ammonium sulfate and the like in a solvent such as polyphosphoric acid, acetic acid, formic acid, propionic acid and the like, optionally in the presence of methanol, ethanol, N,N-dimethylformamide and the like, optionally heated, optionally heated with microwave irradiation, to provide a compound of the formula (3). A compound of the formula (3) was then reacted with a compound of the formula (4) in a solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the formula (5). Compounds of the formula (5) may be converted to alternative salt forms by conventional methods known to those skilled in the art.

Compounds of formula (7) may be prepared according to the process outlined in Scheme 2.

Scheme 2

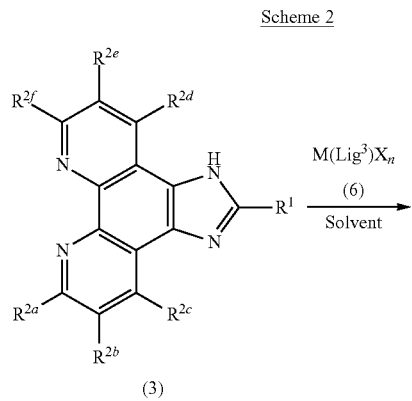

(3)

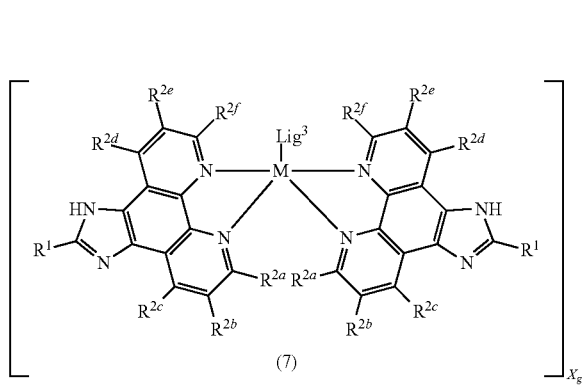

(7)

Accordingly, a suitably substituted compound of the formula (3) is reacted with a compound of the formula (6) in an a solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the formula (7). Compounds of the formula (7) may be converted to alternative salt forms by conventional methods known to those skilled in the art.

Compounds of formula (8) may be prepared according to the process outlined in Scheme 3.

Scheme 3

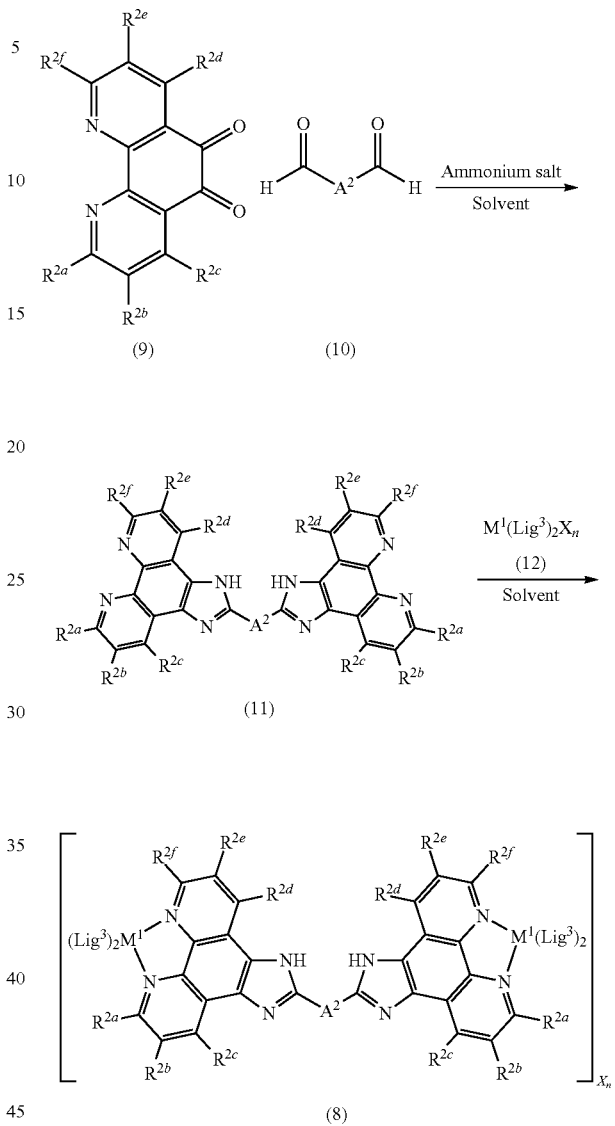

Accordingly, a suitably substituted compound of the formula (9), a known compound or compound prepared by known methods, is reacted with a suitably substituted compound of the formula (10) in the presence of an ammonium salt such as ammonium acetate, ammonium formate, ammonium chloride, ammonium bromide, ammonium sulfate and the like in a solvent such as acetic acid, formic acid, acid, propionic acid and the like, optionally in the presence methanol ethanol N,N-dimethylformamide and the like, optionally heated, optionally heated with microwave irradiation, to provide a compound of the formula (11). A compound of the formula (11) was then reacted with a compound of the formula (12) in a solvent such as methanol, ethanol, isopropanol, ethylene glycol, 1,2-dimethoxyethane, glycerol, water, 1,4-dioxane and the like, optionally heated, optionally heated with microwave irradiation, to provide a compound of the formula (8). Compounds of the formula (8) may be converted to alternative salt forms by conventional methods known to those skilled in the art.

Scheme 3a

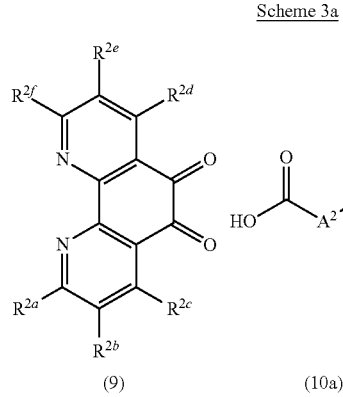

(9)    (10a)

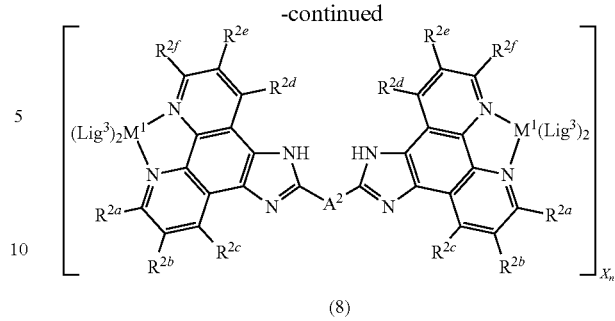

(8)

Alternatively, a suitably substituted compound of the formula (9), a known compound or compound prepared by known methods, is reacted with a suitably substituted compound of the formula (10a) in the presence of an ammonium salt such as ammonium acetate, ammonium formate, ammonium chloride, ammonium bromide, ammonium sulfate and the like in a solvent such as polyphosphoric acid, acetic acid, formic acid, acid, propionic acid and the like, optionally in the presence methanol, ethanol, N,N-dimethylformamide and the like, optionally heated, optionally heated with microwave irradiation, to provide a compound of the formula (11). A compound of the formula (11) was then reacted with a compound of the formula (12) in a solvent such as methanol, ethanol, isopropanol, ethylene glycol, 1,2-dimethoxyethane, glycerol, water, 1,4-dioxane and the like, optionally heated, optionally heated with microwave irradiation, to provide a compound of the formula (8). Compounds of the formula (8) may be converted to alternative salt forms by conventional methods known to those skilled in the art.

Compounds of formula (8a) may be prepared according to the process outlined in the following Scheme 3b.

Scheme 3b

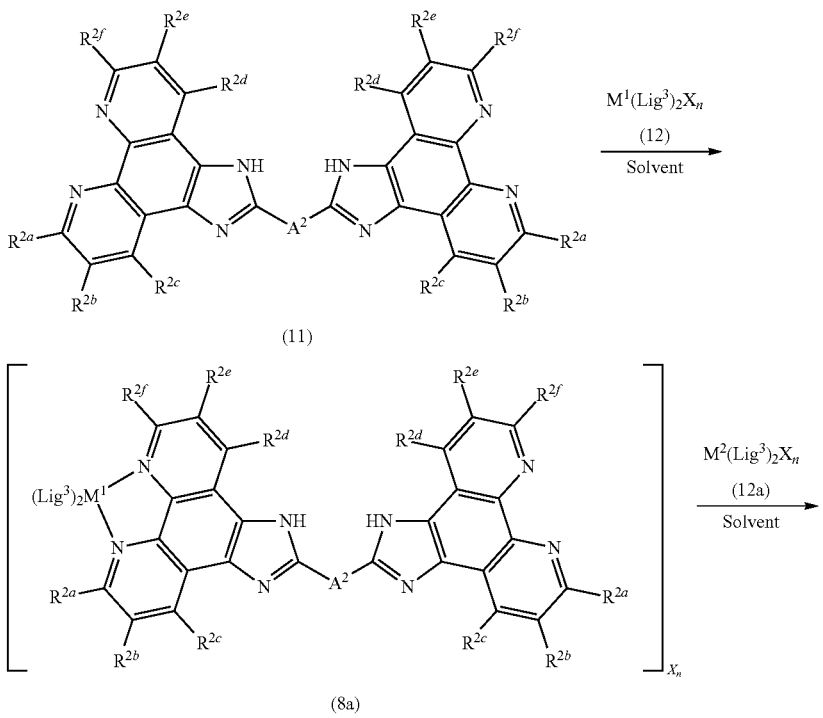

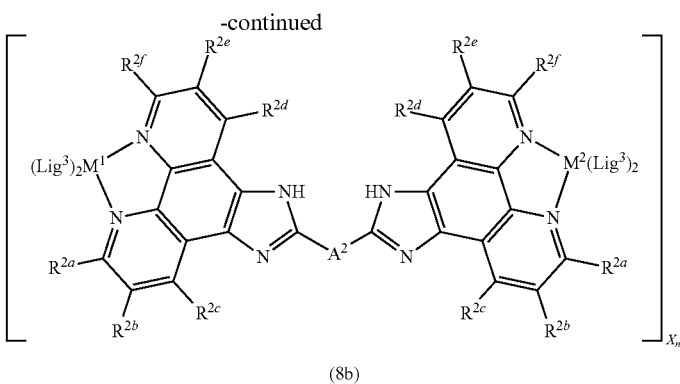

(8b)

A compound of the formula (11) was then reacted with a compound of the formula (12) in a solvent such as methanol, ethanol, isopropanol ethylene glycol, glycerol, water, 1,4-dioxane and the like, optionally heated, optionally heated with microwave irradiation, to provide a compound of the formula (8a). A compound of the formula (8a) was then reacted with a compound of the formula (12a) in a solvent such as methanol, ethanol, isopropanol, ethylene glycol, 1,2-dimethoxyethane, glycerol, water, 1,4-dioxane and the like, optionally heated, optionally heated with microwave irradiation, to provide a compound of the formula (8b). Compounds of the formula (8b) may be converted to alternative salt forms by conventional methods known to those skilled in the art.

Compounds of formula (8d) may be prepared according to the process outlined in the following Scheme 3c.

Scheme 3c

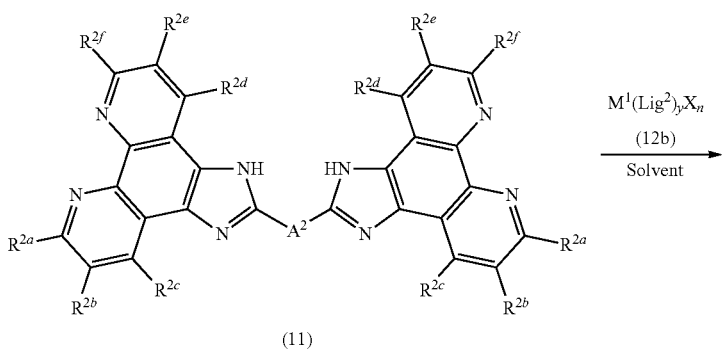

(11)

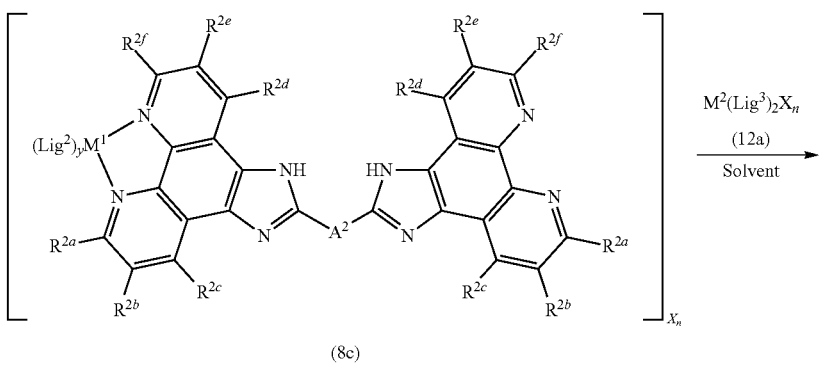

(8c)

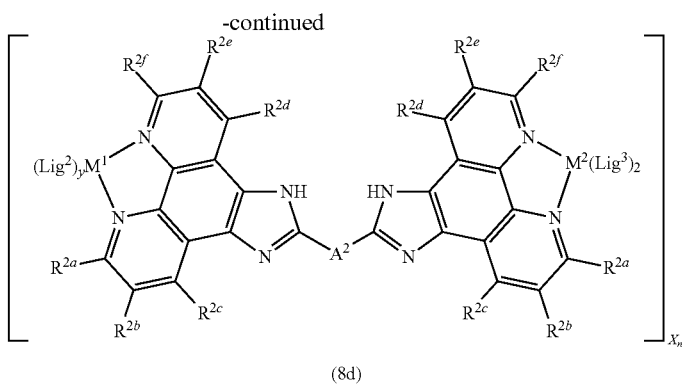

(8d)

A compound of the formula (11) was then reacted with a compound of the formula (12b) in a solvent such as methanol, ethanol, isopropanol, ethylene glycol, 1,2-dimethoxyethane, glycerol, water, 1,4-dioxane and the like, optionally heated, optionally heated with microwave irradiation, to provide a compound of the formula (8c). A compound of the formula (8c) was then reacted with a compound of the formula (12a) in a solvent such as methanol, ethanol, isopropanol, ethylene glycol, 1,2-dimethoxyethane, glycerol, water, 1,4-dioxane and the like, optionally heated, optionally heated with microwave irradiation, to provide a compound of the formula (8d). Compounds of the formula (8d) may be converted to alternative salt forms by conventional methods known to those skilled in the art.

Compounds of formula (8f) may be prepared according to the process outlined in the following Scheme 3d.

Scheme 3d

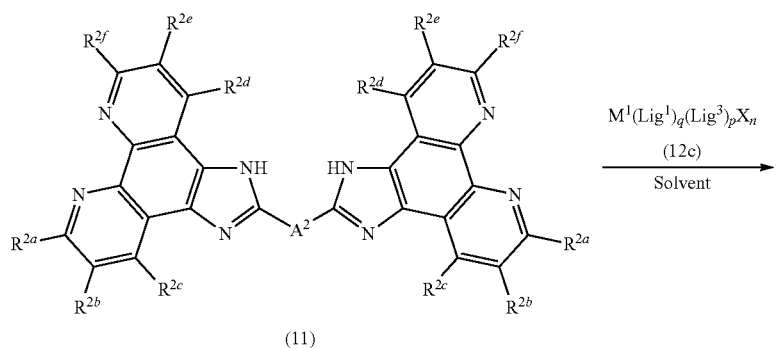

(11)

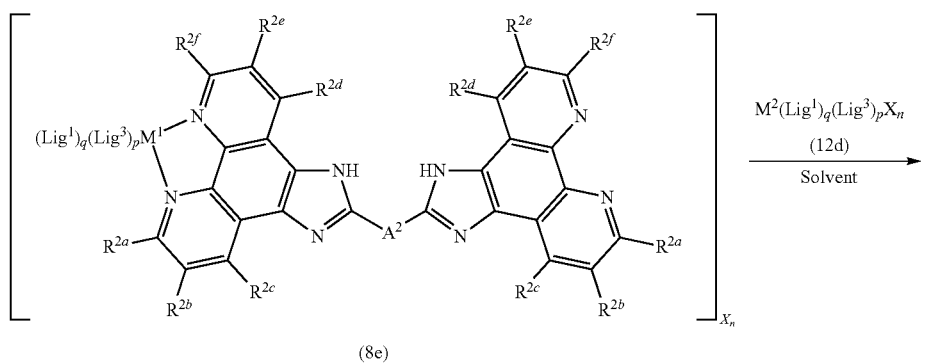

(8e)

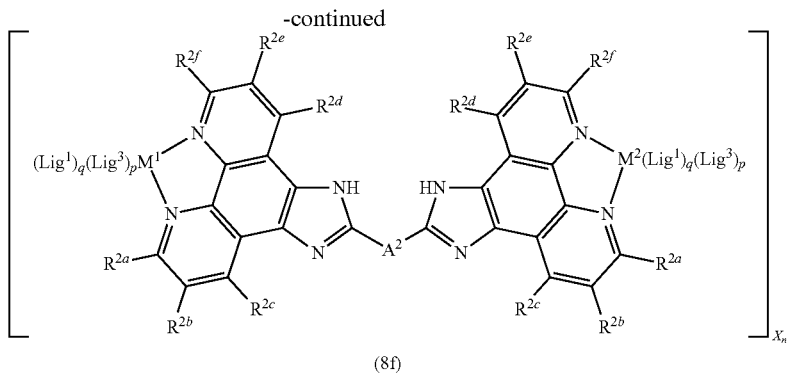

(8f)

A compound of the formula (11) is reacted with a compound of the formula (12c) in a solvent such as methanol, ethanol, isopropanol, ethylene glycol, 1,2-dimethoxyethane, glycerol, water, 1,4-dioxane and the like, optionally heated, optionally heated with microwave irradiation, to provide a compound of the formula (8e). A compound of the formula (8e) was then reacted with a compound of the formula (12d) in a solvent such as methanol, ethanol, isopropanol, ethylene glycol, 1,2-dimethoxyethane, glycerol, water, 1,4-dioxane and the like, optionally heated, optionally heated with microwave irradiation, to provide a compound of the formula (8f). Compounds of the formula (8f) may be converted to alternative salt forms by conventional methods known to those skilled in the art.

Compounds of formula (13) may be prepared according to the process outlined in the following Scheme 4.

Scheme 4

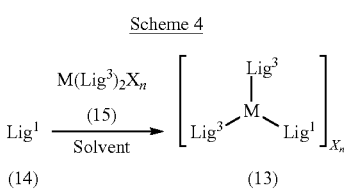

Accordingly, a suitably substituted compound of the formula (14), a known compound or compound prepared by known methods, was then reacted with a compound of the formula (15), a known compound or compound prepared by known methods, in a solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the formula (13). Compounds of the formula (13) may be converted to alternative salt forms by conventional methods known to those skilled in the art.

Compounds of formula (16) may be prepared according to the process outlined in Scheme 5.

Scheme 5

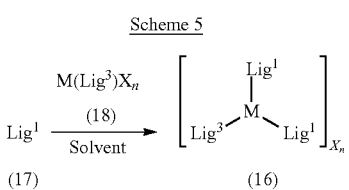

Accordingly, a suitably substituted compound of the formula (17) is reacted with a compound of the formula (18) in an a solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the formula (16). Compounds of the formula (16) may be converted to alternative salt forms by conventional methods known to those skilled in the art.

Compounds of formula (19) may be prepared according to the process outlined in Scheme 6.

Scheme 6

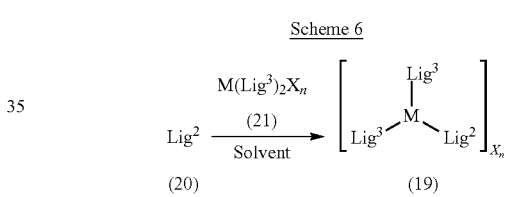

Accordingly, a suitably substituted compound of the formula (20), a known compound or compound prepared by known methods, was then reacted with a compound of the formula (21), a known compound or compound prepared by known methods, in a solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the formula (19). Compounds of the formula (19) may be converted to alternative salt forms by conventional methods known to those skilled in the art.

Compounds of formula (22) may be prepared according to the process outlined in Scheme 7.

Scheme 7

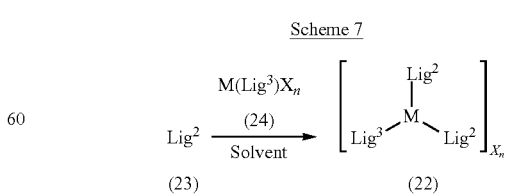

Accordingly, a suitably substituted compound of the formula (23), a known compound or compound prepared by known methods, is reacted with a compound of the formula (24), a known compound or compound prepared by known methods, in an solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the formula (22). Compounds of the formula (22) may be converted to alternative salt forms by conventional methods known to those skilled in the art.

Compounds of formula (25) may be prepared according to the process outlined in Scheme 8.

mula (27a). A compound of of the formula (27a) is then reacted with a compound of the formula (29), a known compound or compound prepared by known methods, in a solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the formula (25).

Compounds of formula (28) may be prepared according to the process outlined in Scheme 10.

Scheme 8

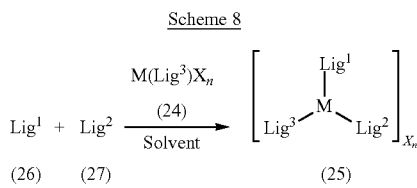

Scheme 10

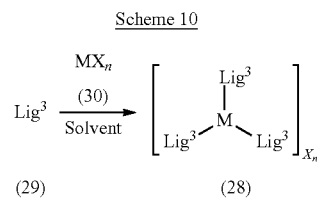

Accordingly, a suitably substituted compound of the formula (26), a known compound or compound prepared by known methods, and a suitably substituted compound of the formula (27), a known compound or compound prepared by known methods, are reacted with a compound of the formula (24) in an a solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the formula (25). Compounds of the formula (25) may be converted to alternative salt forms by conventional methods known to those skilled in the art.

Accordingly, a suitably substituted compound of the formula (29), a known compound or compound prepared by known methods, is reacted with a compound of the formula (30), a known compound or compound prepared by known methods, optionally in the presence of lithium chloride, in an a solvent such as methanol, ethanol, isopropanol, ethylene 1,2-dimethoxyethane, glycol, glycerol, water, 1,4-dioxane, dimethyl formamide, mixtures of the aforementioned solvents, and the like, optionally heated, optionally heated with microwave irradiation, to provide a compound of the formula (28). Compounds of the formula (28) may be converted to alternative salt forms by conventional methods known to those skilled in the art.

Compounds of formula (31) may be prepared according to the process outlined in Scheme 11.

Scheme 9

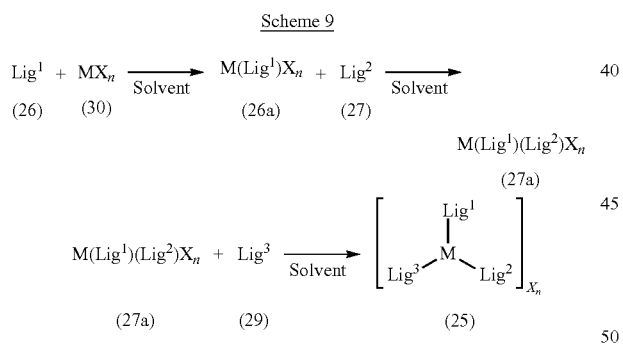

Scheme 11

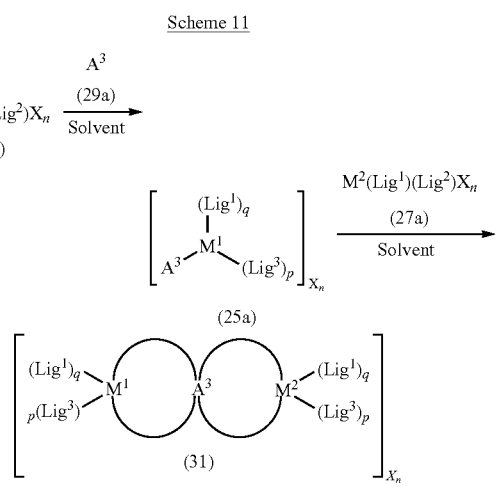

Alternatively, a suitably substituted compound of the formula (26), a known compound or compound prepared by known methods, is reacted with a compound of the formula (30) in a solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the formula (26a). A compound of of the formula (26a) is then reacted with a compound of the formula (27), a known compound or compound prepared by known methods, in a solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the for- A compound of of the formula (27a) is reacted with a compound of the formula (29a), a known compound or compound prepared by known methods, in a solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the formula (25a). A compound of of the formula (25a) is then reacted with a compound of the formula (27a), a known compound or compound prepared by known methods, in a solvent such as methanol, ethanol, isopropanol, ethylene glycol, 1,2-dimethoxyethane, glycerol, water, 1,4-dioxane, dimethyl formamide, mixtures of the aforementioned solvents, and the like, optionally heated, optionally heated with microwave irradiation, to provide a compound of the formula (31). Compounds of the formula (31) may be converted to alternative salt forms by conventional methods known to those skilled in the art.

The invention will be illustrated in more detail with reference to the following Examples, but it should be understood that the present invention is not deemed to be limited thereto.

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

$^1$H-NMR spectra were obtained on a Bruker Avance 300-MHz NMR. Low and high resolution mass spectral data were determined with a Bruker Daltonics micrOTOF instrument.

Examples

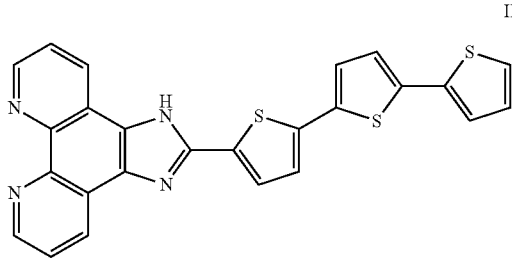

IP-TT

Preparation of 2-(2',2":5",2'''-terthiophene)-imidazo[4,5-f][1,10]phenanthroline (IP-TT): 10-Phenanthroline-5,6-dione (166.6 mg, 0.800 mmol), ammonium acetate (616 mg, 8.00 mmol), and 5-formyl-2,2':5',2"-terthiophene (221.12, 0.800 mmol) were combined with glacial acetic acid (4.0 mL) in a microwave reaction chamber and reacted with 300 W at 180° C. for 10 minutes. The solution changed from a light yellow colour to a deep red colour and was allowed to cool to room temperature. The solution was neutralized by drop-wise addition of aqueous NH$_4$OH (6 mL) until the product precipitated out as a yellow/brown solid. The solid was collected using a fine glass-sintered frit filter and washed with H$_2$O (15 mL). The product was dried under vacuum to give a tan powder. (256 mg, 69%). R$_f$=(2% H$_2$O, 43% CHCl$_3$, 25% Acetone, 30% MeOH+1% NH$_4$OH). $^1$H NMR (DMSO-d$_6$) 7.14 (dd; 1H; J=4.37 Hz), 7.33-7.43 (m; 4H), 7.55 (m; 1H), 7.75-7.79 (m; 3H), 8.82 (d; 2H; J=8.01 Hz), 8.97 (d; 2H; J=3.00 Hz).

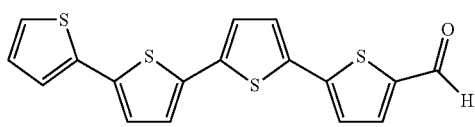

16x

Preparation of 16x: 2,2'-5,2''-Terthiophene-5-boronic acid pinicol ester (236.1 mg, 0.780 mmol), 5-bromo-2-thiophene carboxaldyde (57.4 uL, 0.59 mmol), and Pd(PPh$_3$)$_4$ (55 mg) were combined in an argon purged microwave tube. The microwave tube was again argon purged and 1,2-dimethoxyethane (5.66 mL) and 2M Na$_2$CO$_3$ aqueous solution (0.4 mL) were then added separately by syringe. The solution was reacted at 200 W and 175° C. for 1 hour. The dark green solution was filtered on a fine frit to remove the catalyst and washed with tiny amounts of ethyl acetate. The filtrate was diluted with additional EtOAc, transferred to a 125-mL separatory, and washed with saturated aqueous NaCl (3×50 mL). The organic layer was concentrated under reduced pressure, and dried under vacuum to give the crude product (130.9 mg, 62%). Purification was done on a silica column, eluting with 1:1 dichloromethane:hexanes. A slow moving spot that stained positive to have aldehyde by Dinitrophenylhydrazine was collected, concentrated under reduced pressure, and dried under vacuum to give the pure product (14.1 mg, 6.7%). R$_f$=0.20 (1:1 dichloromethane:hexanes). $^1$H NMR (CDCl$_3$) 9.86 (s; 1H), 7.67 (d; 1H; J=3.96 Hz), 7.21-7.29 (m; 3H), 7.20 (d; 1H; J=3.54 Hz), 7.11-7.14 (m; 3H), 7.04 (t; 1H; J=4.89 Hz).

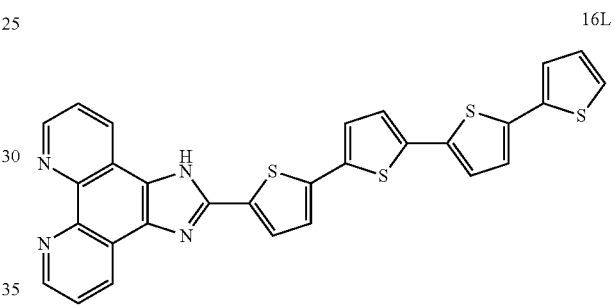

16L

Preparation of 16L: 1,10-Phenanthroline-5,6-dione (41.6 mg, 0.200 mmol), ammonium acetate (154 mg, 2.00 mmol), and 16x (71.7 mg, 0.200 mmol) were combined with glacial acetic acid (1.0 mL) in a microwave reaction chamber and reacted at 300 W at 180° C. for 10 minutes. The solution was allowed to cool to room temperature followed by neutralization by dropwise addition of aqueous NH$_4$OH (2-4 mL) until the product precipitated out as a brown solid. The solid was collected using a fine glass-sintered frit filter and washed with H$_2$O (15 mL). The product was dried under vacuum to give the crude product as a brown powder (105.9 mg, 96%). Purification was done by recrystallization from hot MeOH to give the pure product (31.1 mg, 28%). $^1$H NMR (DMSO-d6) 9.04 (br; 2H), 8.84 (d; 2H; J=7.35 Hz), 7.86 (br; 2H), 7.33-7.57 (m; 8H); 7.11 (br; 1H). MS (ESI+) m/z: 549.0 [M+1H]$^+$. HRMS (ESI+) m/z for C$_{29}$H$_{17}$N$_4$S$_4$; calcd 549.0331; found 549.0307.

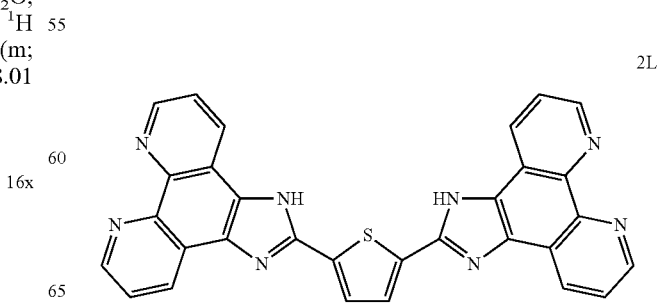

2L

Preparation of 2L: 1,10-Phenanthroline-5,6-dione (234.1 mg, 1.11 mmol), ammonium acetate (1.77 g, 23.0 mmol), and 2,5-thiophene dicarboxaldehyde (77.9 mg, 0.556 mmol) were combined in glacial acetic acid (20 mL) and refluxed in air at 135° C. for 6 hours. The solution changed from a light yellow colour to a deep red colour and the product precipitated as a light orange stringy precipitate. The reaction was cooled to room temperature. The orange precipitate was collected using a medium glass-sintered frit filter and washed with $H_2O$ (10 mL). The product was dried under vacuum to give the final pure product as a light orange powder. No purification was needed. (90.7 mg, 31.3%). $R_f$=streak to 0.60 (2% $H_2O$, 43% $CHCl_3$, 25% Acetone, 30% MeOH+1% $NH_4OH$). $^1H$ NMR (300 MHz) [$(CD_3)_2SO$]: 9.07 (d; 4H; J=3.03 Hz), 8.90 (d; 4H; J=8.22 Hz), 8.04 (s; 2H), 7.86-7.90 (br; 4H). MS (ESI+) m/z: 521.1 [M+H]$^+$. HRMS (ESI+) m/z for $C_{30}H_{17}N_8S$; calcd 521.1291; found 521.1265.

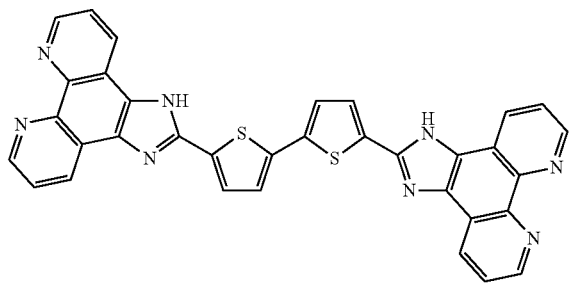

3L

Preparation of 3L: 1,10-Phenanthroline-5,6-dione (18.9 mg, 0.0900 mmol), ammonium acetate (138.7 mg, 1.80 mmol), and 2,2'-bithiophene-5,5'-dicarbaldehyde (10 mg, 0.0450 mmol) were combined in glacial acetic acid (5 mL) and refluxed in air at 135° C. for 6 hours. The solution changed from a light yellow colour to a deep red colour and the product precipitated as a light orange precipitate powder. The reaction was cooled to room temperature. The solution was neutralized by drop-wise addition of aqueous $NH_4OH$ (5 mL) until more desired product finished precipitating out as an orange solid. The orange precipitate was collected using a fine glass-sintered frit filter and washed with $H_2O$ (10 mL). The product was dried under vacuum to give an orange powder which showed the product and contaminant by NMR. (12.6 mg, 47%). An alternate microwave synthesis was also performed involving 1,10-Phenanthroline-5,6-dione (18.9 mg, 0.0900 mmol), ammonium acetate (138.7 mg, 1.80 mmol), and 2,2'-bithiophene-5,5'-dicarbaldehyde (10 mg, 0.0450 mmol) being combined in glacial acetic acid (1.0 mL) in a microwave reaction chamber and reacted with with 300 W at 180° C. for 10 minutes. The solution changed from a light yellow colour to a deep red colour and was allowed to cool to room temperature. An orange precipitate of the product was seen. The solution was neutralized by drop-wise addition of aqueous $NH_4OH$ (1 mL) until more desired product finished precipitating out as an orange solid. The solid was collected using a fine glass-sintered frit filter and washed with $H_2O$ (10 mL). The product was dried under vacuum to give an orange powder which showed the product and contaminant by NMR. (25.3 mg, 93%) $R_f$=streak to 0.68 (2% $H_2O$, 43% $CHCl_3$, 25% Acetone, 30% MeOH+1% $NH_4OH$). $^1H$ NMR (300 MHz) [$(CD_3)_2SO$]: 9.02 (br), 8.85 (br; 4H), 7.84 (m; 2H), 7.70 (br).

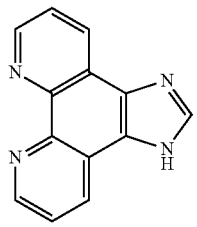 [SMILES: c1cnc2c(c1)c1nc[nH]c1c1cccnc12]

Preparation of imidazo[4,5-f][1,10]phenathroline (IP): [1,10]phenanthroline[5,6]dione (525 mg, 2.5 mmol) was combined with formaldehyde (0.243 mL of a 37% w/v solution, 3 mmol) and $NH_4OAc$ (3.85 g, 50 mmol)) in glacial HOAc (8 mL). The reaction was heated at reflux until all of the limiting reagent was consumed and cooled to room temperature. Dilution with water followed by neutralization with $NH_4OH$ gave a precipitate that was filtered and washed with water and then diethyl ether to yield light brown solid (504 mg, 91%). $^1H$ NMR (300 MHz, DMSO-$d_6$), δ (ppm): 13.75 (s, 1H), 9.03 (dd, 2H, $J_1$=4.3 Hz, $J_2$=1.5 Hz), 8.83 (dd, 2H, $J_1$=8 Hz, $J_2$=1.5 Hz), 8.47 (d, 1H), 7.83 (dd, 2H, $J_1$=8 Hz, $J_2$=4.3 Hz).

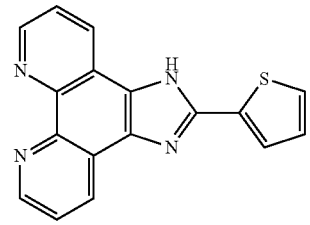 [SMILES: c1csc(-c2nc3c4cccnc4c4ncccc4c3[nH]2)c1]

Preparation of 2-(Thienyl)imidazo[4,5-f][1,10]phenanthroline (IP-T). 1,10-Phenanthroline-5,6-dione (42 mg, 0.62 mmol), ammonium acetate (154 mg, 2.0 mmol), and 2-thiophenecarboxaldehyde (18.3 mL, 0.20 mmol) were combined with glacial acetic acid (1 mL) in a microwave reaction chamber and reacted (300 W, 180° C.) for 10 minutes. The deep red solution was cooled to room temperature and neutralized by drop-wise addition of aqueous $NH_4OH$ until the product precipitated as a yellowish brown solid. The solid was collected using a fine glass-sintered frit and washed with $H_2O$. The product was dried under vacuum to give give a yellow powder (36.2 mg, 60%). $R_f$=Streaked to 0.77 (2% $H_2O$, 43% $CHCl_3$, 25% acetone, 30% MeOH+1% $NH_4OH$). $^1H$ NMR (300 MHz, DMSO-$d_6$) δ (ppm): 9.01 (d; 2H; J=1.89 Hz), 8.83 (d; 2H; J=7.89 Hz), 7.89 (s; 1H), 7.81 (br; 2H), 7.73 (s; 1H), 7.27 (s; 1H). MS (ESI+) m/z: 303.1 [M+H]$^+$. HRMS (ESI+) m/z for $C_{17}H_{11}N_4S$; calcd 303.0699; found 303.0706.

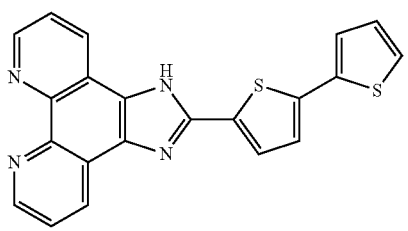 [SMILES: c1csc(-c2ccc(-c3nc4c5cccnc5c5ncccc5c4[nH]3)s2)c1]

Preparation of 2-(2',2''-Bithiophene)imidazo[4,5-f][1,10]phenanthroline (IP-BT). 1,10-Phenanthroline-5,6-dione (100 mg, 0.48 mmol), ammonium acetate (740 mg, 9.6 mmol), and 5-formyl-2,2'-bithiophene (112, 0.58 mmol) were combined with glacial acetic acid (10 mL) in a microwave reaction chamber and reacted (300 W, 180° C.) for 10 minutes. The deep red solution was cooled to room temperature and neutralized by drop-wise addition of aqueous $NH_4OH$ until the product precipitated as a yellow/brown solid. The solid was collected using a fine glass-sintered frit and washed with $H_2O$. The product was dried under vacuum to give an orange-brown solid (125 mg, 68%). $R_f$=0.33 (2% $H_2O$/43% $CHCl_3$/25% acetone/30% $CH_3OH$+1% $NH_4OH$). $^1H$ NMR (300 MHz, DMSO-$d_6$) δ (ppm): 7.17 (m, 1H), 7.47 (m, 2H), 7.60 (m, 1H), 7.83 (m, 3H), 8.84 (d, 2H), 9.03 (m, 2H). MS (ESI+) m/z: 385.0 [M+1]$^+$. HRMS (ESI+) m/z for $C_{21}H_{13}N_4S_2$; calcd 385.0582; found 385.0576.

Preparation of Os(biq)$_2$Cl$_2$. $K_2[OsCl_6]$ (1.23 g, 2.5 mmol) and 2.1 eq. of 2,2'-biquinoline (1.28 g, 5 mmol) were dissolved in ethylene glycol (15 mL) and stirred at reflux until the reaction was complete by TLC. Reduction of Os$^{3+}$ to Os$^{2+}$ was accomplished with an aqueous, saturated solution of $Na_2S_2O_4$ (3 mL) to form a precipitate that was filtered and washed with water and then diethyl ether to yield a dark green solid (1.82 g, 91%).

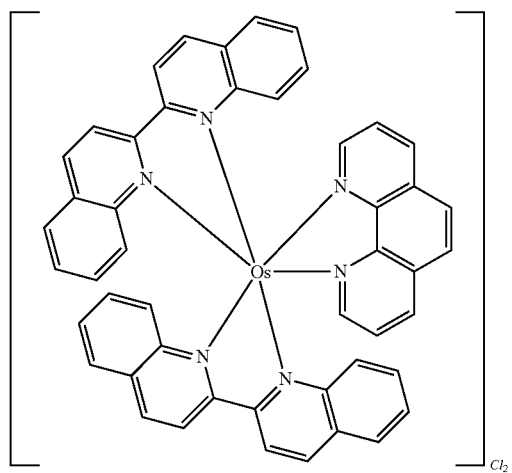

Preparation of TLDOsH2B Cl$_2$ and TLDOsH2B 2PF$_6$. Os(biq)$_2$Cl$_2$ (162 mg, 0.2 mmol) and [1,10]phenanthroline monohydrate (48 mg, 0.24 mmol) were combined in argon-purged ethylene glycol (2.5 mL) and irradiated in a single-vessel microwave reactor (180° C., 300 W) for 10 minutes. The reaction mixture was allowed to cool and partitioned between water and $CH_2Cl_2$. The aqueous phase was washed with $CH_2Cl_2$ to remove unreacted ligand, and then an aqueous solution of $NH_4PF_6$ was added dropwise until no further precipitate formed. The product was extracted into $CH_2Cl_2$ and concentrated under reduced pressure to yield a dark purple solid (247 mg). Purification of TLDOsH2B 2PF$_6$ was done on silica, eluting with a 7.5-10% $H_2O$:MeCN solution containing 0.5% $KNO_3$. The fractions containing the desired product were combined, evaporated under reduced pressure, and further dried under vacuum to give the corresponding $NO_3^-$ complex and excess $KNO_3$. To remove the unwanted salt, the product was dissolved in water with sonication. A saturated aqueous solution of $KPF_6$ was added until no further product precipitated. The desired $PF_6^-$ complex was extracted using $CH_2Cl_2$. The organic layer was separated, concentrated under reduced pressure, and dried under vacuum to give the final pure product as a dark purple solid (105 mg, 45%) which was subjected to anion metathesis to form the corresponding chloride complex (87.7 mg, 97% conversion efficiency) on Amberlite IRA-410. $^1H$ NMR (300 MHz, CD$_3$CN) δ (ppm): 9.10-8.95 (m, 2H), 8.90-8.75 (m, 4H), 8.27-8.15 (m, 4H), 8.12 (d, J=7.7 Hz, 2H), 7.98 (s, 2H), 7.86-7.74 (m, 2H), 7.68 (dq, J=7.8, 4.4, 3.3 Hz, 4H), 7.48 (d, J=4.3 Hz, 2H), 7.26 (d, J=6.4 Hz, 2H), 7.01 (d, J=5.1 Hz, 2H), 6.90 (dd, J=14.7, 6.4 Hz, 4H), 6.79 (d, J=6.6 Hz, 2H). MS (ESI+) m/z: 442.1 [M-2PF$_6$]$^{2+}$, 1027.2 [M-PF$_6$]. HRMS (ESI+) m/z for $C_{48}H_{32}N_6Os$; calcd 442.1146; found 442.1132.

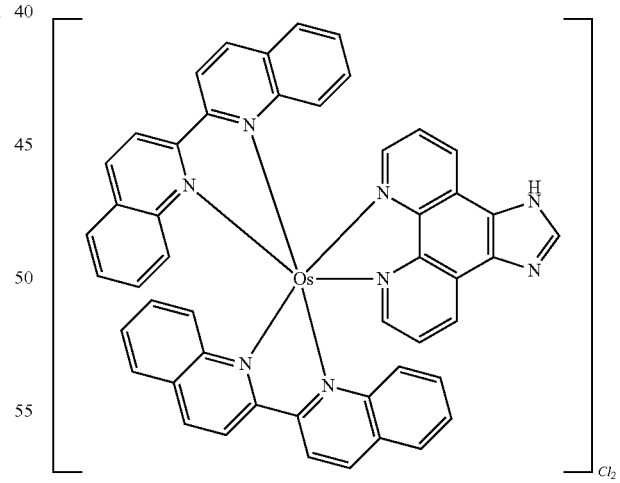

Preparation of TLDOsH2IP Cl$_2$ and TLDOsH2IP 2PF$_6$: Os(biq)$_2$Cl$_2$ (81 mg, 0.1 mmol) and Imidazo[4,5-f][1,10]phenathroline (22 mg, 0.1 mmol) were combined in argon-purged ethylene glycol (2.5 mL) and irradiated in a single-vessel microwave reactor (180° C., 300 W) for 10 minutes. The reaction mixture was allowed to cool and partitioned between water and $CH_2Cl_2$. The aqueous phase was washed with CH$_2$Cl$_2$ to remove unreacted ligand, and then an aqueous solution of saturated NH$_4$PF$_6$ was added dropwise until no further precipitate formed. The solid was extracted into CH$_2$Cl$_2$ and concentrated under reduced pressure to yield the TLDOsH2IP 2PF$_6$s a dark purple solid (120 mg, 99%) in quantitative yield. The material was used without further purification. 100 mg of the product was subjected to anion metathesis to form the corresponding chloride complex (61.4 mg, 76% conversion efficiency) on Amberlite IRA-410. $^1$H NMR (300 MHz, CD$_3$CN) δ (ppm) 9.02 (d, J=8.9 Hz, 2H), 8.83 (d, J=3.6 Hz, 2H), 8.80 (d, J=3.5 Hz, 2H), 8.22-8.13 (m, 3H), 8.10 (d, J=8.3 Hz, 2H), 7.88 (d, J=5.3 Hz, 2H), 7.84-7.75 (m, 2H), 7.63 (d, J=7.9 Hz, 2H), 7.47 (t, J=7.2 Hz, 2H), 7.22 (t, J=7.2 Hz, 2H), 7.05-6.95 (m, 2H), 6.91 (d, J=8.8 Hz, 4H), 6.80-6.71 (m, 2H). MS (ESI+) m/z: 462.1 [M-2PF$_6$]$^{2+}$, 1069.2 [M-PF$_6$]. HRMS (ESI+) m/z for C$_{49}$H$_{32}$N$_8$Os; calcd 462.1177; found 462.1174.

partitioned between water and CH$_2$Cl$_2$. The aqueous phase was washed with CH$_2$Cl$_2$ to remove unreacted ligand, and then an aqueous saturated solution of NH$_4$PF$_6$ was added dropwise until no further precipitate formed. The product was extracted into CH$_2$Cl$_2$ and concentrated under reduced pressure to yield a dark purple solid (96 mg, 74%). TLDOs1H 2PF$_6$ required no further purification. The pure product (65 mg) was subjected to anion metathesis to form the corresponding chloride complex (47.9 mg, 91% conversion efficiency) on Amberlite IRA-410. $^1$H NMR (300 MHz, CD$_3$CN) δ (ppm): 9.01 (d, J=9.0 Hz, 2H), 8.82 (d, J=9.1 Hz, 4H), 8.51 (s, 2H), 8.18 (d, J=8.6 Hz, 2H), 8.10 (d, J=8.4 Hz, 2H), 7.88 (d, J=5.3 Hz, 2H), 7.85-7.73 (m, 4H), 7.64 (d, J=7.6 Hz, 2H), 7.57 (d, J=4.9 Hz, 1H), 7.53-7.44 (m, 2H), 7.29-7.19 (m, 2H), 7.19-7.12 (m, 1H), 7.06-6.96 (m, 3H), 6.91 (d, J=9.2 Hz, 4H), 6.78 (d, J=6.7 Hz, 2H). MS (ESI+) m/z: 503.1 [M-2PF$_6$]$^{2+}$, 1005.2 [M-PF$_6$]. HRMS (ESI+) m/z for C$_{53}$H$_{34}$N$_8$OsS; calcd 503.1115; found 503.1105.

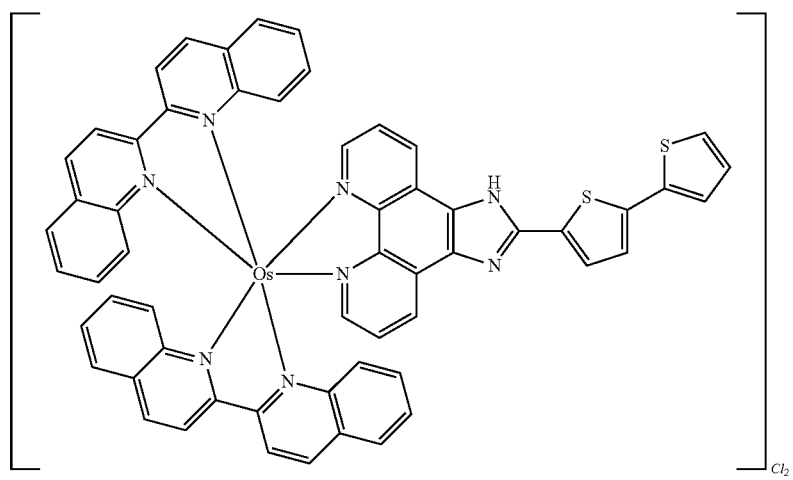

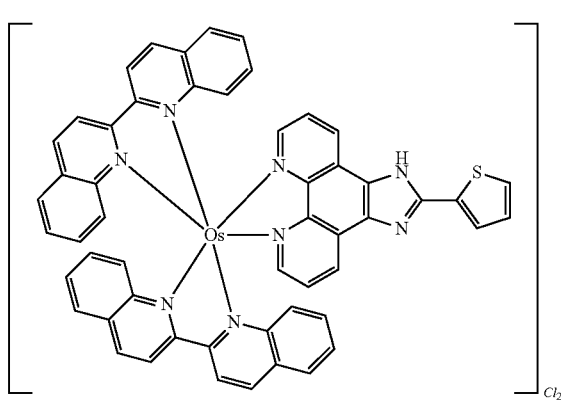

Preparation of TLDOs1H Cl$_2$ and TLDOs1H 2PF$_6$. Os(biq)$_2$Cl$_2$ (81 mg, 0.1 mmol) and 2-(Thienyl)imidazo[4,5-f][1,10]phenanthroline (30 mg, 0.1 mmol) were combined in argon-purged ethylene glycol (2.5 mL) and irradiated in a single-vessel microwave reactor (180° C., 300 W) for 10 minutes. The reaction mixture was allowed to cool and Preparation of TLDOs10H Cl$_2$ and TLDOs10H 2PF$_6$. Os(biq)$_2$Cl$_2$ (81 mg, 0.1 mmol) and 2-(2',2''-Bithiophene)imidazo[4,5-f][1,10]phenanthroline (38.4 mg, 0.1 mmol) were combined in argon-purged ethylene glycol (2.5 mL) and irradiated in a single-vessel microwave reactor (180° C., 300 W) for 10 minutes. The reaction mixture was allowed to cool and partitioned between water and CH$_2$Cl$_2$. The aqueous phase was washed with CH$_2$Cl$_2$ to remove unreacted ligand, and then an aqueous saturated solution of NH$_4$PF$_6$ was added dropwise until no further precipitate formed. The product was extracted into CH$_2$Cl$_2$ and concentrated under reduced pressure to yield a dark purple solid (135 mg, 98%). TLDOs10H 2PF$_6$ required no further purification. The pure product (70 mg) was subjected to anion metathesis to form the corresponding chloride complex (55.3 mg, 97% conversion efficiency) on Amberlite IRA-410. $^1$H NMR (300 MHz, CD$_3$CN) δ (ppm): 9.01 (d, J=9.0 Hz, 2H), 8.82 (d, J=9.1 Hz, 4H), 8.51 (s, 2H), 8.18 (d, J=8.6 Hz, 2H), 8.10 (d, J=8.4 Hz, 2H), 7.88 (d, J=5.3 Hz, 2H), 7.85-7.73 (m, 4H), 7.64 (d, J=7.6 Hz, 2H), 7.57 (d, J=4.9 Hz, 1H), 7.53-7.44 (m, 2H), 7.29-7.19 (m, 2H), 7.19-7.12 (m, 1H), 7.06-6.96 (m, 3H), 6.91 (d, J=9.2 Hz, 4H), 6.78 (d, J=6.7 Hz, 2H). MS (ESI+) m/z: 544.1 [M-2PF$_6$]$^{2+}$. HRMS (ESI+) m/z for C$_{57}$H$_{36}$N$_8$OsS$_2$; calcd 544.1054; found 544.1046.

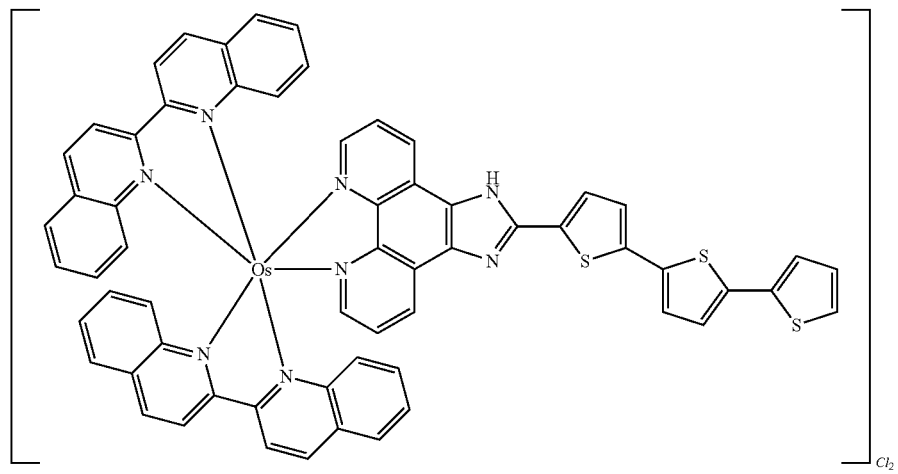

Preparation of TLDOs14H Cl$_2$ and TLDOs14H 2PF$_6$. Os(biq)$_2$Cl$_2$ (162 mg, 0.2 mmol) and 2-(2',2":5",2'''-terthiophene)-imidazo[4,5-f][1,10]phenanthroline (112 mg, 0.24 mmol) were combined in argon-purged ethylene glycol (2.5 mL) and irradiated in a single-vessel microwave reactor (180° C., 300 W) for 10 minutes. The reaction mixture was allowed to cool and partitioned between water and CH$_2$Cl$_2$. The aqueous phase was washed with CH$_2$Cl$_2$ to remove unreacted ligand, and then an aqueous solution of NH$_4$PF$_6$ was added dropwise until no further precipitate formed. The product was extracted into CH$_2$Cl$_2$ and concentrated under reduced pressure to yield a dark purple solid (456 mg). Purification of TLDOs14H PF$_6$ was done on silica, eluting with a 0-10% H$_2$O:MeCN solution containing 0.5-2.5% KNO$_3$. The fractions containing the desired product were combined, evaporated under reduced pressure, and further dried under vacuum to give the corresponding NO$_3^-$ complex and excess KNO$_3$. To remove the unwanted salt, the product was dissolved in water with sonication. A saturated aqueous solution of KPF$_6$ was added until no further product precipitated. The desired PF$_6^-$ complex was extracted using CH$_2$Cl$_2$. The organic layer was separated, concentrated under reduced pressure, and dried under vacuum to give the final pure product as a very dark brownish black solid (84 mg, 29%) which was subjected to anion metathesis to form the corresponding chloride complex (68 mg, 99% conversion efficiency) on Amberlite IRA-410. $^1$H NMR (300 MHz, CD$_3$CN-d$_3$) δ 9.01 (d, J=8.8 Hz, 2H), 8.82 (dd, J=8.7, 2.4 Hz, 4H), 8.46 (d, J=8.1 Hz, 2H), 8.19 (d, J=8.8 Hz, 2H), 8.11 (d, J=8.2 Hz, 2H), 7.88 (d, J=5.6 Hz, 2H), 7.85-7.76 (m, 2H), 7.68-7.60 (m, 3H), 7.48 (t, J=7.4 Hz, 2H), 7.36 (d, J=5.0 Hz, 1H), 7.31-7.17 (m, 5H), 7.10-7.02 (m, 1H), 7.00 (d, J=7.2 Hz, 2H), 6.93 (d, J=8.5 Hz, 4H), 6.78 (t, J=7.9 Hz, 2H). MS (ESI+) m/z: 585.1 [M-2PF$_6$]$^{2+}$. HRMS (ESI+) m/z for C$_{61}$H$_{38}$N$_8$OsS$_3$; calcd 585.0993; found 585.1012.

Formulations

The present invention also relates to compositions or formulations which comprise the compounds according to the present invention. In general, the compositions of the present invention comprise an effective amount of one or more compounds and salts thereof according to the present invention which are effective for providing photodynamic therapy; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known photodynamic compounds. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria fungi and protozoa. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more compounds according to the present invention and one or more excipients; from about 0.01 mg to about 100 mg of one or more compounds according to the present invention and one or more excipients; and from about 0.1 mg to about 10 mg of one or more compounds according to the present invention; and one or more excipients.

Procedures

The following procedures can be utilized in evaluating and selecting compounds as photodynamic compounds.

Method to determine the effect of light fluence on the PDT effect of compounds of the disclosure:

Cell line was purchased from ATCC (Mannassas, Va.): U87MG (U87, # HTB-14). The short tandem repeat (STR) profiles for all cell lines have been verified. Cells were cultured in DMEM medium supplemented with 10% fetal bovine serum and 1% penicillin (5,000 units $ml^{-1}$) and streptomycin (5,000 $\mu lml^{-1}$) (all from Gibco, Invitrogen, CA, USA) in 75 $cm^2$ flasks (Falcon, Invitrogen, CA, USA) and maintained at 37° C. in 5% $CO_2$. Cells were passaged at 80% confluence, and complete media exchange was performed every 2-3 days. Cells were used between 6 and 27 passages.

24 hours prior to experiments 15,000 cells per well were plated in duplicate 96-well plates (Falcon, Invitrogen, CA, USA) using 200 µL of cell suspension per well. The following day, the media was replaced with media plus TLDOs14H $Cl_2$ at varying concentrations. Following 4-6 hours of PS loading, the unbound PS was removed by a complete media exchange with fresh sodium pyruvate-free media, followed by PDT light irradiation.

Irradiation of the entire 96-well plate was conducted using a laser source (B & W Tek Inc., Newark, Del., US) emitting at 808+/-25 nm. A radiant exposure of 90-600 $Jcm^{-2}$ was delivered at an irradiance of 0.120-0.190 $mWcm^{-2}$. No cooling was necessary.

Figure 3:
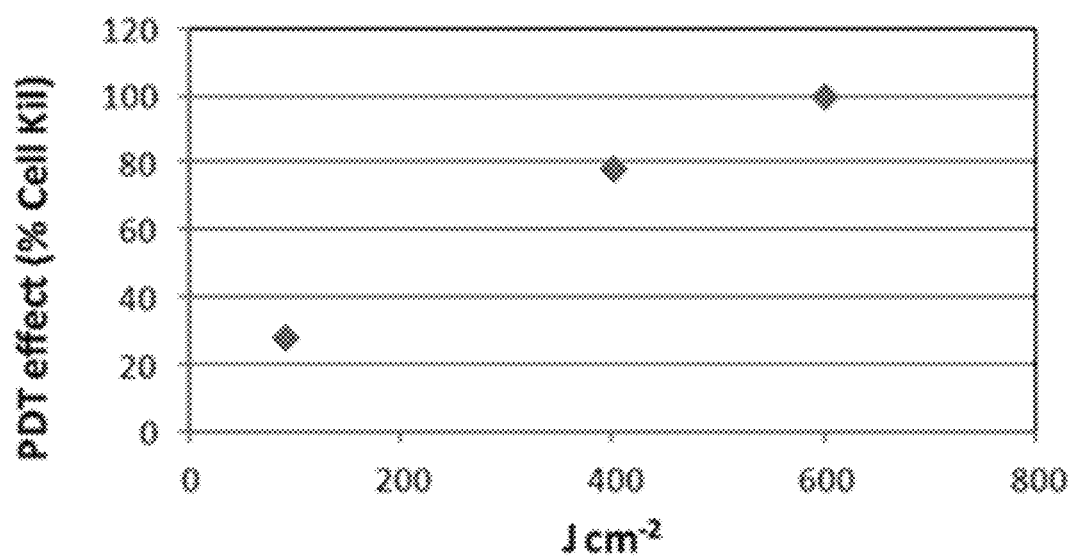
FIG. 3: Effect of light fluence on the PDT effect with 40 µM TLDOs14H $Cl_2$ (U87 cells, normoxia). The cells were irradiated with 808-nm excitation for increasing times to yield 90, 400 and 600 $J \cdot cm^{-2}$. Data are expressed as a percentage of control (no PS, no light). PDT effect was calculated by subtracting dark toxicity cell kill and light alone cell kill from the total PDT cell kill.

Cell viability was measured in the duplicate 96-wells, 24 hours post-irradiation using the Presto Blue Cell Viability assay (Invitrogen, CA, USA), according to manufacturer protocol, with the readout provided by a SpectroMax M5 (Molecular Devices, Sunnyvale, Calif., US). Exemplary results are shown in FIG. 3 which demonstrate, using TLDOs14H$Cl_2$ as a representative case, that the photodynamic effect can be increased by increasing the light dose.

Method to determine the photostability of compounds of the disclosure.

Figure 4:
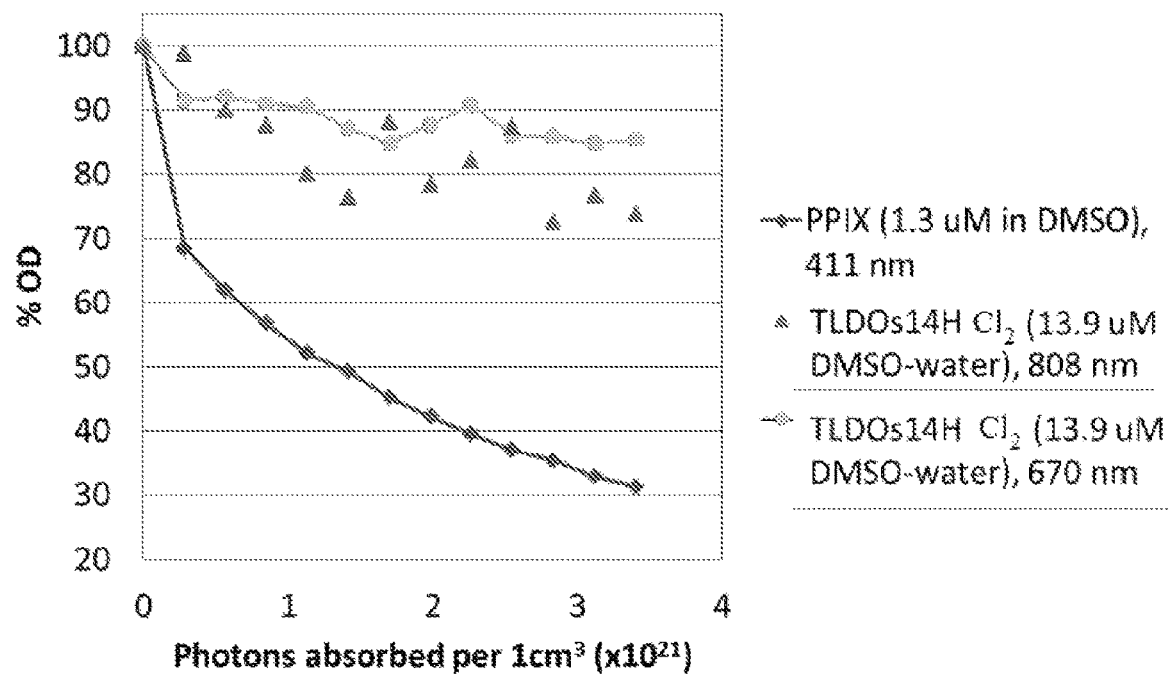
FIG. 4: Experimental evidence for high stability of new PDCs derived from metal-based coordination complexes: Photostability as quantified by photobleaching compared to the clinical PDT agent aminolevulinic acid (ALA). The ODs (normalized to time zero), of 13.9 µM TLDOs14H$Cl_2$ dissolved in DMSO-water are shown for 808 nm (triangles) and 670 nm (circles). Photobleaching of 1.3 µM PPIX (photo-dynamically active metabolite of the established photosensitizer ALA) was used as a reference (diamonds). The photobleaching was recorded for 60 minutes of irradiation (525 nm, 78 $mW \cdot cm^{-2}$).

To measure photostability, a compound of the disclosure was dissolved in distilled, deionized $H_2O$ (using concentrated stock prepared in DMSO). The PS was irradiated at 78 $mWcm^{-2}$ for a total of 60 minutes using a green LED light source (525 nm, 78 mW $cm^{-2}$). The OD at 670 nm or 808 nm was measured every 5 minutes and plotted against the absorbed photons. Exemplary results for TLDOs14H $Cl_2$ are shown in FIG. 4 and demonstrate high photostability of the compounds of the disclosure.

Method of determining the stability of the compounds of the disclosure under photobleaching conditions:

Cell line was purchased from ATCC (Mannassas, Va.): U87MG (U87, # HTB-14). The short tandem repeat (STR) profiles for all cell lines have been verified. Cells were cultured in DMEM medium supplemented with 10% fetal bovine serum and 1% penicillin (5,000 units $ml^{-1}$) and streptomycin (5,000 μl $ml^{-1}$) (all from Gibco, Invitrogen, CA, USA) in 75 $cm^2$ flasks (Falcon, Invitrogen, CA, USA) and maintained at 37° C. in 5% $CO_2$. Cells were passaged at 80% confluence, and complete media exchange was performed every 2-3 days. Cells were used between 6 and 27 passages.

24 hours prior to experiments 15,000 cells per well were plated in duplicate 96-well plates (Falcon, Invitrogen, CA, USA) using 200 μL of cell suspension per well. The following day, the media was replaced with media plus compounds of the disclosure at varying concentrations. Following 4-6 hours of PS loading, the unbound PS was removed by a complete media exchange with fresh sodium pyruvate-free media, followed by PDT light irradiation.

Irradiation of the entire 96-well plate was conducted using a laser source (B & W Tek Inc., Newark, Del., US) emitting at 808+/−25 nm. A radiant exposure of 400-600 $Jcm^{-2}$ was delivered at an irradiance of 0.120-0.190 $mWcm^{-2}$. No cooling was necessary.

Figure 5:
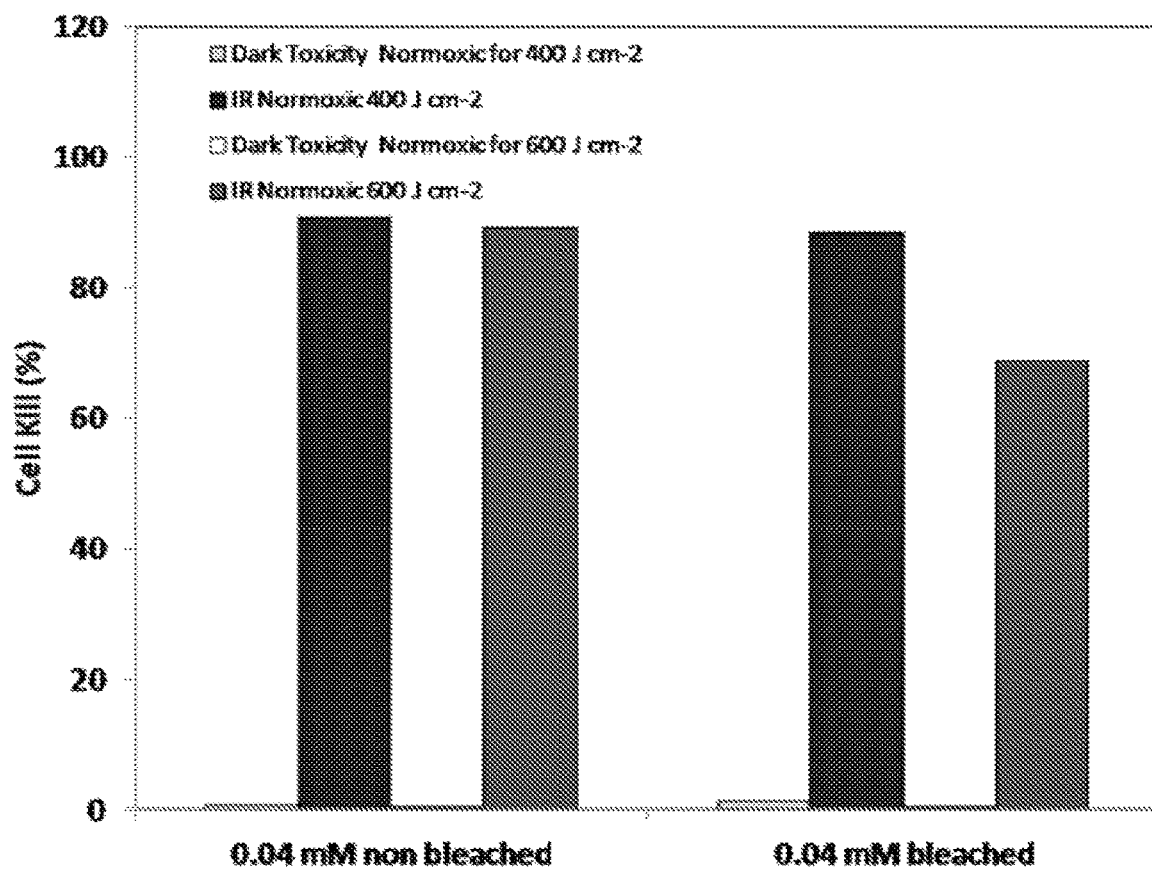
FIG. 5: Experimental evidence for high stability of TLDOs14H $Cl_2$: effective PDT before and after photobleaching illustrated for 40 µM TLDOs14H $Cl_2$ at two different light doses (U87 cells, normoxia). The "IR Normoxic" trials refer to TLDOs14H $Cl_2$-treated cells that were irradiated with 808-nm light at 400 or 600 $J \cdot cm^{-2}$ using previously bleached (300 $J \cdot cm^{-2}$ 808 nm irradiation) or non-bleached photosensitizer. Data are expressed as a percentage of cell kill normalized to control (no PS, no light irradiation). PDT effect (dark bars) was calculated by subtracting dark toxicity cell kill and light alone cell kill from the total PDT cell kill. "Dark Toxicity" trials show almost no cell kill and are barely visible in the plot.

Cell viability was measured in the duplicate 96-wells, 24 hours post-irradiation using the Presto Blue Cell Viability assay (Invitrogen, CA, USA), according to manufacturer protocol, with the readout provided by a SpectroMax MS (Molecular Devices, Sunnyvale, Calif., US). Exemplary results for TLDOs14H $Cl_2$ are shown in FIG. 5 and demonstrate that compounds of the disclosure are stable to photobleaching conditions.

Method for determining the in vitro effect of compounds of the disclosure under normoxic and hypoxic conditions.

Cell line was purchased from ATCC (Mannassas, Va.): U87MG (U87, # HTB-14). The short tandem repeat (STR) profiles for all cell lines have been verified. Cells were cultured in DMEM medium supplemented with 10% fetal bovine serum and 1% penicillin (5,000 units $ml^{-1}$) and streptomycin (5,000 μl $ml^{-1}$) (all from Gibco, Invitrogen, CA, USA) in 75 $cm^2$ flasks (Falcon, Invitrogen, CA, USA) and maintained at 37° C. in 5% $CO_2$. Cells were passaged at 80% confluence, and complete media exchange was performed every 2-3 days. Cells were used between 6 and 27 passages.

24 hours prior to experiments 15,000 cells per well were plated in duplicate 96-well plates (Falcon, Invitrogen, CA, USA) using 200 μL of cell suspension per well. The following day, the media was replaced with media plus compounds of the disclosure at varying concentrations. Following 4-6 hours of PS loading, the unbound PS was removed by a complete media exchange with fresh sodium pyruvate-free media, followed by PDT light irradiation.

Irradiation of the entire 96-well plate was conducted using a red LED array light source emitting at 635+/−25 nm provided by Theralase Inc. (Toronto, ON, Canada). A radiant exposure of 90 $Jcm^{-2}$ was delivered at an irradiance of 125 $mW cm^{-2}$. Irradiance was homogenous to within 12% across all wells. Active air cooling maintained the temperature of tissue culture medium raise below 3° C. from ambient temperature.

For hypoxic experiments, all solutions used were kept under hypoxic conditions for at least 24 hours prior to the experiment. To facilitate attachment, the cell containing 96 well plates were transferred to a hypoxic chamber (InvivO$_2$ 400 Ruskinn Technology Ltd., UK) 4 hours post normoxic seeding. The plates remained in hypoxic conditions for 24 hours prior to PDT light irradiation. The hypoxic chamber had an atmosphere of 0.5% $O_2$, 5% $CO_2$, balance with $N_2$, at 37° C. and 95% humidity. As under normoxic conditions, media with PS was added and then replaced with fresh media following the 4-6 hour photosensitizer loading. Cells were kept for 2 hours at 0.1% $O_2$ to further reduce the available oxygen in the experimental well. The oxygen diffusion times across the ~3 mm liquid column is much shorter than the exposure times of ~7 min and hence re-oxygenation from the outside environment needed to be limited without compromising PDT independent cell survival. Following irradiation, cells were kept at 0.5% $O_2$ for 24 hours until cell viability measurements were performed. For all procedures conducted under normal, ambient conditions (light irradiation, cell kill measurements), the plates containing hypoxic cells were sealed airtight with an oxygen-impermeable adhesive film (Evergreen Scientific, USA). When the plates were returned to hypoxic conditions, sealing was removed and the plate covers were replaced. This did not alter the $pO_2$ in the experimental wells, as tested with a colormetric assay (Suflita, J. and Concannon, F., 1995).

Cell viability was measured in the duplicate 96-wells, 24 hours post-irradiation using the Presto Blue Cell Viability assay (Invitrogen, CA, USA), according to manufacturer protocol, with the readout provided by a SpectroMax M5 (Molecular Devices, Sunnyvale, Calif., US). Examplary results are shown in FIG. 6 which demonstrates that these compounds are able to kill cells with light activation at concentrations where dark toxicity is negligible. It also demonstrates that some of these compounds exhibit a photodynamic effect even in hypoxia, which signals Type 1 photoactivity in some representative examples.

Method for the production of reactive oxygen species by compounds of the disclosure:

Cell line was purchased from ATCC (Mannassas, Va.): U87MG (U87, # HTB-14). The short tandem repeat (STR) profiles for all cell lines have been verified. Cells were cultured in DMEM medium supplemented with 10% fetal bovine serum and 1% penicillin (5,000 units $ml^{-1}$) and streptomycin (5,000 μl$ml^{-1}$) (all from Gibco, Invitrogen, CA, USA) in 75 $cm^2$ flasks (Falcon, Invitrogen, CA, USA) and maintained at 37° C. in 5% $CO_2$. Cells were passaged at 80% confluence, and complete media exchange was performed every 2-3 days. Cells were used between 6 and 27 passages.

24 hours prior to experiments 15,000 cells per well were plated in duplicate 96-well plates (Falcon, Invitrogen, CA, USA) using 200 μL of cell suspension per well. The following day, the media was replaced with media plus TLDOs14H $Cl_2$ at varying concentrations. Following 4-6 hours of PS loading, the unbound PS was removed by a complete media exchange with fresh sodium pyruvate-free media, followed by PDT light irradiation.

Irradiation of the entire 96-well plate was conducted using a red LED array light source emitting at 635+/−25 nm provided by Theralase Inc. (Toronto, ON, Canada). A radiant exposure of 90 Jcm$^{-2}$ was delivered at an irradiance of 125 mWcm$^{-2}$. Irradiance was homogenous to within 12% across all wells. Active air cooling maintained the temperature of tissue culture medium raise below 3° C. from ambient temperature.

To reveal contribution of hydroxyl radical and singlet oxygen into PDT effect, the cells were loaded with PS in the presence of either N,N'-dimethylthiourea (DMTU) (40 mM), a scavenger of hydroxyl radicals or sodium azide (2 mM), a scavenger of singlet oxygen. Before PDT, after removal of PS, freshly prepared solutions of the scavengers were added to the cells; they were removed and replaced with fresh medium after PDT.

Figure 7:
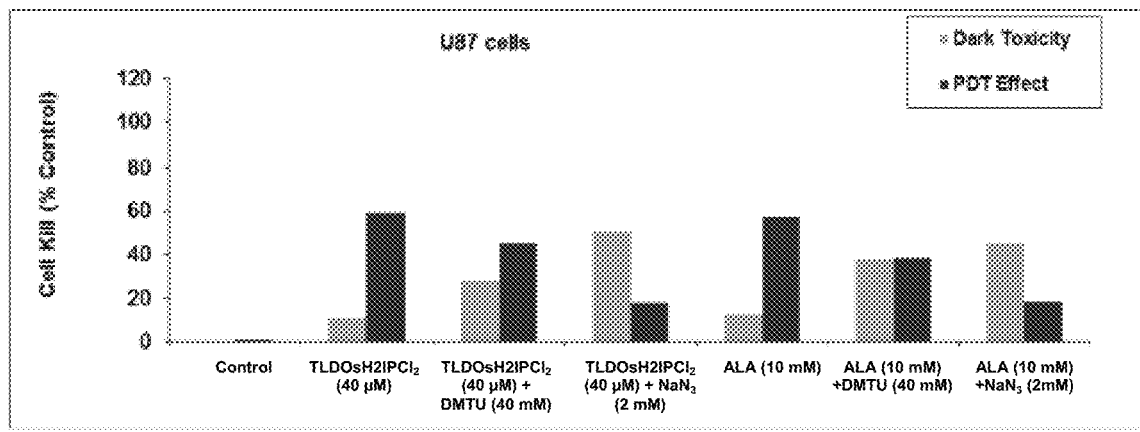
FIG. 7: Experimental evidence for the production of ROS by TLDOsh2IP $Cl_2$ in vitro: diminished cell kill in U87 line in the presence of $NaN_3$ (singlet oxygen scavenger) and DMTU (hydroxyl radical scavenger). Efficacies of TLDOsh2IP $Cl_2$ (40 µM) and ALA (10 mM) toward U87 cell kill without light (gray bars) and with light (black bars) in the presence of scavengers of hydroxyl radical (DMTU, 40 mM) and of singlet oxygen ($NaN_3$, 2 mM) following irradiation at 635 nm, 90 $J \cdot cm^{-2}$. Effects are expressed as a percentage of control (no PS, no light) by subtracting dark toxicity cell kill and light alone cell kill from the total PDT cell kill.
Figures 12, 13:
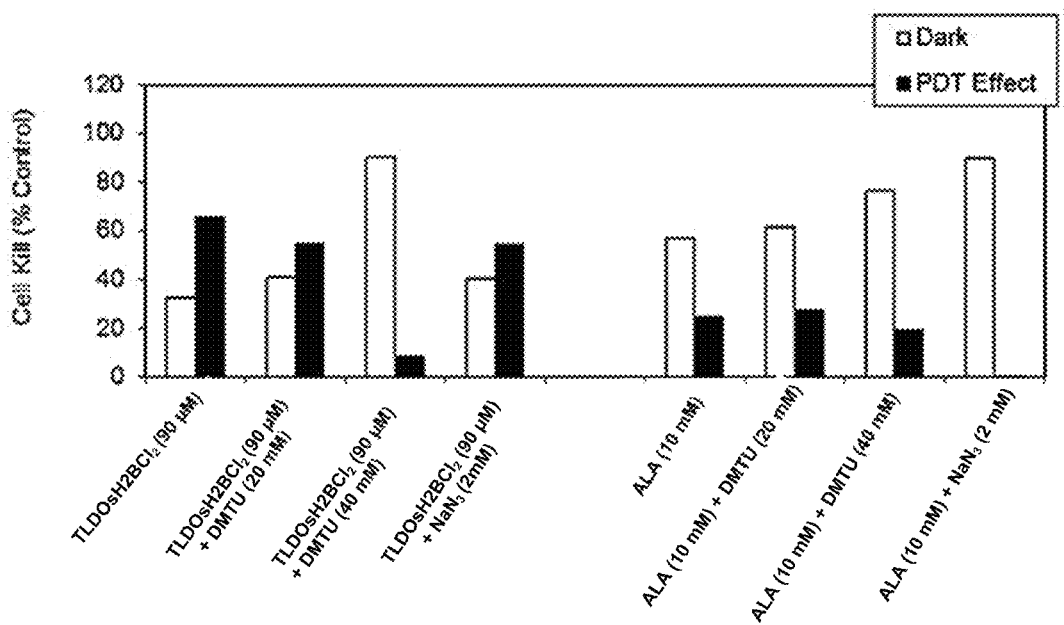
FIG. 12: Experimental evidence for oxygen-independent PDT effect by TLDOsH2B $Cl_2$ in vitro: unaffected cell kill in U87 line in the presence of $NaN_3$ (singlet oxygen scavenger) and strongly diminished cell kill in the presence of DMTU (hydroxyl radical scavenger). Efficacies of TLDOsh2B $Cl_2$ (90 µM) and ALA (10 mM) toward U87 cell kill without light (gray bars) and with light (black bars) in the presence of scavengers of hydroxyl radical (DMTU, 20-40 mM) and of singlet oxygen ($NaN_3$, 2 mM), following irradiation at 635 nm, 90 $J \cdot cm^{-2}$. Effects are expressed as a percentage of control (no PS, no light) by subtracting dark toxicity cell kill and light alone cell kill from the total PDT cell kill.
FIG. 13: Formula for determining DNA binding constants for compounds of the disclosure.

Cell viability was measured in the duplicate 96-wells, 24 hours post-irradiation using the Presto Blue Cell Viability assay (Invitrogen, CA, USA), according to manufacturer protocol, with the readout provided by a SpectroMax M5 (Molecular Devices, Sunnyvale, Calif., US). Exemplary results are shown in FIGS. 7 and 12 which demonstrates that TLDOsh2IP Cl$_2$ and TLDOsh2B Cl$_2$ produce reactive oxygen species.

When TLDOsH2B-mediated PDT is carried out in the presence of scavengers for hydroxyl radical, the PDT affect is almost eliminated, suggesting that this compound demonstrates Type I photoactivity in these cancer cells. This assignment is further supported by the observation that a scavenger of singlet oxygen (a Type 2 intermediate) does not diminish the PDT effect to any significant extent. Therefore, hydroxyl radicals could play a key role in a number of biological phenomena attributed to this class of agents, including: photobinding to DNA and other biomolecules, nuclease activity, DNA photocleavage, and cytotoxic photoredox pathways.

Quantification of in vitro PDT toward human cancer cells by compounds of this invention.

HL-60 human promyelocytic leukemia cells (ATCC CCL-240) growing in log phase were transferred in aliquots of 50 µL (approximately 40,000 cells) to two 96-well tissue-culture microplate (Corning Costar, Acton, Mass.) containing 25 µL warm culture medium (RPMI-1640 media supplemented with 20% FBS), and placed in a 37° C., 5% $CO_2$ water-jacketed incubator (Thermo Electron Corp., Forma Series II, Model 3110, HEPA Class 100) for one hour to equilibrate. Warm 25 µL aliquots of serially diluted compounds of the disclosure, freshly made in PBS (2.68 mM potassium chloride, 1.47 mM potassium phosphate monobasic, 0.137 M sodium chloride, and 8.10 mM sodium phosphate dibasic, pH 7.4), were added to the cells and incubated at 37° C. under 5% $CO_2$ for 15-19 hr. One of the microplates was irradiated with visible light (400-700 nm) using a 190 W projector (BenQ MS510) for 1 hr (0.0278 mW·cm$^{-2}$s$^{-1}$, total light dose was 100 J·cm$^2$), while the other microplate was kept in the dark. Both microplates were then incubated (37° C. under 5% $CO_2$) for approximately 48 hr. Cell proliferation and viability was determined by using the alamar blue reagent redox indicator which is based on the ability of metabolically active cells to convert the reagent into a fluorescent indicator. Briefly, warm 10 µL aliquots of warm alamar blue reagent (Life Technologies DAL 1025) was added to all sample wells and the microplates were incubated for 15-16 hr at 37° C. under 5% $CO_2$. The microplates were then placed in a Cytofluor 4000 fluorescence microplate reader with the excitation filter set at 530±25 nm and emission filter set at 620±40 nm. The data was subsequently imported into a Microsoft excel spreadsheet (Microsoft Office 2010) and used for data analysis.

Figure 14:
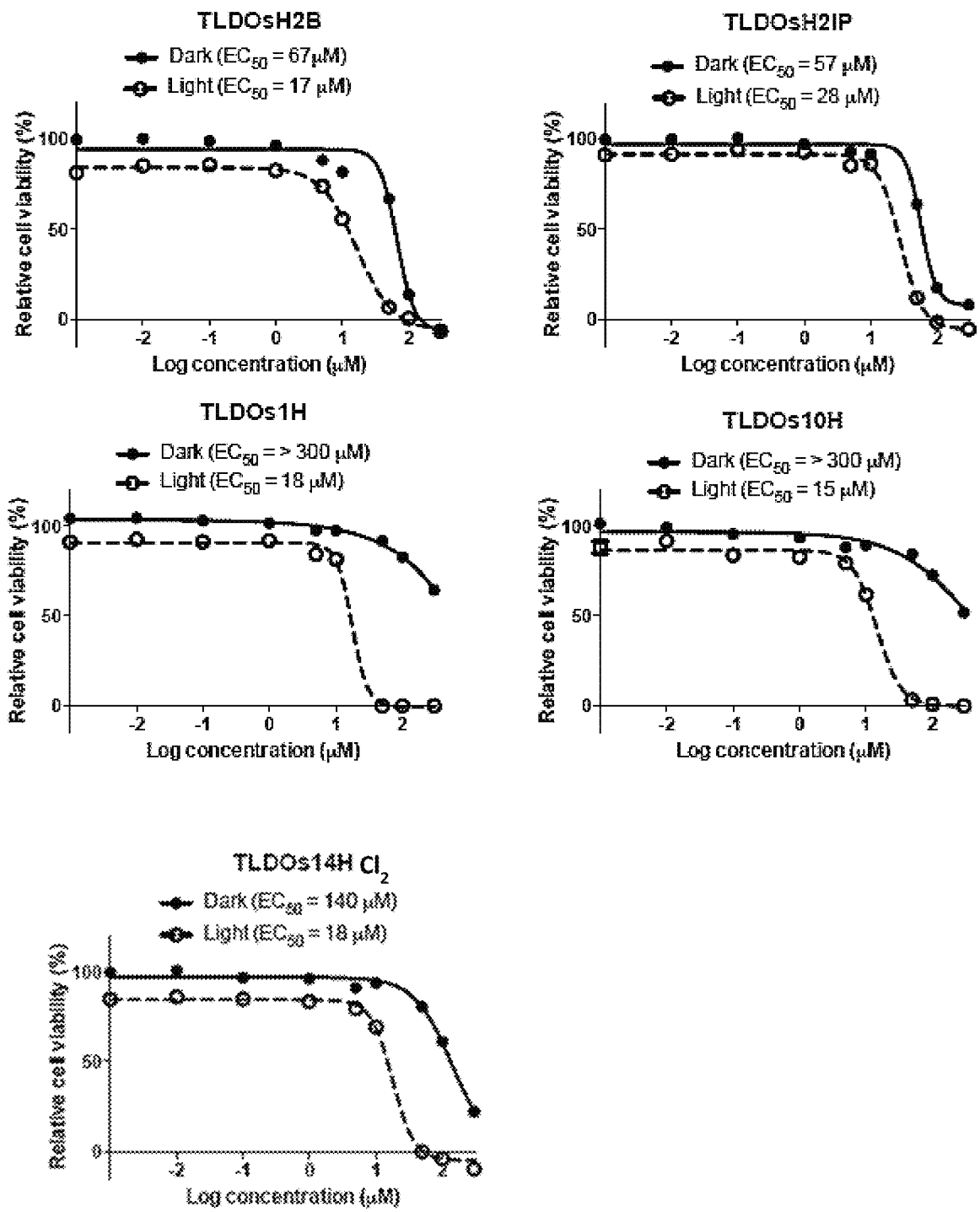
FIG. 14: Concentration dependent effect on the in vitro PDT effect of compounds of the disclosure (TLDOsH2B $Cl_2$, TLDOsH2IP $Cl_2$, TLDOs1H $Cl_2$, TLDOs10H $Cl_2$, TLDOs14H $Cl_2$) on HL-60 cells without light (broken lines) and with light (solid lines). Relative cell viability was assessed by the Alamar Blue assay according to the manufacturer's instructions. Effects are expressed as a percentage relative to untreated controls. Light dose: white light (400-700 nm), 100 $J \cdot cm^{-2}$.

Exemplary results are shown in FIG. 14 which demonstrate that broad-spectrum white light, in addition to light of a narrow wavelength range, can be used to destroy mammalian cancer cells via the photodynamic effect, and this activity translates to the elimination of microbial cells such as bacteria, fungi, protozoa, and viruses.

Photodynamic inactivation (PDI) of methicillin-resistant *S. aureus* (MRSA) mediated by photosensitizers TLDOsH2IP Cl$_2$ and TLDOsH2B Cl$_2$ Cultures were grown overnight in Columbia broth. Bacterial reference aliquots were prepared by dilution of the overnight culture with fresh media to an $OD_{\lambda=600nm}$ of 0.3, which is equivalent to 108 cfu mL$^{-1}$. PS stock solutions of 2 mM were prepared in high-purity water (MilliQ, 18.5 mΩ), and serial dilutions were prepared in low light conditions to achieve final concentrations ranging from 409.6 to 0.4 µM. Bacterial aliquots were added to a 96 well plate (60 µL per well) followed by addition of 60 µL of media containing the appropriate PS dilution, including controls for each SA strain without PS. Plates were prepared in duplicate, whereby one plate served as a dark control and was incubated for 30 minutes with the PS in the dark at 37° C. The other plate identical plate was exposed to red light (72 J cm$^{-2}$ total radiance) for 10 minutes. Bacterial quantification was carried out by manual counting; 30 µL aliquots diluted in PBS were plated on Columbia agar plates, and colonies were counted after 24-hour incubation at 37° C. Exemplary results are shown in FIG. 15 which demonstrate that compounds of this disclosure are capable of destroying infectious agents, particularly bacteria and antibiotic-resistant bacteria.

Figure 17:
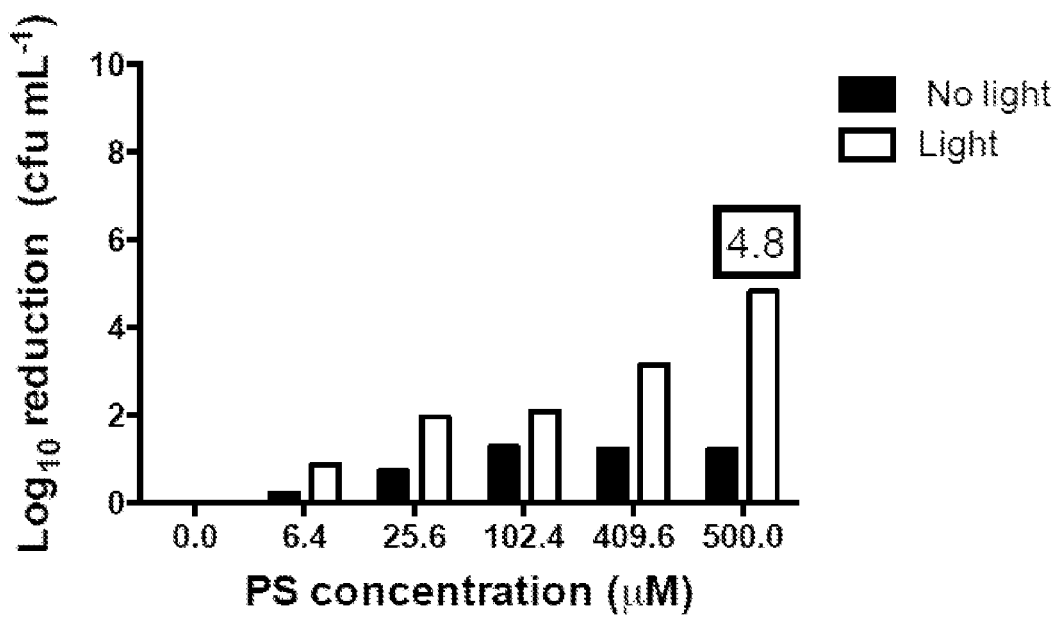
FIG. 17: Experiment performed with Klebsiella pneumoniae (Kp) with photosensitizers (PS) TLDOsH2IP $Cl_2$ and TLDOsH2B $Cl_2$. Maximum log of kill achieved: Kp (2IP, 530 nm): 4.8, Kp (H2B, 530 nm): 8.
Figure 17:
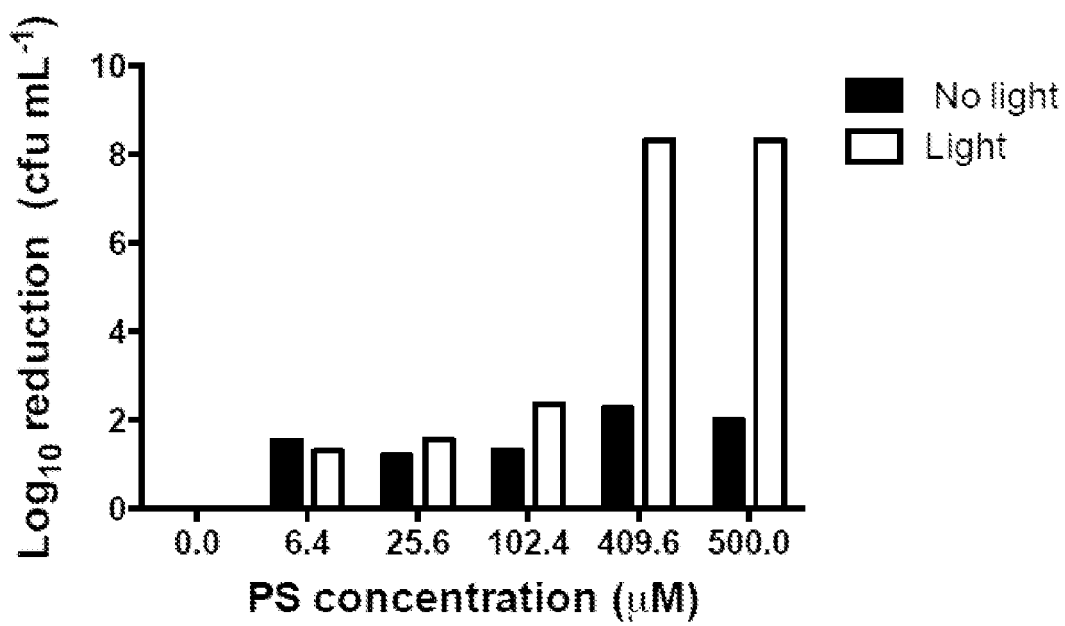

Photodynamic inactivation of *Klebsiella pneumoniae* (Kp) by compounds of the disclosure:

Cultures were grown overnight in Columbia broth. Bacterial reference aliquots were prepared by a dilution of the overnight culture in fresh media with an $OD_\lambda$=600 nm of 0.3, which is equivalent to $10^8$ cfu mL$^{-1}$. PS stock solutions of 2 mM were prepared in purified water (MilliQ, 18.5 mΩ), and serial dilutions were prepared in low light conditions to achieve final concentrations ranging from 500 to 6.4 µM. Bacterial aliquots were added to a 96 well plate (40 µl per well) followed by 40 µl of media with the appropriate PS dilution, including controls. Plates were prepared in duplicate, whereby one plate served as a dark control and was incubated for 30 minutes with the PS in the dark at 37° C. The other plate with identical bacteria and PS concentrations was exposed to light for 10 minutes using a green (530 nm) light source (66 Jcm$^{-2}$ total radiance). Bacterial quantification was carried out using manual counting, 10 µL aliquots diluted in PBS were plated on Columbia agar plates, and colonies were counted after 24-hour incubation at 37° C. Exemplary results are shown in FIG. 17 which demonstrates that compounds of the disclosure are capable of eliminating *Klebsiella pneumonia.*

Figure 8:
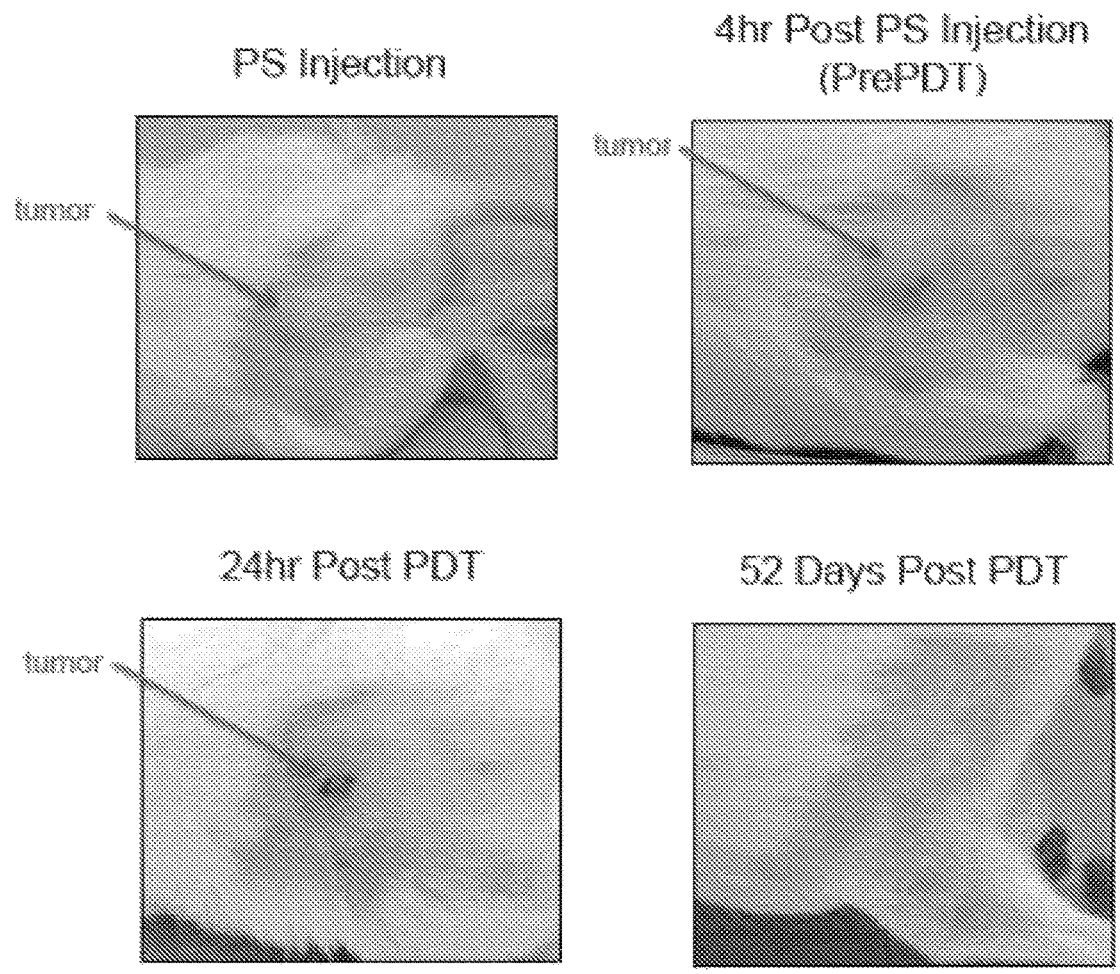
FIG. 8: Subcutaneous CT26.WT colorectal tumors treated with PDT (TLDOs2IP $Cl_2$, 808 nm, 600 $J \cdot cm^{-2}$) in a BALB/c Mouse. Tumor Size: 5.0 0.5 mm; dose: 3 mg $kg^{-1}$; volume: 100 µL; and time: 10 µL/min. At 52 days post-PDT treatment, mice were tumor-free and healthy.
Figure 9:
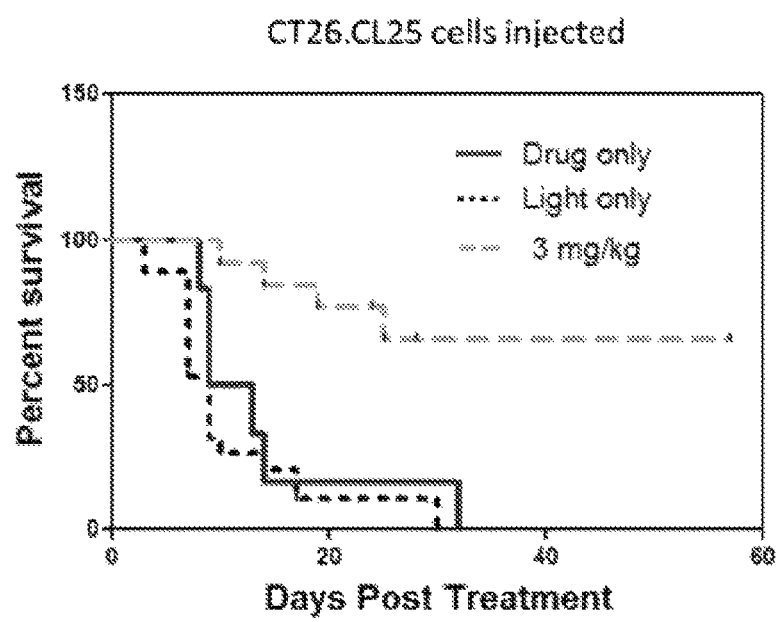
FIG. 9: Experimental evidence for an increase in animal survival using PDT anti-cancer treatment: surviving animals treated with PS+light are still under observation. TLDOsH2IP concentration, 3 $mg \cdot kg^{-1}$; light dose (808 nm, 600 $J \cdot cm^{-2}$).
Figure 10:
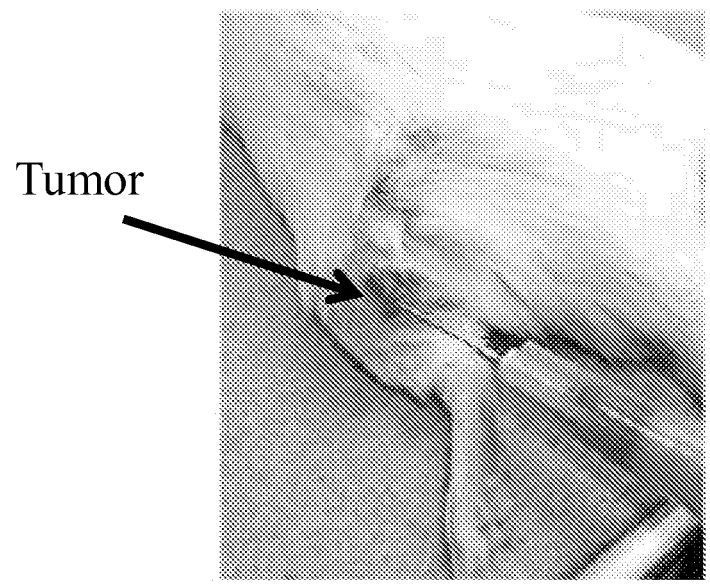
FIG. 10: Tumor retention of a deeply pigmented compound of the disclosure that can be used as a colorimetric indicator to signal the presence of tumor cells in an animal model.

In Vivo Mouse Models:

All animal experiments were carried out in accordance with protocols approved by the Animal Care Committee at the University Health Network, ON, Canada (IACUC approval date Aug. 3, 2012 assurance number A5408-01). All animals were housed in the vivarium with water and food supplied ad libitum in a 12 hour day/night cycle. Cell line was purchased from ATCC (Mannassas, Va.); CT26 wild type (CT26.WT, # CRL-2638). The short tandem repeat (STR) profiles for all cell lines have been verified. Cells were cultured in RPMI 1640 medium supplemented with 10% fetal bovine serum and 1% penicillin (5,000 units ml$^{-1}$) and streptomycin (5,000 µlml$^{-1}$) (all from Gibco, Invitrogen, CA, USA) in 75 cm² flasks (Falcon, Invitrogen, CA, USA) and maintained at 37° C. in 5% $CO_2$. Cells were passaged at 80% confluence, and complete media exchange was performed every 2-3 days. Cells were used between 6 and 27 passages. For CT26.WT murine colon carcinoma cell injections, 8-10 week old BALB/c mice were anaesthetized with isofluorane (5% induction, 1.5% maintenance) and one hind leg was shaved. Mice were subcutaneously injected with 3 to 3.5×10⁶ cells per mouse in 100 μl PBS into the dorsal area of the leg over 30 seconds. The tumor size was measured in two dimensions with a manual Vernier calliper every 2-3 days. When tumor size reached 5-6 mm, 3 mg/kg compounds of the disclosure were intratumoral (IT) injected by an estimate of 100 μL at a body weight of 20 g. Control mice were IT injected with sterile saline. After 4 hours the tumors were irradiated while mice were under anesthesia with isofluorane. Exemplary results are shown in FIGS. 8, 9 and 10 which demonstrate that compounds of this invention are capable of eradicating tumors in mice when activated by UV-IR light.

Compounds of this disclosure are capable of prolonging survival in PDT-treated mice with cancer.

All animal experiments were carried out in accordance with protocols approved by the Animal Care Committee at the University Health Network, ON, Canada (IACUC approval date Aug. 3, 2012 assurance number A5408-01). All animals were housed in the vivarium with water and food supplied ad libitum in a 12 hour day/night cycle. For CT26.CL25 immunogenic type murine colon carcinoma cell injections, 8-10 week old BALB/c mice were anaesthetized with isofluorane (5% induction, 1.5% maintenance) and one hind leg was shaved. Mice were subcutaneously injected with 2.5×10⁶ cells per mouse in 100 μl PBS into the dorsal area of the leg over 30 seconds. The tumor size was measured in two dimensions with a manual Vernier calliper every 2-3 days. When tumor size reached 5-6 mm Os2IP was intratumoral (IT) injected by an estimate of 100 μL at a body weight of 20 g. Control mice were IT injected with sterile saline. After 4 hours the tumors were irradiated while mice were under anesthesia with isofluorane, delivered in sterile saline. After 4 hours the tumors were irradiated with red light (635 nm) while mice were under anesthesia with isofluorane. Exemplary results for compounds of the disclosure are shown in FIG. 16 which demonstrates increased survival time under the conditions of the experiment.

PDT-treatment in mice prevents tumor regrowth with CT26.CL25 (antigenic) cells.

On day 0, mice with a 6-mm subcutaneous tumor are treated by PDT with TLDOsH2IP Cl2; on day 1, no tumor is reported upon clinical evaluation and caliper measurement. On day 20, the same tumor-free animal is rechallenged with CT26.CL25 (antigenic) cells that express a tumor antigen. On day 21 and thereafter (>4 days), observation reveals that PDT-treated mice are cured and resistant to rechallenge. The PDT anti-tumor effects are completely abrogated in the untreated animals, and tumor growth is reported on day 4 in all mice.

Extraction of Topoisomerase II from HL60 Cells

Nuclear extracts were affinity precipitated as described in 'Small Scale Preparation of Topo I and II Extracts from Tissue Culture Cells (Optimized for HeLa Cells)' on the TopoGEN website (http:www.topogen.com/html/extracts.html). All steps were conducted on ice or at 4° C. Briefly, 10 mL of exponentially growing HL-60 cells (1×10⁶ cells/mL) were transferred to a sterile 15 mL conical centrifuge tube (Fisher Scientific, Canada) and pelleted in an eppendorf 5804R centrifuge (16.1 cm radius) at 2100 rpm for 3 min at 4° C. The cells were washed twice with 3 mL of ice cold phosphate buffered saline (PBS) containing 2.68 mM potassium chloride, 1.47 mM potassium phosphate monobasic, 0.137 M sodium chloride, and 8.10 mM sodium phosphate dibasic, pH 7.4, as follows: the cell pellet was resuspended with PBS buffer (mixed by pipetting up and down), centrifuged at 2100 rpm (3 min, 4° C.), and the supernatant gently poured off. After the second wash, the cells were resuspended in 3 mL of cold hypotonic buffer (10 mM Tris-HCl, pH 7.5, 1 mM EDTA, 4 mM $MgCl_2$, 0.5 mM phenylmethylsulfonyl fluoride (PMSF)), and clumps were dispersed by pipetting up and down. The cells were pelleted again (2100 rpm, 3 min, 4° C.), resuspended and dispersed in 3 mL of the same cold hypotonic buffer, and left on ice for 10 min to swell. Cell membranes were disrupted with a cold Dounce homogenizer (Pyrex, 15 mL), using 6-8 strokes. The lysate was transferred to a clean sterile 1.5 mL microcentrifuge tube (Fisher Scientific, Canada) and centrifuged (2900 rpm, 10 min, 4° C.). The pellet, containing nuclei, was washed twice with the same cold hypotonic buffer, as follows: cold buffer was added to the pellet and the nuclei was resuspended by pipetting up and down, then pelleted (2900 rpm, 10 min, 4° C.), the supernatant gently removed and discarded. After the second wash, the nuclei were resuspended in 4 pellet volumes (approximately 500 μL) of cold hypotonic buffer without $MgCl_2$. An equal volume of cold 1 M NaCl was added to the resuspended pellet and left on ice for 45 min, followed by pelleting in a microcentrifuge (14,000 rpm, 15 min, 4° C.). The supernatant (nuclear extract), suspended in 5 mM Tris-HCl (pH 7.5), 0.5 mM EDTA, 0.25 mM PMSF, and 0.5 M NaCl, was used for DNA relaxation assays.

Total protein concentration (BSA equivalent) of the extract was determined by using a Micro Lowry total protein kit (Total Protein Kit, Micro Lowry, Peterson's modification), following the manufacturer's instruction for 'Protein Determination without Protein Precipitation.' Briefly, five BSA protein standards were prepared from a 400 μg/mL stock solution in pure water to a volume of 200 μL in 1.5 mL sterile microcentrifuge tubes (final concentrations of BSA were 10, 20, 40, 60, 80 μg). A sixth tube containing pure water only was used as a blank. A seventh tube, containing 50 μL nuclear extract and 150 μL (dilution chosen randomly) was prepared in order to measure its protein content against the BSA standards. All tubes were mixed well with vortexing, then 200 μL Lowry reagent solution was added to all tubes followed by vortexing to mix. The solutions sat at room temperature for 20 min, then 100 μL Folin Ciocalteu phenol reagent (6× dilution of 2 N stock solution) was added to each tube, followed by vortexing to mix. The colour was allowed to develop for 30 min. The solutions were transferred one at a time to a quartz cuvette, with a pathlength of 1 cm, and the absorbance of the standards and sample tubes versus the blank were measured at a wavelength of 750 nm. A plot was constructed (Excel, 2007) of the absorbance values of the standards versus their corresponding protein concentrations and linear regression was used to calculate the protein concentration in the nuclear extract sample, taking into account the 10× dilution. The result was a protein concentration of 559 μg/mL or 279 μg (BSA equivalents) of the nuclear extract.

Topoisomerase Extract Activity in DNA Relaxation Assays:

Relaxation activity of the nuclear extract, containing topo I and II, was determined by detecting the conversion of supercoiled plasmid DNA to its relaxed form in the presence of ATP. Reaction tubes (20 μL volumes) were assembled on ice by the ordered addition of: (i) pure water (variable, made up to 20 μL volume); (ii) 4 μL relaxation buffer (250 mM Tris-HC, pH 8, 0.75 M NaCl, 50 mM $MgCl_2$, 2.5 mM dithiothreitol, 150 μg BSA/mL, and 10 mM ATP); (iii) pUC19 supercoiled plasmid DNA (250 ng, or 38.6 μM bases); and (iv) topo extract (1, 2, 3, or 4 μL). The reaction was initiated by heating the tubes in a 37° C. incubator for 30 min. The reaction was stopped by adding 2 μL of 10% SDS (in sterile water), and the DNA-bound protein was then digested by adding 2 μL proteinase K (0.50 mg/mL stock in 10 mM Tris-HCl, 1 mM EDTA, pH 7.5) and incubating at 37° C. for 15 min. Then, 2 μL loading dye with ficoll (0.25% bromophenol blue, 15% ficoll, in 1×TBE buffer) was added and DNA samples were then analyzed by 1.5% agarose gel electrophoresis using 1×TBE buffer (50 V, 180 min). The gels were stained with ethidium bromide (1 μg/mL) for 30 min with subsequent destaining for 30 min in water, and visualized with UV-transillumination (UVP transilluminator) using the Gel-Doc-It Imaging system (UVP). One unit of DNA topoisomerase II activity was defined as the amount of enzyme capable of relaxing 250 ng of supercoiled DNA in 30 minutes at 37° C. (in this case, one unit=2 μL extract). The presence of topo I was assessed by testing for relaxation of pUC19 plasmid (250 ng) in the absence of ATP for 30 min at 37° C. Under these conditions, relaxation of pUC19 plasmid was not detected (indicating little to no topo I).

Topoisomerase II Assays:

Inhibition of topoisomerase II activity by compounds of the disclosure was measured by a supercoiled DNA relaxation assay using a topoisomerase II drug screening kit (TopoGEN). Briefly, 0.23 μg supercoiled pUC19 plasmid DNA (3.5 μL of 64.5 ng/μL stock solution in 10 mM Tris-C, pH 8.5) was suspended in pH 8.0 reaction buffer (250 mM Tris-HCl, 0.75 M NaCl, 50 mM $MgCl_2$, 2.5 mM dithiothreitol, 150 μg BSA/mL, and 10 mM ATP). Pure water was added (variable, made up to 20 μL volume), then 2 μL aliquots of ruthenium compounds (1, 10, 50, 100, 500, 1000 μM serial dilutions) were added, making final sample concentrations of 0.1, 1, 5, 10, 50, and 100 μM. Control samples were prepared as follows: (i) plasmid only (no nuclear extract); (ii) plasmid with nuclear extract; (iii) plasmid with the highest ruthenium concentration (no nuclear extract); and (iv) plasmid with nuclear extract (no ATP in the buffer). The tubes were mixed well (gently shaken and spun down) prior to initiating the reaction by the addition of 2 μL (one unit) nuclear extract. After 30 min incubation at 37° C., the reaction was stopped by adding 2 μL of 10% SDS (in sterile water). The DNA-bound protein was digested by adding 2 μL of proteinase K (0.50 mg/mL stock in 10 mM Tris-HCl, 1 mM EDTA, pH 7.5) at 37° C. for 15 min, without the optional chloroform:isoamyl alcohol extraction (earlier extractions showed no cosmetic improvement in results). Lastly, 2 μL ficoll loading dye (0.25% bromophenol blue, 15% ficoll, in 1×TBE buffer) was added and DNA samples were analyzed by 1.5% agarose gel electrophoresis using 1×TBE buffer (50 V, 180 min). The gel was stained with ethidium bromide (1 μg/mL) for 30 min with subsequent destaining for 30 min in pure water, and visualized with UV-transillumination (UVP transilluminator) using the Gel-Doc-It Imaging system (UVP).

DNA Binding by UV-Vis:

Optical titrations were carried out on 0.5-2 mL solutions of the PDCs with increasing amounts of calf thymus or herring sperm DNA to give [DNA bases]/[PDC] between 0.1 and 10. DNA was added in 1-5 μL increments to solutions of compound (10 μM) in 10 mM MOPS, 10 mM MOPS with 50 mM NaCl, 5 mM Tris-HC, or 5 mM Tris-HCl with 50 mM NaCl at pH 7.5. The dilution of compounds of the disclosure at the end of each titration, although negligible, was accounted for in the binding constant analyses. The DNA binding constant ($K_b$) was obtained from fits of the titration data to eq. 1 (FIG. 13), where $b=1+K_bC_t+K_b$ $[DNA]_t/2_s$, $C_t$ and $[DNA]_t$ represent the total PDC and DNA concentrations, respectively, s is the binding site size, and $\varepsilon_a$, $\varepsilon_f$, and $\varepsilon_b$ represent the molar extinction coefficients of the apparent, free, and bound PDCs, respectively. $\varepsilon_f$ was calculated at 414 nm for 7 and 412 nm for 8 before the addition of DNA, and $\varepsilon_a$ was determined at these wavelengths after each addition of DNA. The value of $\varepsilon_b$ was determined from the plateau of the DNA titration, where addition of DNA did not result in any further decrease in the absorption signal. Detailed fits of the titration data were obtained using both Kaleidagraph and Gnuplot.

DNA melting curves were constructed by measuring the absorbance ($A_{260}$) of a 2 mL, 25 μM DNA solution (40 mM MOPS, pH 7.5) as a function of temperature (20-100° C.) in the absence and presence of a compound of the disclosure (5 μM). Solutions of DNA and a compound of the disclosure for melting experiments were allowed to equilibrate for 30 min at 25° C. prior to measurement. The ETC-505T temperature controller was cooled with ice water (4° C.) using a fish-aquarium pump, and a stream of argon gas was supplied via the gas inlet valve to the sample compartment to prevent condensation on the cuvette windows during variable-temperature experiments.

Photocleavage Titrations:

DNA photocleavage experiments were performed according to a general plasmid DNA assay with 20 μL total sample volumes in 0.5 or 1.5 mL microfuge tubes containing transformed pUC19 plasmid (200 ng, >95% Form I) in 10 mM MOPS buffer and 100 mM NaCl, pH 7.4. DNA (1-5 μL) was delivered to the assay tubes as a solution in 10 mM Tris-Cl (pH 8.5) and diluted with MOPS (pH 7.5, final concentration 10 mM) and NaCl (final concentration 100 mM). Solutions of the compounds of the disclosure were added to give the from 0 to 500 μM, and the reaction mixtures were diluted to a final volume of 20 μL, when necessary, with distilled, deionized $H_2O$. Complexes were dissolved initially in acetonitrile (2 μM stock solutions), and all subsequent dilutions were made with distilled, deionized $H_2O$ where final assay tubes contained <1% acetonitrile. For concentration-based assays, samples (no pre-incubation period) were irradiated in air for 30 min with 420 nm light inside a photoreactor (Luzchem LZC-4X). Where irradiation of deoxygenated samples was required, argon was bubbled through the solutions for 15 min prior to irradiation under a positive pressure of argon. All samples were quenched by the addition of gel loading buffer (4 μL), loaded onto 1% agarose gels containing ethidium bromide (0.75 μg $mL^{-1}$), and electrophoresed for 30 min at 8-12 V $cm^{-1}$ in 1×TAE (40 mM Trisacetate, 1 mM EDTA, pH 8.2). The bands were visualized with UV-transillumination (UVP transilluminator) and quantified using the Gel Doc-It Imaging system (UVP) or GNU Image Manipulation Program (GIMP).

HL-60 Cell Culture:

HL-60 human promyelocytic leukemia cells (ATCC CCL-240) were cultured at 37° C. under 5% $CO_2$ in Hyclone's IMDM, supplemented with 20% FBS and were passaged 3-4 times per week according to standard aseptic procedures. Cultures were started at 200,000 cells $mL^{-1}$ in 25 $cm^2$ tissue culture flasks and were subcultured before growth reached 750,000 cells $mL^{-1}$ to avoid senescence associated with prolonged high cell density. Complete media was prepared in 200 mL portions as needed by combining IMDM (160 mL), FBS (40 mL, pre-aliquoted and heat inactivated), and gentamicin sulfate (100 μL of 50 mg mL$^{-1}$ stock solution) in a 250 mL Millipore vacuum stericup (0.22 μm) and filtering.

Cytotoxicity and Photocytotoxicity Assays

HL-60 cells growing in log phase (approximately 8×10$^5$) were transferred in 50 μL aliquots to two 96-well tissue-culture microplates (Corning Costar, Acton, Mass.) containing 100 μL warm culture medium and placed in a 37° C., 5% CO$_2$ water-jacketed incubator (Thermo Electron Corp., Forma Series II, Model 3110, HEPA Class 100) for one hour to equilibrate. All empty microplate wells contained 200 μL phosphate buffered saline (PBS) containing 2.68 mM potassium chloride, 1.47 mM potassium phosphate monobasic, 0.137 M sodium chloride, and 8.10 mM sodium phosphate dibasic, pH 7.4, to help minimize evaporation loss. Warm 50 μL aliquots of solution of compounds of the disclosure (4, 20, 40, 200 μM), freshly made in PBS, were added to the cells and incubated at 37° C. under 5% CO$_2$ for 4 hr (final concentrations were 1, 5, 10, 50 μM). One of the microplates was irradiated with visible light (400-700 nm) in a Luzchem photoreactor (cool white fluorescent tubes, 21 W/m$^2$) for 15 min; the other microplate was incubated under identical conditions in the dark. Both microplates were then incubated (37° C. under 5% CO$_2$) for 40 hr. A Cellometer Auto T4 (ESBE Scientific) was used to determine the cell number, viability, diameter, and % cell viability. Cell suspensions (20 μL) were diluted 1:1 with 0.2% trypan blue dye (Sigma Aldrich, Canada), loaded into a cell counting chamber-slide, and inserted into the imaging-based automatic cell counter. Cell concentration and cell viability were automatically determined (Cellometer Auto Counter Software) on the basis of the total cell count, the dilution factor, and the trypan blue dye exclusion. The optimal cell type parameters were established by importing the settings for HL-60 cells, and the data was subsequently imported into a Microsoft excel spreadsheet (Microsoft Office 2010) for data analysis.

Cytotoxicity and Photocytotoxicity Assays:

HL-60 cells growing in log phase were transferred (typically 25 μL aliquots) to 96-well tissue-culture plates (Corning Costar, Acton, Mass.) containing culture medium either with or without varying concentrations of the compounds of the disclosure to give final volumes in the culture wells of 100 μL and 10,000-20,000 cells. Solutions of compounds of the disclosure in complete media were prepared in 1 mL portions, where acetonitrile from the initial compounds of the disclosure stock solution was <0.5% v/v, and sterile-filtered in 3 mL syringes equipped with 0.22 μm Nalgene filters. Plates were incubated at 37° C. under 5% CO$_2$ for 30 min prior to exposure to 420 nm light in a Luzchem photoreactor for 30 min; dark controls were incubated under identical conditions in the dark. Dark controls, or cytotoxicity (CT) assays, refer to assays that include compounds of the disclosure but were not exposed to light, and light controls refer to light-exposed assays that did not contain compounds of the disclosure. Photocytotoxicity (PCT) assays contained PDC and were exposed to light. Cell counts and viability staining were carried out immediately and at ~24 h following light exposure. Manual counts were performed on 25 μL 1:1 mixtures of assay culture and trypan blue solution in a Neubauer hemocytometer viewed under an inverted light microscope in phase-contrast mode (4× objective, 60× total magnification). Under these conditions, viable cells appeared bright white, and non-viable cells were blue. All experiments were carried out in triplicate, and the graphed data is the average of three trials.

Viability Staining:

Viability was established according to a published protocol whereby a 100× stock solution of ethidium bromide/acridine orange (EB/AO) was prepared by dissolving ethidium bromide (50 mg) and acridine orange (15 mg) in 95% ethanol (1 mL) and diluting 1/50 with distilled, deionized H$_2$O. The 100× solution was divided into 1 mL aliquots and stored at −20° C. A 1× working solution was made by thawing a 1 mL aliquot of the 100× stock solution and diluting 1/100 with phosphate-buffered saline. The working solution was stored in an amber bottle at 4° C. for up to 1 month. For cellular viability staining, an aliquot of cell suspension was adjusted to 1-5×10$^6$ cells mL$^{-1}$ in phosphate-buffered IMDM. A 25 μL aliquot of this cell suspension was mixed with 1×EB/AO staining solution (25 μL) in a microfuge tube; a 25 μL aliquot of this cell-stain mixture was transferred to a hemocytometer and viewed under a Nikon Eclipse TE2000-U inverted light microscope operating in epi-fluorescence mode (10× or 40× objective, 150× or 600× total magnification). Under these conditions, viable cells took up AO and excluded EB, resulting in only green fluorescence with UV-excitation. Non-viable cells (apoptotic or necrotic) assimilated EB and fluoresced red with green excitation, overwhelming any green fluorescence from AO. Apoptotic cells were discerned from the formation of smaller, apoptotic bodies that fluoresced red.

Nuclear Staining for Laser Scanning Confocal Microscopy (LSCM)

HL-60 human promyelocytic leukemia cells (ATCC CCL-240) growing in log phase were transferred in aliquots of 100 μL (approximately 50,000 cells) to a 96-well tissue-culture microplate (Corning Costar, Acton, Mass.) containing 150 μL warm culture medium (Hyclone's IMDM supplemented with 20% FBS), and placed in a 37° C., 5% CO$_2$ water-jacketed incubator (Thermo Electron Corp., Forma Series II, Model 3110, HEPA Class 100) for one hour to equilibrate. Then, 50 μL of a 600 μM solution of a compounds of the disclosure (warmed to 37° C.), made in phosphate buffered saline (PBS) containing 2.68 mM potassium chloride, 1.47 mM potassium phosphate monobasic, 0.137 M sodium chloride, and 8.10 mM sodium phosphate dibasic, pH 7.4, was added. The microplate was returned to the incubator for 15 min. The 300 μL sample was then transferred to a collagen-coated glass-bottom tissue culture dish (FluoroDish FD35COL, World Precision Instruments Inc.) and returned to the incubator for 10-15 min to allow cells to adhere to the coated dish. The volume of the tissue culture dish was subsequently topped up to 2 mL with warm PBS for LSCM.

While the invention has been described in detail and with reference to specific examples thereof, it will be apparent to one skilled in the art that various changes and modifications can be made therein without departing from the spirit and scope thereof.

What is claimed is:

1. A compound having the formula (V)

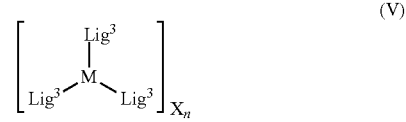

including hydrates, solvates, pharmaceutically acceptable salts, prodrugs and complexes thereof, wherein:

M is selected from the group consisting of osmium, manganese, molybdenum, rhenium, ruthenium, iron, cobalt, rhodium, iridium, nickel, and platinum;

X is selected from the group consisting of Cl⁻, $PF_6^-$, Br⁻, $BF_4^-$, $ClO_4^-$, $CF_3SO_3^-$, and $SO_4^{-2}$;

n=0, 1, 2, 3, 4, or 5;

Lig³ is a bidentate ligand that at each occurrence is each independently selected from the group consisting of

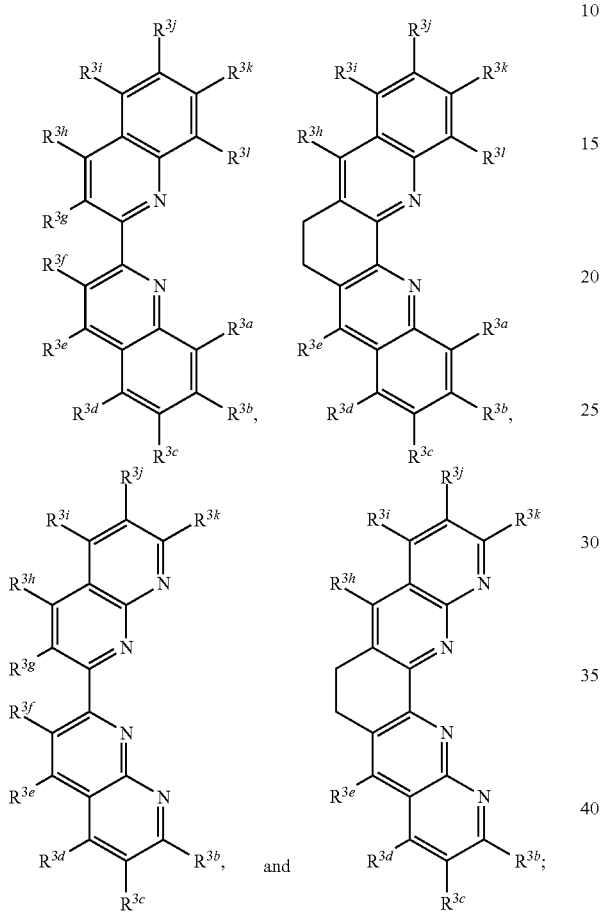

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^8$ at each occurrence is independently selected from the group consisting of hydrogen and optionally substituted alkyl;

wherein: (a) the compound is not Os(biq)₃(ClO₄)₂·H₂O, where biq is 2,2'-biquinoline, and (b) when M is ruthenium: (i) no more than two substituents on M are identical, and (ii) no more than one substituent on M is 2,2'-biquinoline.

2. A compound having the formula [Os(biq)₂(Lig)]Xₙ, where:

X is selected from the group consisting of Cl⁻, $PF_6^-$, Br⁻, $BF_4^-$, $ClO_4^-$, $CF_3SO_3^-$, and $SO_4^{-2}$;

n=0, 1, 2, 3, 4, or 5;

Lig is a bidentate ligand other than unsubstituted biq selected from the group consisting of

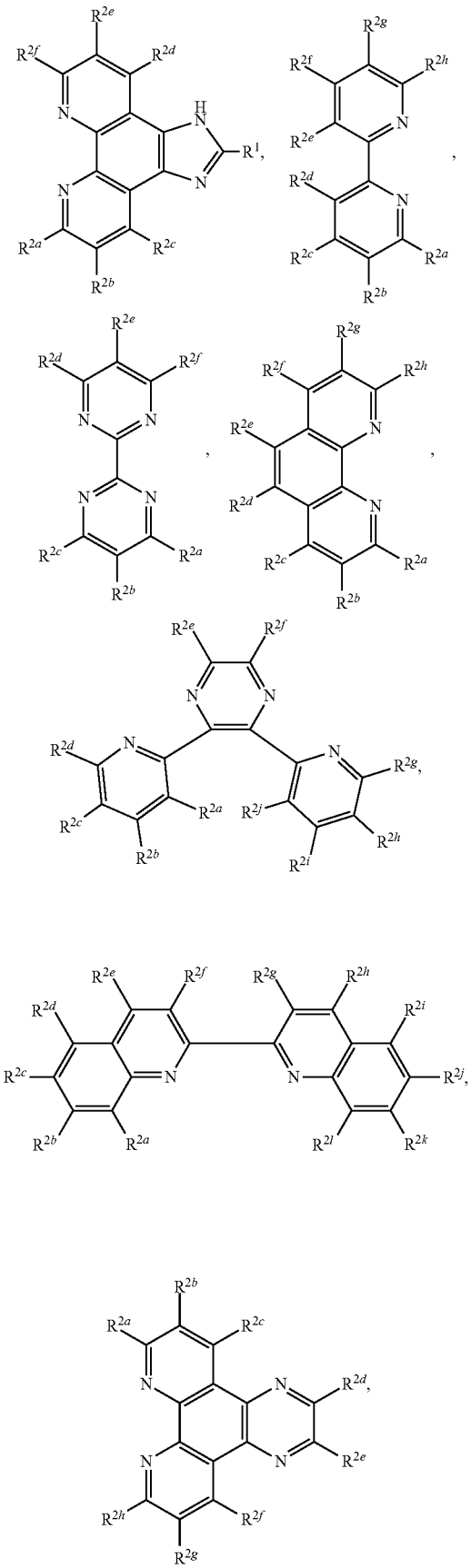

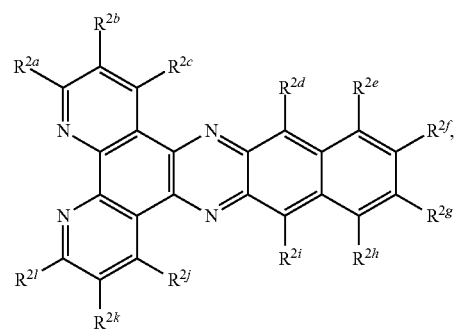
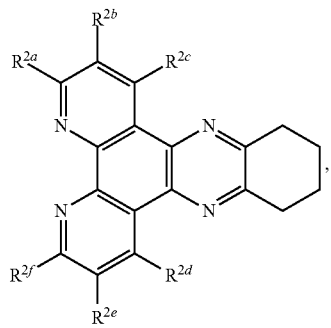
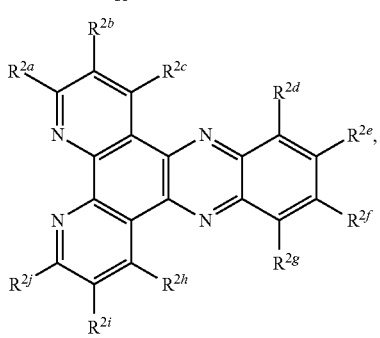
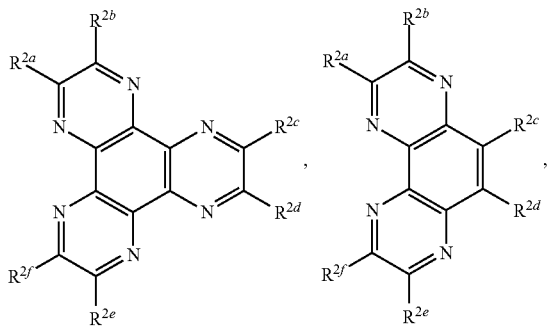
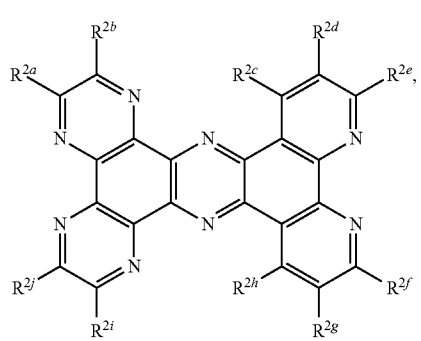
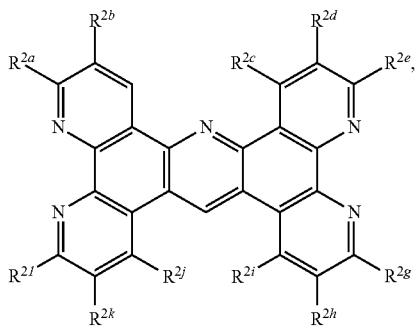
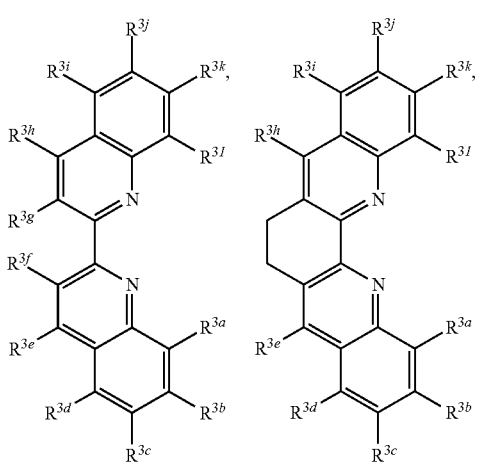
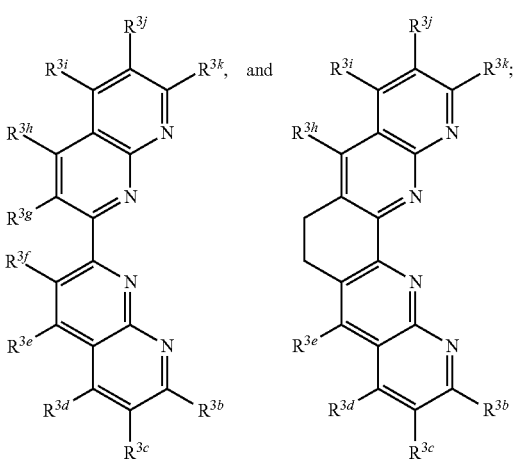
R¹ is selected from the group consisting of hydrogen, optionally substituted phenyl, optionally substituted aryl, optionally substituted heteroaryl, 4-pyridyl, 3-pyridyl, 2-thiazole, 2-pyrolyl, 2-furanyl,

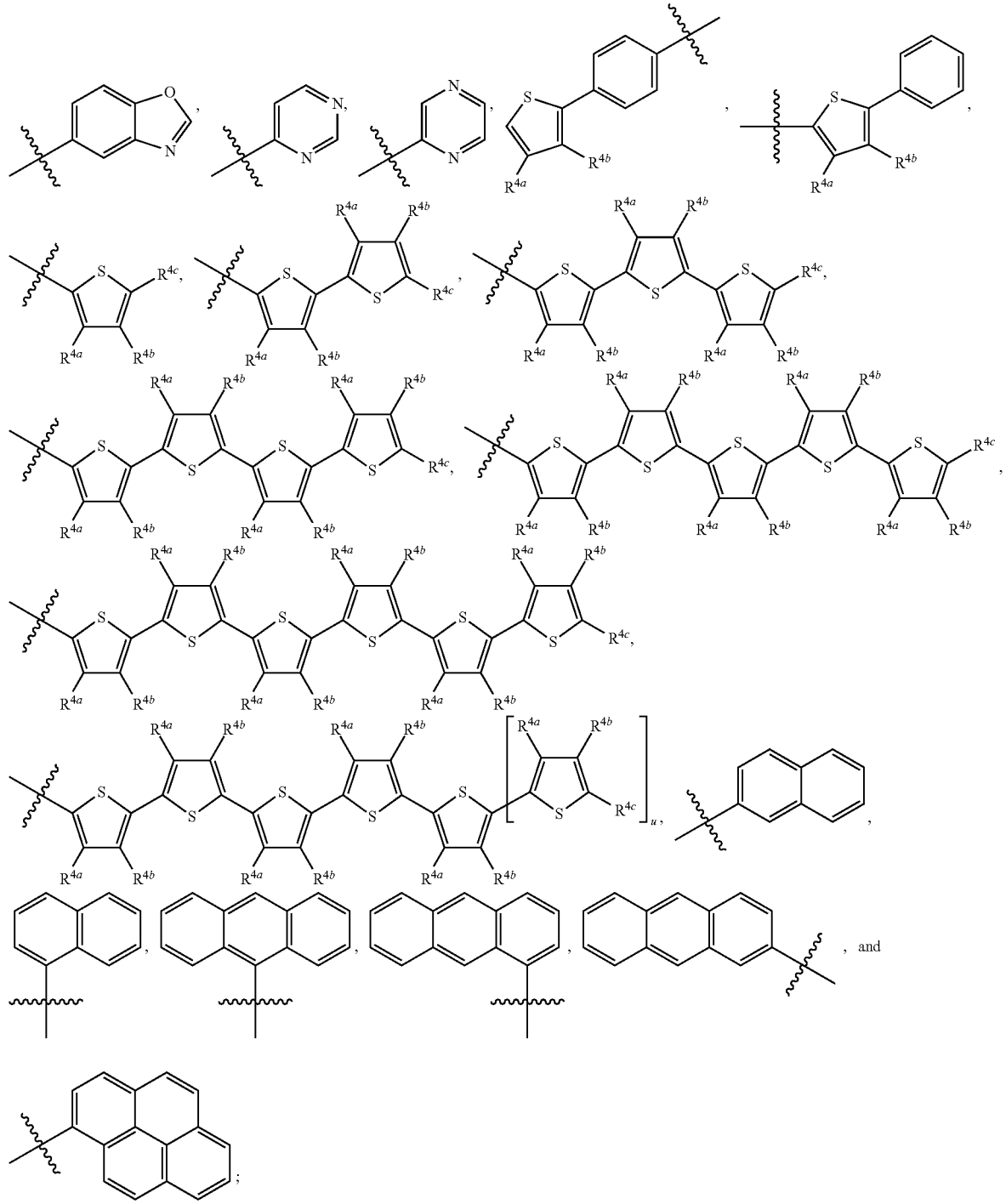

u is an integer;

$R^{2a}$, $R^{2b}$, $R^{2c}$, $R^{2d}$, $R^{2e}$, $R^{2f}$, $R^{2g}$, $R^{2h}$, $R^{2i}$, $R^{2j}$, $R^{2k}$, and $R^{2l}$ at each occurrence are each independently selected from the group consisting of hydrogen, $C_{1-6}$ optionally substituted alkyl, $C_{1-6}$ optionally substituted branched alkyl, $C_{3-7}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, $SO_3H$, sulfate, sulfonate, optionally substituted aryl, optionally substituted aryloxy, optionally substituted heteroaryl, and optionally substituted heterocycle;

$R^{3a}$, $R^{3b}$, $R^{3c}$, $R^{3d}$, $R^{3e}$, $R^{3f}$, $R^{3g}$, $R^{3h}$, $R^{3i}$, $R^{3j}$, $R^{3k}$, and $R^{3l}$ at each occurrence are each independently selected from the group consisting of hydrogen, $C_{1-6}$ optionally substituted alkyl, $C_{1-6}$ optionally substituted branched alkyl, $C_{1-6}$ optionally substituted haloalkyl, $C_{1-6}$ optionally substituted alkoxy, optionally substituted phenyl, and $CO_2R^8$;

$R^{4a}$, $R^{4b}$, and $R^{4c}$ at each occurrence are each independently selected from the group consisting of hydrogen, $C_{1-6}$ optionally substituted alkyl, $C_{1-6}$ optionally substituted branched alkyl, $C_{1-6}$ optionally substituted cycloalkyl, $C_{1-6}$ optionally substituted haloalkyl, $C_{1-6}$ optionally substituted alkoxy, $CO_2R^5$, $CONR^6_2$, $NR^7_2$, sulfate, sulfonate, optionally substituted aryl, optionally substituted aryloxy, optionally substituted heteroaryl, and optionally substituted heterocycle;

$R^{4a}$ and $R^{4b}$ at each occurrence on a thiophene ring are taken together with the atom to which they are bound to form an optionally substituted ring having from 6 ring atoms containing 2 oxygen atoms;

$R^5$ at each occurrence are each independently selected from the group consisting of hydrogen and optionally substituted alkyl;

$R^6$ at each occurrence are each independently selected from the group consisting of hydrogen and optionally substituted alkyl;

$R^7$ at each occurrence are each independently selected from the group consisting of hydrogen and optionally substituted alkyl;

$R^8$ at each occurrence are each independently selected from the group consisting of hydrogen and optionally substituted alkyl; and biq is 2,2'-biquinoline.

3. The compound of claim 2, wherein Lig is 1,10-phenanthroline, imidazo[4,5-f][1,10]phenathroline or benzo[i]dipyrido[3,2-α:2',3'-c]phenazine.

4. The compound of claim 3, wherein X is $Cl^-$ and n is 2.

* * * * *